(12) United States Patent
Takahashi et al.

(10) Patent No.: US 9,562,044 B2
(45) Date of Patent: Feb. 7, 2017

(54) 2-ACYLAMINOTHIAZOLE DERIVATIVE OR SALT THEREOF

(71) Applicant: ASTELLAS PHARMA INC., Chuo-ku (JP)

(72) Inventors: Taisuke Takahashi, Tokyo (JP); Jun Maeda, Tokyo (JP); Yusuke Inagaki, Tokyo (JP); Kenji Negoro, Tokyo (JP); Hiroaki Tanaka, Tokyo (JP); Kazuhiro Yokoyama, Tokyo (JP); Hajime Takamatsu, Tokyo (JP); Takanori Koike, Tokyo (JP); Issei Tsukamoto, Tokyo (JP)

(73) Assignee: Astellas Pharma Inc., Chuo-ku (JP)

( * ) Notice: Subject to any disclaimer, the term of this patent is extended or adjusted under 35 U.S.C. 154(b) by 0 days.

(21) Appl. No.: 14/770,648

(22) PCT Filed: Feb. 27, 2014

(86) PCT No.: PCT/JP2014/054803
§ 371 (c)(1),
(2) Date: Aug. 26, 2015

(87) PCT Pub. No.: WO2014/133056
PCT Pub. Date: Sep. 4, 2014

(65) Prior Publication Data
US 2016/0002218 A1      Jan. 7, 2016

(30) Foreign Application Priority Data

Feb. 28, 2013   (JP) ................................. 2013-039964

(51) Int. Cl.
| | | |
|---|---|---|
| *C07D 417/14* | (2006.01) | |
| *C07D 491/08* | (2006.01) | |
| *A61K 31/497* | (2006.01) | |
| *A61K 31/5377* | (2006.01) | |
| *C07D 491/107* | (2006.01) | |

(52) U.S. Cl.
CPC ........... *C07D 417/14* (2013.01); *A61K 31/497* (2013.01); *A61K 31/5377* (2013.01); *C07D 491/08* (2013.01); *C07D 491/107* (2013.01)

(58) Field of Classification Search
CPC  A61K 31/497; A61K 31/5377; C07D 417/14; C07D 491/08; C07D 491/107
See application file for complete search history.

(56) References Cited

U.S. PATENT DOCUMENTS

| | | | |
|---|---|---|---|
| 7,361,658 B2* | 4/2008 | Sugasawa .......... | C07D 417/04 514/252.13 |
| 2005/0153977 A1 | 7/2005 | Sugasawa et al. | |
| 2006/0194844 A1 | 8/2006 | Sugasawa et al. | |
| 2010/0222329 A1 | 9/2010 | Sugasawa et al. | |
| 2010/0222361 A1 | 9/2010 | Sugasawa et al. | |
| 2013/0079351 A1 | 3/2013 | Sugasawa et al. | |

FOREIGN PATENT DOCUMENTS

| | | |
|---|---|---|
| EP | 1 466 912 A1 | 10/2004 |
| EP | 1 647 553 A1 | 4/2006 |
| JP | 2006-219480 A | 8/2006 |
| JP | 2006-219481 A | 8/2006 |
| WO | WO 03/062233 A1 | 7/2003 |
| WO | WO 2004/096800 A2 | 11/2004 |
| WO | WO 2005/007651 A1 | 1/2005 |
| WO | WO 2012/016217 A1 | 2/2012 |

OTHER PUBLICATIONS

International Search Report issued Jun. 3, 2014 in PCT/JP2014/054803 (with English language translation).
Anna Tarasova, et al., "Modelling Atypical Small-Molecule Mimics of an Important Stem Cell Cytokine, Thrombopoietin" ChemMedChem, vol. 4, 2009, pp. 2002-2011.
S. Lazareno, et al., "Analogs of WIN 62,577 Define a Second Allosteric Site on Muscarinic Receptors" Molecular Pharmacology, vol. 62, No. 6, 2002, pp. 1492-1505.
Nigel J. M. Birdsall, et al., "Subtype-Selective Positive Cooperative Interactions Between Brucine Analogs and Acetylcholine at Muscarinic Receptors: Functional Studies" Molecular Pharmacology, vol. 55, 1999, pp. 778-787.
Office Action issued Oct. 26, 2015 in Vietnamese Patent Application No. 1-2015-03188 (with English language translation).
Office Action issued Jul. 21, 2016 in Algerian Patent Application No. 2015/00504 (with English language translation).
Extended European Search Report issued on Jul. 1, 2016 in Patent Application No. 14757377.8.
Combined Singaporean Search Report and Written Opinion issued on Jul. 15, 2016 in Patent Application No. 11201506713T.
Office Action issued on Jun. 6, 2016 in Saudi Arabian Patent Application No. 515360956 (with English language translation).
Office Action issued May 5, 2016 in Eurasian Patent Application No. 201591391 (with English language translation).

* cited by examiner

*Primary Examiner* — Valerie Rodriguez-Garcia
(74) *Attorney, Agent, or Firm* — Oblon, McClelland, Maier & Neustadt, L.L.P.

(57) ABSTRACT

Thiazole derivatives having pyrazine-2-carbonylamino substituted at the 2-position of the following formula (I):

(I)

[Chemical structure showing a thiazole ring with $R^1$ and $R^2$ substituents connected via an amide linkage to a pyrazine ring, which is connected to a piperidine ring bearing $CO_2H$ and $R^3$ substituents]

are excellent muscarinic $M_3$ receptor positive allosteric modulators, and are useful for treating bladder or urinary tract diseases, related to bladder contraction by a muscarinic $M_3$ receptor. The 2-acylaminothiazole derivatives and salts thereof can be used for treating bladder or urinary tract diseases, related to bladder contraction by a muscarinic $M_3$ receptor, for example, voiding dysfunctions such as underactive bladder.

16 Claims, 3 Drawing Sheets

2-ACYLAMINOTHIAZOLE DERIVATIVE OR SALT THEREOF

TECHNICAL FIELD

The present invention relates to a 2-acylaminothiazole derivative or a salt thereof, which is useful as an active ingredient of a pharmaceutical composition, in particular, a pharmaceutical composition for treating bladder or urinary tract diseases, related to bladder contraction by a muscarinic $M_3$ receptor.

BACKGROUND ART

Important roles of the lower urinary tract are urine storage and voiding, which are regulated by a coordinated action of the bladder and the urethra. That is, during urine storage, the bladder smooth muscle is relaxed and the urethral sphincter is contracted, whereby a state of high urethral resistance is maintained and urinary continence is thus maintained. On the other hand, during voiding, while the bladder smooth muscle is contracted, the urethral smooth muscle is relaxed, and contraction of the external urethral sphincter is also inhibited. Examples of disorders in the lower urinary tract include storage dysfunctions such as overactive bladder in which urine cannot be retained during urine storage and voiding dysfunctions in which urine cannot be drained sufficiently during voiding due to increase in the urethral resistance or decrease in the bladder contractile force. These two dysfunctions may develop simultaneously in some cases.

Voiding dysfunctions are caused by a decrease in the bladder contractile force or an increase in urethral resistance during voiding, and lead to voiding difficulty, straining during voiding, attenuation of the urinary stream, extension of voiding time, an increase in residual urine, a decrease in voiding efficiency, or the like. A decrease in the bladder contractile force during voiding is called underactive bladder, acontractile bladder, or the like. As a factor for decreasing the bladder contractile force during voiding, there are known increasing age, diabetes mellitus, benign prostatic hyperplasia, neurological diseases such as Parkinson's disease and multiple sclerosis, spinal cord injury, nerve damage caused by pelvic surgery, and the like (Reviews in Urology, 15: pp. 11-22 (2013)).

As a mechanism that induces bladder contraction during voiding, involvement of muscarinic receptor stimulation is known. In other words, the pelvic nerve that is a parasympathetic nerve innervating the bladder is excited during voiding, and acetylcholine is released from nerve terminals. The released acetylcholine binds to a muscarinic receptor in the bladder smooth muscle to cause contraction of the bladder smooth muscle (Journal of Pharmacological Sciences, 112: pp. 121-127 (2010)). The muscarinic receptors are currently divided into five subtypes, $M_1$, $M_2$, $M_3$, $M_4$, and $M_5$, and it is known that a subtype involved in contraction of the bladder smooth muscle is mainly $M_3$ (Pharmacological Reviews, 50: pp. 279-290 (1998), and The Journal of Neuroscience, 22: pp. 10627-10632 (2002)).

As a therapeutic agent for a decrease in the bladder contractile force during voiding, bethanechol chloride which is a non-selective muscarinic receptor agonist or distigmine bromide which is a choline esterase inhibitor is known. However, it is known that these drugs have cholinergic side effects, such as diarrhea, abdominal pain, and sweating. Further, cholinergic crisis is sometimes occurred as a serious side effect, therefore carefulness is required for the use (UBRETID (registered trademark) tablet 5 mg package insert, Torii Pharmaceutical Co., Ltd., Besacolin (registered trademark) powder 5% package insert, Eisai Co., Ltd.).

On the other hand, as a cause of an increase in urethral resistance, a voiding dysfunction associated with benign prostatic hyperplasia is well-known, which is characterized by partial obstruction of the urethra due to nodular hypertrophy of the prostate tissues. Adrenergic $\alpha_1$ receptor antagonists have now been used as therapeutic agents for the voiding dysfunction associated with benign prostatic hyperplasia (Pharmacology, 65: pp. 119-128 (2002)). On the other hand, the effectiveness of adrenergic $\alpha_1$ receptor antagonists on voiding dysfunctions not associated with benign prostatic hyperplasia is unclear, as compared with the voiding dysfunction associated with benign prostatic hyperplasia (Journal of Pharmacological Sciences, 112: pp. 121-127 (2010)).

Further, in voiding dysfunctions caused by a decrease in the bladder contractile force or an increase in the urethral resistance, residual urine after voiding may be observed in some cases. Increased residual urine may cause a decrease in effective bladder capacity, and thus cause overactive bladder symptoms such as urinary frequency, or severe symptoms, such as hydronephrosis, in some cases.

There is a demand for a therapeutic agent which is more effective on bladder or urinary tract diseases or symptoms thereof caused by a decrease in the bladder contractile force or an increase in the urethral resistance during voiding.

In Patent Document 1, it is described that a compound represented by the following general formula (A), including a compound of the following formula A1 disclosed in Example 315, has a Ba/F3 cell proliferative activity through a human c-myeloproliferative leukemia virus type P (c-Mpl) and has a thrombocyte increasing activity.

[Chem. 1]

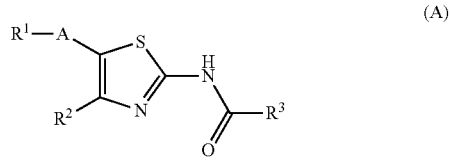

(A)

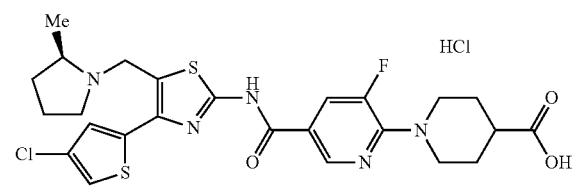

(A1)

(in which $R^3$ represents an aromatic hetero ring which may be substituted. For the other symbols, refer to the patent publication.)

In Patent Document 2, it is described that a compound represented by the following general formula (B), including a compound of the following formula B1 disclosed as the compound 38, has an activating effect on an AMPK pathway.

[Chem. 2]

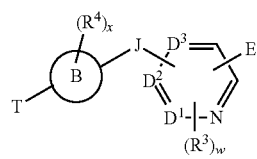

(B)

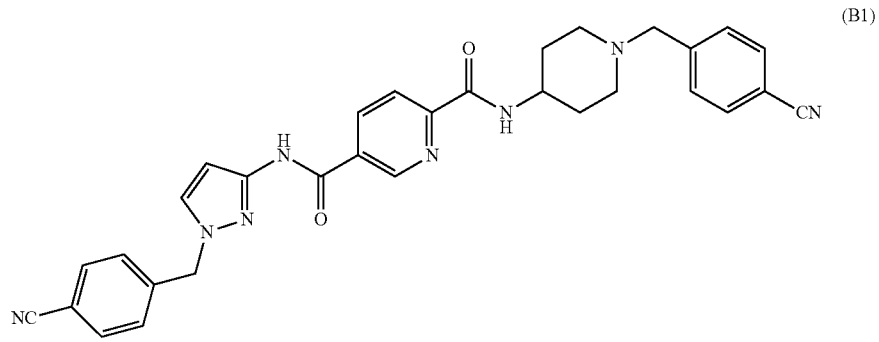

(B1)

(in which a ring B represents a heteroarylene or the like, J represents —NR¹³C(O)— or the like, D¹, D², and D³ represent N, CH, or the like, and E represents —NR¹R² or the like. For the other symbols, refer to the patent publication.)

RELATED ART

Patent Document

[Patent Document 1] Pamphlet of International publication WO 2005/007651
[Patent Document 2] Pamphlet of International publication WO 2012/016217

DISCLOSURE OF INVENTION

Problems to be Solved by the Invention

The present invention is to provide a compound which is useful as an active ingredient of a pharmaceutical composition, in particular, a pharmaceutical composition for preventing or treating bladder or urinary tract diseases, related to bladder contraction by a muscarinic $M_3$ receptor.

Means for Solving the Problems

The present inventors have found that a thiazole derivative having pyrazine-2-carbonylamino substituted at the 2-position is an excellent muscarinic $M_3$ receptor positive allosteric modulator, and is useful as an agent for preventing and/or treating bladder or urinary tract diseases, related to bladder contraction by a muscarinic $M_3$ receptor, thereby completing the present invention.

That is, the present invention relates to a compound of the formula (I) or a salt thereof as well as a pharmaceutical composition comprising a compound of the formula (I) or a salt thereof and an excipient:

[Chem. 3]

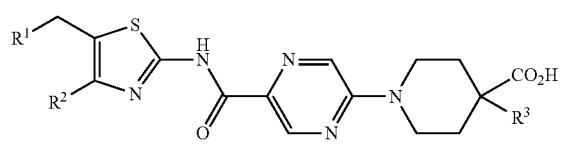

(I)

wherein
$R^1$ is —N(—$R^{11}$)(—$R^{12}$), or cyclic amino which may be substituted;
$R^{11}$ is $C_{1-6}$ alkyl;
$R^{12}$ is $C_{1-6}$ alkyl which may be substituted, or $C_{3-8}$ cycloalkyl which may be substituted;
$R^2$ is aryl which may be substituted, a monocyclic aromatic hetero ring which may be substituted, or a bicyclic aromatic hetero ring which may be substituted; and
$R^3$ is —H, —OH, —O—($C_{1-6}$ alkyl), or halogen.

In addition, unless otherwise specified, when symbols in a certain chemical formula in the present specification are also used in another chemical formula, the same symbol represents the same meaning.

Moreover, in Patent Document 1, there is no disclosure or suggestion of a specific compound that is the compound of the formula (A), in which $R^3$ is pyrazinyl, and there is also no disclosure or suggestion of an action on a muscarinic receptor or an action on bladder or urinary tract diseases.

Further, in Patent Document 2, there is no disclosure of a specific compound that is the compound of the formula (B), in which a ring B is thiazole, and there is no disclosure or suggestion of an action on a muscarinic receptor or an action on bladder or urinary tract diseases.

Furthermore, the present invention relates to a pharmaceutical composition, in particular, a pharmaceutical composition for preventing or treating bladder or urinary tract diseases, related to bladder contraction by a muscarinic $M_3$ receptor, comprising a compound of the formula (I) or a salt thereof. Further, the pharmaceutical composition includes an agent for preventing or treating bladder or urinary tract diseases, related to bladder contraction by a muscarinic $M_3$ receptor, comprising the compound of the formula (I) or a salt thereof.

In addition, the present invention relates to use of the compound of the formula (I) or a salt thereof for the manufacture of a pharmaceutical composition for preventing or treating bladder or urinary tract diseases, related to bladder contraction by a muscarinic $M_3$ receptor; use of the compound of the formula (I) or a salt thereof for preventing or treating bladder or urinary tract diseases, related to bladder contraction by a muscarinic $M_3$ receptor; the compound of the formula (I) or a salt thereof for preventing or treating bladder or urinary tract diseases, related to bladder contraction by a muscarinic $M_3$ receptor; and a method for preventing or treating bladder or urinary tract diseases, related to bladder contraction by a muscarinic $M_3$ receptor, comprising administering to a subject an effective amount of the compound of the formula (I) or a salt thereof. In addition, the "subject" is a human or another mammal in need of such prevention or treatment, and in a certain embodiment, a human in need of such prevention or treatment.

Effects of the Invention

The compound of the formula (I) or a salt thereof can be used as an agent for preventing and/or treating bladder or urinary tract diseases, related to bladder contraction by a muscarinic $M_3$ receptor, as a muscarinic $M_3$ receptor positive allosteric modulator.

EMBODIMENTS FOR CARRYING OUT THE INVENTION

Figure 1:
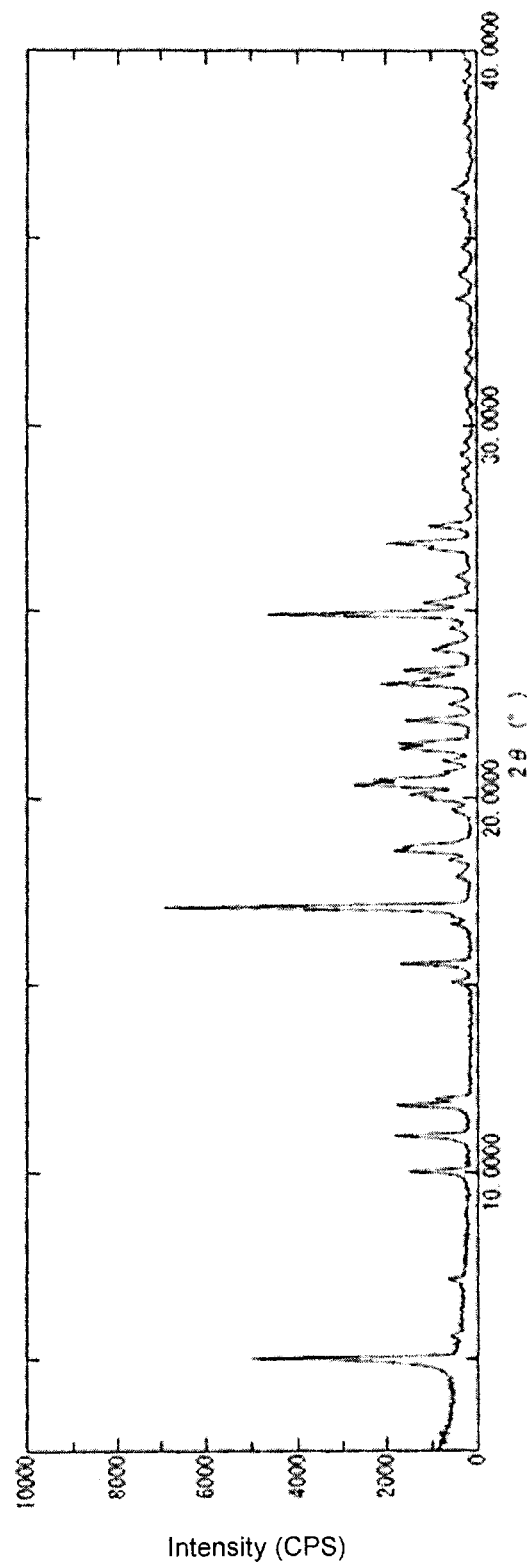
FIG. 1 shows a powder X-ray diffraction pattern of the compound of Example 8.
Figure 2:
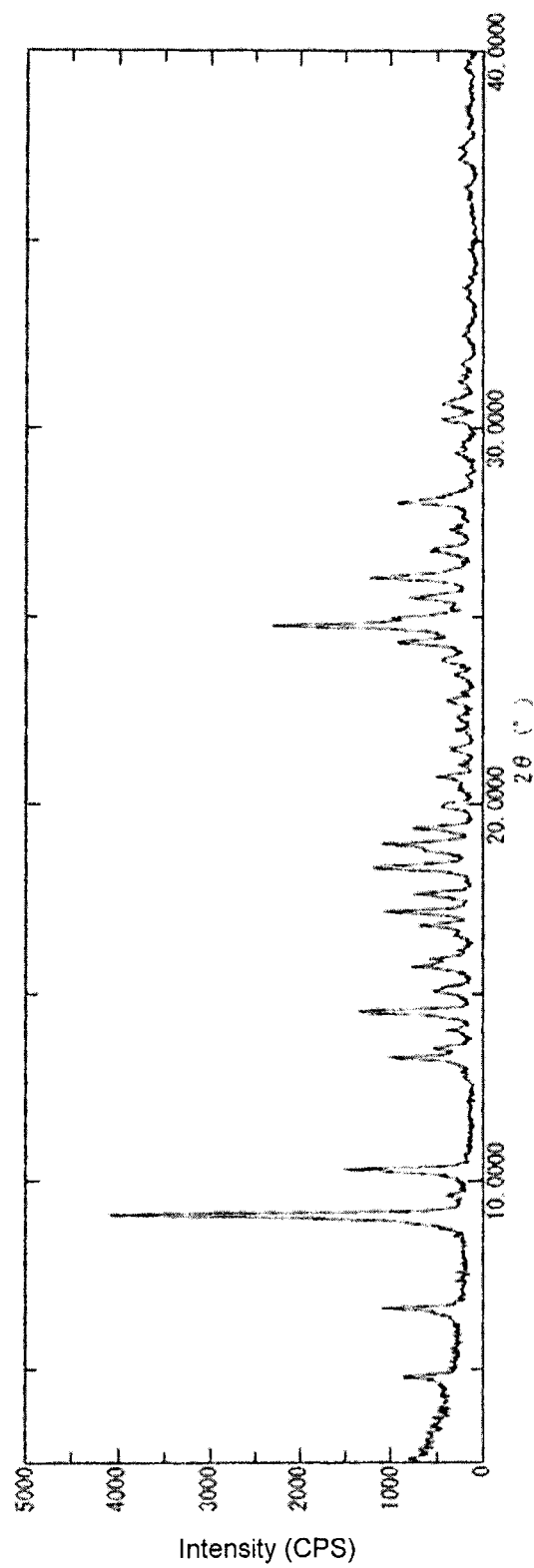
FIG. 2 shows a powder X-ray diffraction pattern of the compound of Example 206.
Figure 3:
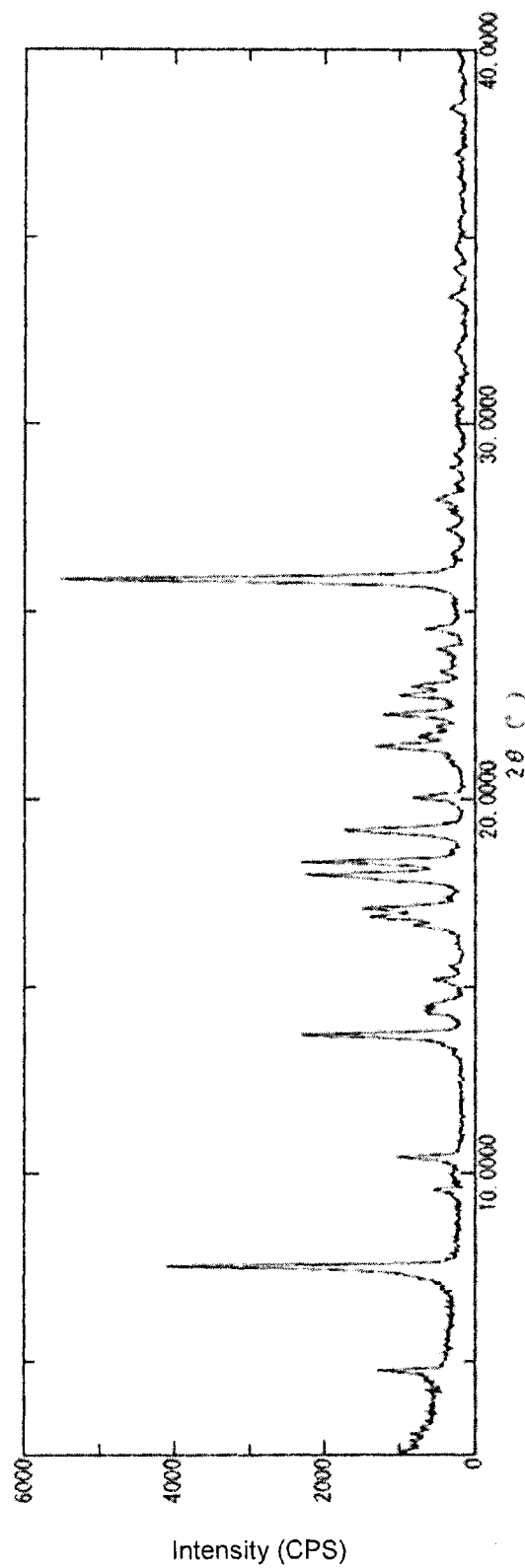
FIG. 3 shows a powder X-ray diffraction pattern of the compound of Example 207.

Hereinafter, the present invention will be described in detail.

A positive allosteric modulator is a compound which binds to an allosteric site other than a ligand-binding site, mainly to cause a change in the structures of a receptor, thereby, has effects of increasing the affinity of an agonist to the receptor and changing the signal level of the agonist. In the living body, the positive allosteric modulator itself does not exhibit an agonistic effect, and increases the effect of an endogenous agonist. Examples of the advantage of the positive allosteric modulator over the agonist include (1) that since the positive allosteric modulator exhibits an enhancement in the endogenous agonist stimulation-dependently, the side effects can be avoided, (2) that since the positive allosteric modulator binds to a site other than the ligand-binding site, a high subtype selectivity can be obtained, and (3) that desensitization shown in an agonist is hardly occurred (Pharmacological Reviews, 63: pp. 59-126 (2011)).

In the present specification, the muscarinic $M_3$ receptor positive allosteric modulator means a compound which enhances an effect by a muscarinic $M_3$ receptor in an agonist stimulation-dependent or nerve stimulation-dependent manner. Accordingly, the effect on increasing bladder contraction is expected only during voiding, and thus, it is thought that the muscarinic $M_3$ receptor positive allosteric modulator is useful as an agent for improving various symptoms accompanying voiding dysfunctions. Further, by an action specific to the voiding, it is expected that the cholinergic side effects known as bethanechol chloride or distigmine bromide can be avoided. Further, since the muscarinic $M_3$ receptor positive allosteric modulator increases the bladder contractile force during voiding, the effect on voiding dysfunctions that are caused by an increase in the urethral resistance can also be expected. The decrease in the residual urine by the improvement of voiding dysfunctions leads to an increase in the effective bladder capacity, and thus, improvement of urine storage functions and avoidance of renal disorders can be expected. As such, the muscarinic $M_3$ receptor positive allosteric modulator is expected to be useful as an agent for preventing and/or treating bladder or urinary tract diseases, related to bladder contraction by a muscarinic $M_3$ receptor. The present inventors have newly found a compound that acts as the modulator, thereby completing the present invention.

In the present specification,

Examples of the "bladder or urinary tract diseases, related to bladder contraction by a muscarinic $M_3$ receptor" include voiding and storage dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like, and preferably voiding and storage dysfunctions in underactive bladder, hypotonic bladder, acontractile bladder, detrusor underactivity and neurogenic bladder.

The "alkyl" includes linear alkyl and branched alkyl. Accordingly, the "$C_{1-6}$ alkyl" is linear or branched alkyl having 1 to 6 carbon atom(s), and specific examples thereof include methyl, ethyl, n-propyl, isopropyl, n-butyl, isobutyl, sec-butyl, tert-butyl, n-pentyl, and n-hexyl. In a certain embodiment, the $C_{1-6}$ alkyl is methyl, ethyl, n-propyl, isopropyl, n-butyl, isobutyl, sec-butyl, or tert-butyl.

The "cycloalkyl" is a saturated hydrocarbon ring group. Accordingly, the "$C_{3-8}$ cycloalkyl" is a saturated hydrocarbon ring group having 3 to 8 ring members, and specific examples thereof include cyclopropyl, cyclobutyl, cyclopentyl, cyclohexyl, cycloheptyl, and cyclooctyl. In a certain embodiment, the $C_{3-8}$ cycloalkyl is cyclopropyl, cyclobutyl, cyclopentyl, or cyclohexyl; and in another embodiment, cyclopropyl.

The "aryl" is a $C_{6-14}$ monocyclic to tricyclic aromatic hydrocarbon ring group, and specific examples thereof include phenyl, naphthyl, tetrahydronaphthyl, indanyl, and indenyl. In a certain embodiment, the aryl is phenyl.

The "monocyclic aromatic hetero ring" is a monocyclic aromatic hetero ring group having 5 to 7 ring members, which has 1 to 4 hetero atom(s) selected from the group consisting of a nitrogen atom, an oxygen atom, and a sulfur atom as a ring-constituting atom. Specific examples thereof include pyrrolyl, pyrazolyl, imidazolyl, triazolyl, furanyl, thienyl, oxazolyl, oxadiazolyl, thiazolyl, thiadiazolyl, pyridyl, pyridazinyl, pyrimidinyl, and pyrazinyl. In a certain embodiment, the monocyclic aromatic hetero ring is thienyl or thiazolyl; and in another embodiment, thienyl.

The "bicyclic aromatic hetero ring" is a bicyclic aromatic hetero ring group, in which the monocyclic aromatic hetero ring is fused with a benzene ring or a monocyclic aromatic hetero ring, and includes its partially hydrogenated ring group. Specific examples thereof include indolyl, isoindolyl, indazolyl, benzotriazolyl, benzofuranyl, benzothienyl, benzoxazolyl, benzothiazolyl, quinolyl, isoquinolyl, cinnolinyl, quinazolinyl, quinoxalinyl, naphthyridinyl, fropyridyl, thienopyridyl, indolinyl, dihydrobenzofuranyl, dihydrobenzothienyl, dihydroquinolyl, tetrahydroquinolyl, dihydroisoquinolyl, tetrahydroisoquinolyl, dihydrofropyridyl, and dihydrothienopyridyl. In a certain embodiment, the bicyclic aromatic hetero ring is dihydrobenzofuranyl.

The "saturated hetero ring" is a 3- to 8-membered saturated ring group which has 1 to 4 hetero atom(s) selected from the group consisting of a nitrogen atom, an oxygen atom, and a sulfur atom as a ring-constituting atom, and may be bridged with lower alkylene, and its sulfur atom as a ring-constituting atom may be oxidized.

The "cyclic amino" is a group having a bond at a nitrogen atom constituting the ring of the saturated hetero rings above, and specific examples thereof include pyrrolidin-1-yl, piperidin-1-yl, azetidin-1-yl, azepan-1-yl, azocan-1-yl, morpholin-4-yl, thiomorpholin-4-yl, piperazin-1-yl, 1,4-diazepan-1-yl, 1,4-oxazepan-4-yl, and 1,4-thiazepan-4-yl. In a certain embodiment, the cyclic amino is pyrrolidin-1-yl, piperidin-1-yl, azetidin-1-yl, or morpholin-4-yl; and in another embodiment, pyrrolidin-1-yl or piperidin-1-yl.

The cyclic amino in $R^1$ may be combined with the cyclic amino to form a Spiro ring. In this case, specific examples of the cyclic amino include 2-oxa-6-azaspiro[3.5]nonan-6-yl, 2,6-diazaspiro[3.5]nonan-6-yl, 2-thia-6-azaspiro[3.5]nonan-6-yl, 2-oxa-8-azaspiro[4.5]decan-8-yl, 6-oxa-9-azaspiro[4.5]decan-9-yl, 3-oxa-9-azaspiro[5.5]undecan-9-yl, and the like.

The "halogen" means fluoro, chloro, bromo, or iodo. In a certain embodiment, it is fluoro, chloro, or bromo; and in another embodiment, fluoro or chloro.

In the present specification, the expression "which may be substituted" means "which is not substituted" or "which is substituted with 1 to 5 substituent(s)". Further, if it has a plurality of substituents, the substituents may be the same as or different from each other.

Examples of the substituent acceptable for the "cyclic amino which may be substituted", "$C_{1-6}$ alkyl which may be substituted", "$C_{3-8}$ cycloalkyl which may be substituted", "aryl which may be substituted", "monocyclic aromatic hetero ring which may be substituted", and "bicyclic aromatic hetero ring which may be substituted" include the substituents in the following Group G; and in another embodiment, the substituents described in (a) to (g) and (m) to (o) in the following Group G:

Group G (a) $C_{1-6}$ alkyl which may be substituted with at least one group selected from the group consisting of —OH, —O—($C_{1-6}$ alkyl), —CN, —SO$_2$—$C_{1-6}$ alkyl, and halogen,
(b) —OH,
(c) —O—($C_{1-6}$ alkyl which may be substituted with at least one group selected from the group consisting of —OH, —O—($C_{1-6}$ alkyl), —CN, —SO$_2$—$C_{1-6}$ alkyl, and halogen),
(d) $C_{3-8}$ cycloalkyl,
(e) —O—($C_{3-8}$ cycloalkyl),
(f) halogen,
(g) —CN,
(h) —SO$_2$—$C_{1-6}$ alkyl,
(i) —CO$_2$—$C_{1-6}$ alkyl and —COOH,
(j) —CO—N($C_{1-6}$ alkyl)$_2$, —CO—NH($C_{1-6}$ alkyl), and —CONH$_2$,
(k) —CO—$C_{1-6}$ alkyl,
(l) —SO$_2$—N($C_{1-6}$ alkyl)$_2$, —SO$_2$—NH($C_{1-6}$ alkyl), and —SO$_2$NH$_2$,
(m) —N($C_{1-6}$ alkyl)$_2$, —NH($C_{1-6}$ alkyl), and, —NH$_2$,
(n) a saturated hetero ring, and
(o) an —O-saturated hetero ring.

Further, examples of the substituent in the "cyclic amino which may be substituted" include oxo (=O).

The substituent acceptable in the "cyclic amino which may be substituted" in $R^1$ is, in a certain embodiment, the substituents shown in (a) to (d), (f) and (g) in the Group G;

in another embodiment, a substituent shown in the following Group G1:

Group G1

$C_{1-6}$ alkyl which may be substituted with the same or different 1 to 3 substituent(s) selected from the group consisting of —OH, —O—($C_{1-6}$ alkyl), and halogen; —O—($C_{1-6}$ alkyl); $C_{3-8}$ cycloalkyl; halogen; and —CN;

in another embodiment, $C_{1-6}$ alkyl which may be substituted with the same or different 1 to 3 substituent(s) selected from the group consisting of —OH, —O—($C_{1-6}$ alkyl), and halogen;

in still another embodiment, $C_{1-6}$ alkyl which may be substituted with the same or different 1 to 3 substituent(s) selected from the group consisting of —O—($C_{1-6}$ alkyl) and halogen;

in further still another embodiment, $C_{1-6}$ alkyl which may be substituted with the same or different 1 to 3 —O—($C_{1-6}$ alkyl) group(s);

in further still another embodiment, $C_{1-6}$ alkyl; and in further still another embodiment, methyl or ethyl.

The substituent acceptable for the "$C_{1-6}$ alkyl which may be substituted" in $R^{12}$ is, in a certain embodiment, the substituents shown in (b) to (o) in the Group G;

in another embodiment, $C_{3-8}$ cycloalkyl, —O—($C_{1-6}$ alkyl), —O—($C_{3-8}$ cycloalkyl), halogen, —CN, or cyclic amino; and in still another embodiment, —O—($C_{1-6}$ alkyl).

The substituent acceptable for the "$C_{3-8}$ cycloalkyl which may be substituted" in $R^{12}$ is, in a certain embodiment, the substituents shown in (a) to (c), (f) and (g) in the Group G; and in another embodiment, $C_{1-6}$ alkyl which may be substituted with —O—($C_{1-6}$ alkyl).

The substituent acceptable for the "aryl which may be substituted" in $R^2$ is, in a certain embodiment, the substituents shown in (a) to (c), (f), (g) and (m) to (o) in the Group G;

in another embodiment, the substituents shown in the following Group G2:

Group G2

$C_{1-6}$ alkyl which may be substituted with the same or different 1 to 5 halogen(s); —O—($C_{1-6}$ alkyl which may be substituted with the same or different 1 to 5 substituent(s) selected from the group consisting of halogen and —O—($C_{1-6}$ alkyl)); an —O-saturated hetero ring; halogen; —N($C_{1-6}$alkyl)$_2$; —NH($C_{1-6}$ alkyl); —NH$_2$; and cyclic amino;

in still another embodiment, the substituents shown in the following Group G21:

Group G21

$C_{1-6}$ alkyl which may be substituted with the same or different 1 to 5 halogen(s); —O—($C_{1-6}$ alkyl which may be substituted with the same or different 1 to 5 substituent(s) selected from the group consisting of halogen and —O—($C_{1-6}$ alkyl)); an —O-saturated hetero ring; halogen; —N($C_{1-6}$ alkyl)$_2$; and cyclic amino;

in further still another embodiment, the substituents shown in the following Group G22:

Group G22

$C_{1-6}$ alkyl which may be substituted with the same or different 1 to 5 halogen(s); —O—($C_{1-6}$ alkyl which may be substituted with the same or different 1 to 5 substituent(s) selected from the group consisting of halogen and —O—($C_{1-6}$ alkyl)); halogen; and —N($C_{1-6}$ alkyl)$_2$;

in further still another embodiment, the substituents shown in the following Group G23:

Group G23

$C_{1-6}$ alkyl which may be substituted with the same or different 1 to 5 halogen(s); —O—($C_{1-6}$ alkyl which may be substituted with the same or different 1 to 5 halogen(s)); halogen; and —N($C_{1-6}$ alkyl)$_2$;

in further still another embodiment, the substituents shown in the following Group G24:

Group G24

$C_{1-6}$ alkyl which may be substituted with the same or different 1 to 5 halogen(s); —O—($C_{1-6}$ alkyl); and halogen;

in further still another embodiment, the substituents shown in the following Group G25:

Group G25

$C_{1-6}$ alkyl which may be substituted with the same or different 1 to 5 halogen(s); and —O—($C_{1-6}$ alkyl); and in further still another embodiment, trifluoromethyl and methoxy.

The substituent acceptable for the "monocyclic aromatic hetero ring which may be substituted" and "bicyclic aromatic hetero ring which may be substituted" in $R^2$ is, in a certain embodiment, the substituents shown in (a) to (c), (f), (g) and (m) to (o) in the Group G;

in another embodiment, the substituents shown in the following Group G3:

Group G3

$C_{1-6}$ alkyl which may be substituted with the same or different 1 to 5 halogen(s); —O—($C_{1-6}$ alkyl which may be substituted with the same or different 1 to 5 halogen(s)); halogen; —N($C_{1-6}$ alkyl)$_2$; —NH($C_{1-6}$ alkyl); —NH$_2$; and cyclic amino;

in still another embodiment, the substituents shown in the following Group G31:

Group G31

$C_{1-6}$ alkyl which may be substituted with the same or different 1 to 5 halogen(s); —O—($C_{1-6}$ alkyl which may be substituted with the same or different 1 to 5 halogen(s)); and halogen;

in further still another embodiment, the substituents shown in the following Group G32:

Group G32

$C_{1-6}$ alkyl which may be substituted with the same or different 1 to 5 halogen(s); and halogen;

in further still another embodiment, halogen; and in further still another embodiment, chloro.

Certain embodiments of the compound of the formula (I) or a salt thereof are shown below.

(1) The compound or a salt thereof, in which $R^1$ is cyclic amino which may be substituted with 1 to 5 substituent(s) selected from the Group G and oxo, or $R^1$ is —N(—$R^{11}$)(—$R^{12}$);

in another embodiment, the compound or a salt thereof, in which $R^1$ is cyclic amino selected from the group consisting of pyrrolidin-1-yl, piperidin-1-yl, azetidin-1-yl, and morpholin-4-yl, or —N(—$R^{11}$)(—$R^{12}$), and the cyclic amino may be substituted with the same or different 1 to 3 substituent(s) selected from the Group G1, $R^{11}$ is $C_{1-6}$ alkyl, and $R^{12}$ is $C_{1-6}$ alkyl which may be substituted with —O—($C_{1-6}$ alkyl), or $C_{3-8}$ cycloalkyl which may be substituted with $C_{1-6}$ alkyl substituted with —O—($C_{1-6}$ alkyl);

in still another embodiment, the compound or a salt thereof, in which $R^1$ is cyclic amino selected from the group consisting of pyrrolidin-1-yl, piperidin-1-yl, azetidin-1-yl, and morpholin-4-yl, or —N(—$R^{11}$)(— $R^{12}$), and the cyclic amino may be substituted with $C_{1-6}$ alkyl which may be substituted with the same or different 1 to 3 substituent(s) selected from the group consisting of —O—($C_{1-6}$ alkyl) and halogen, $R^{11}$ is $C_{1-6}$ alkyl, and $R^{12}$ is $C_{1-6}$ alkyl which may be substituted with —O—($C_{1-6}$ alkyl); and in further still another embodiment, the compound or a salt thereof, in which $R^1$ is cyclic amino selected from the group consisting of pyrrolidin-1-yl and piperidin-1-yl, or —N(—$R^{11}$)(—$R^{12}$), and the cyclic amino may be substituted with $C_{1-6}$ alkyl which may be substituted with the same or different 1 to 3 substituent(s) selected from the group consisting of —O—($C_{1-6}$ alkyl) and halogen, $R^{11}$ is $C_{1-6}$ alkyl, and $R^{12}$ is $C_{1-6}$ alkyl which may be substituted with —O—($C_{1-6}$ alkyl).

(1-1) The compound or a salt thereof, in which $R^1$ is cyclic amino which may be substituted with the same or different 1 to 5 substituent(s) selected from the Group G and oxo;

in another embodiment, the compound or a salt thereof, in which $R^1$ is cyclic amino which may be substituted with the same or different 1 to 3 substituent(s) selected from the Group G1;

in still another embodiment, the compound or a salt thereof, in which $R^1$ is cyclic amino selected from the group consisting of pyrrolidin-1-yl, piperidin-1-yl, azetidin-1-yl, and morpholin-4-yl, and the cyclic amino may be substituted with the same or different 1 to 3 substituent(s) selected from the Group G;

in further still another embodiment, the compound or a salt thereof, in which $R^1$ is cyclic amino selected from the group consisting of pyrrolidin-1-yl, piperidin-1-yl, azetidin-1-yl, and morpholin-4-yl, and the cyclic amino may be substituted with the same or different 1 to 3 substituent(s) selected from the Group G1;

in further still another embodiment, the compound or a salt thereof, in which $R^1$ is cyclic amino selected from the group consisting of pyrrolidin-1-yl, piperidin-1-yl, azetidin-1-yl, and morpholin-4-yl, and the cyclic amino may be substituted with $C_{1-6}$ alkyl which may be substituted with the same or different 1 to 3 substituent(s) selected from the group consisting of —O—($C_{1-6}$ alkyl) and halogen;

in further still another embodiment, the compound or a salt thereof, in which $R^1$ is cyclic amino selected from the group consisting of pyrrolidin-1-yl and piperidin-1-yl, and the cyclic amino is substituted with $C_{1-6}$ alkyl which may be substituted with the same or different 1 to 3 substituent(s) selected from the group consisting of —O—($C_{1-6}$ alkyl) and halogen;

in further still another embodiment, the compound or a salt thereof, in which $R^1$ is cyclic amino selected from the group consisting of pyrrolidin-1-yl and piperidin-1-yl, and the cyclic amino is substituted with $C_{1-6}$ alkyl which may be substituted with the same or different 1 to 3 —O—($C_{1-6}$ alkyl) group(s);

in further still another embodiment, the compound or a salt thereof, in which $R^1$ is cyclic amino selected from the group consisting of pyrrolidin-1-yl and piperidin-1-yl, and the cyclic amino is substituted with $C_{1-6}$ alkyl; and in further still another embodiment, the compound or a salt thereof, in which $R^1$ is cyclic amino selected from the group consisting of pyrrolidin-1-yl and piperidin-1-yl, and the cyclic amino is substituted with the same or different 1 to 3 substituent(s) selected from the group consisting of methyl and ethyl.

(1-2) The compound or a salt thereof, in which $R^1$ is —N(—$R^{11}$)(—$R^{12}$) and $R^{11}$ is methyl, ethyl, n-propyl, or isobutyl.

(1-3) The compound or a salt thereof, in which $R^1$ is —N(—$R^{11}$)(—$R^{12}$), and $R^{12}$ is $C_{1-6}$ alkyl which may be substituted with —O—($C_{1-6}$ alkyl), or $C_{3-8}$ cycloalkyl which may be substituted with $C_{1-6}$ alkyl substituted with —O—($C_{1-6}$ alkyl);

in another embodiment, the compound or a salt thereof, in which $R^1$ is —N(—$R^{11}$)(—$R^{12}$) and $R^{12}$ is $C_{1-6}$ alkyl substituted with —O—($C_{1-6}$ alkyl); and in still another embodiment, the compound or a salt thereof, in which $R^1$ is —N(—$R^{11}$)(—$R^{12}$) and $R^{12}$ is 2-methoxyethyl.

(1-4) The compound or a salt thereof, which is any combination of the embodiments described in (1-2) and (1-3) above.

(2) The compound or a salt thereof, in which $R^2$ is aryl which may be substituted with the same or different 1 to 5 substituent(s) selected from the Group G, a monocyclic aromatic hetero ring which may be substituted with the same or different 1 to 5 substituent(s) selected from the Group G, or a bicyclic aromatic hetero ring which may be substituted with the same or different 1 to 5 substituent(s) selected from the Group G;

in another embodiment, the compound or a salt thereof, in which $R^2$ is phenyl which may be substituted with the same or different 1 to 5 substituent(s) selected from the Group G, thienyl which may be substituted with the same or different 1 to 3 substituent(s) selected from the Group G, thiazolyl which may be substituted with the same or different 1 to 2 substituent(s) selected from the Group G, or 2,3-dihydro-1-benzofuranyl which may be substituted with the same or different 1 to 5 substituent(s) selected from the Group G;

in still another embodiment, the compound or a salt thereof, in which $R^2$ is phenyl which may be substituted with the same or different 1 to 5 substituent(s) selected from the Group G2, thienyl which may be substituted with the same or different 1 to 3 substituent(s) selected from the Group G3, thiazolyl which may be substituted with the same or different 1 to 2 substituent(s) selected from the Group G3, or 2,3-dihydrobenzofuranyl which may be substituted with the same or different 1 to 5 substituent(s) selected from the Group G3;

in further still another embodiment, the compound or a salt thereof, in which $R^2$ is phenyl or thienyl, in which the phenyl may be substituted with the same or different 1 to 5 substituent(s) selected from the Group G21 and the thienyl may be substituted with the same or different 1 to 3 substituent(s) selected from the Group G32;

in further still another embodiment, the compound or a salt thereof, in which $R^2$ is phenyl or thienyl, in which the phenyl may be substituted with the same or different 1 to 5 substituent(s) selected from the Group G22 and the thienyl may be substituted with the same or different 1 to 3 halogen(s);

in further still another embodiment, the compound or a salt thereof, in which $R^2$ is phenyl or thienyl, in which the phenyl may be substituted with the same or different 1 to 3 substituent(s) selected from the Group G24 and the thienyl may be substituted with the same or different 1 to 3 halogen(s);

in further still another embodiment, the compound or a salt thereof, in which $R^2$ is phenyl or thienyl, in which the phenyl may be substituted with the same or different 1 to 3 substituent(s) selected from the Group G25 and the thienyl may be substituted with the same or different 1 to 3 halogen(s); and in further still another embodiment, the compound or a salt thereof, in which $R^2$ is phenyl or thienyl, in which the phenyl may be substituted with the same or different 1 to 2 substituent(s) selected from the group consisting of trifluoromethyl and methoxy, and the thienyl may be substituted with one chloro.

(2-1) The compound or a salt thereof, in which $R^2$ is phenyl which may be substituted with the same or different 1 to 5 substituent(s) selected from the Group G;

in another embodiment, the compound or a salt thereof, in which $R^2$ is phenyl which may be substituted with the same or different 1 to 5 substituent(s) selected from the Group G2;

in still another embodiment, the compound or a salt thereof, in which $R^2$ is phenyl which may be substituted with the same or different 1 to 5 substituent(s) selected from the Group G21;

in further still another embodiment, the compound or a salt thereof, in which $R^2$ is phenyl which may be substituted with the same or different 1 to 5 substituent(s) selected from the Group G22;

in further still another embodiment, the compound or a salt thereof, in which $R^2$ is phenyl which may be substituted with the same or different 1 to 5 substituent(s) selected from the Group G23;

in further still another embodiment, the compound or a salt thereof, in which $R^2$ is phenyl which may be substituted with the same or different 1 to 3 substituent(s) selected from the Group G24;

in further still another embodiment, the compound or a salt thereof, in which $R^2$ is phenyl which may be substituted with the same or different 1 to 3 substituent(s) selected from the Group G25; and in further still another embodiment, the compound or a salt thereof, in which $R^2$ is phenyl which may be substituted with the same or different 1 to 2 substituent(s) selected from the group consisting of trifluoromethyl and methoxy.

(2-2) The compound or a salt thereof, in which $R^2$ is thienyl which may be substituted with the same or different 1 to 3 substituent(s) selected from the Group G;

in another embodiment, the compound or a salt thereof, in which $R^2$ is thienyl which may be substituted with the same or different 1 to 3 substituent(s) selected from the Group G3;

in still another embodiment, the compound or a salt thereof, in which $R^2$ is thienyl which may be substituted with the same or different 1 to 3 substituent(s) selected from the Group G31;

in further still another embodiment, the compound or a salt thereof, in which $R^2$ is thienyl which may be substituted with the same or different 1 to 3 substituent(s) selected from the Group G32;

in further still another embodiment, the compound or a salt thereof, in which $R^2$ is thienyl which may be substituted with the same or different 1 to 3 halogen(s); and in further still another embodiment, the compound or a salt thereof, in which $R^2$ is thienyl which may be substituted with one chloro.

(3) The compound or a salt thereof, in which $R^3$ is —H, —OH, methoxy, or fluoro; in another embodiment, the compound or a salt thereof, in which $R^3$ is —H, —OH, or fluoro; and in further still another embodiment, the compound or a salt thereof, in which $R^3$ is —H.

(4) The compound or a salt thereof, which is a combination of any embodiment described in (1), (1-1), or (1-4) above and any embodiment described in (2), (2-1), or (2-2) above and any embodiment described in (3) above.

(4-1) The compound or a salt thereof, in which $R^1$ is cyclic amino selected from the group consisting of pyrrolidin-1-yl, piperidin-1-yl, azetidin-1-yl, and morpholin-4-yl, or —N(—$R^{11}$)(—$R^{12}$), and the cyclic amino may be substituted with the same or different 1 to 3 substituent(s) selected from the Group G1, $R^{11}$ is $C_{1-6}$ alkyl, $R^{12}$ is $C_{1-6}$ alkyl which may be substituted with —O—($C_{1-6}$ alkyl), or $C_{3-8}$ cycloalkyl which may be substituted with $C_{1-6}$ alkyl substituted with —O—($C_{1-6}$ alkyl), and $R^2$ is phenyl which may be substituted with the same or different 1 to 5 substituent(s) selected from the Group G2, thienyl which may be substituted with the same or different 1 to 3 substituent(s) selected from the Group G3, thiazolyl which may be substituted with the same or different 1 to 2 substituent(s) selected from the Group G3, or 2,3-dihydrobenzofuranyl which may be substituted with the same or different 1 to 5 substituent(s) selected from the Group G3, and $R^3$ is —H, —OH, methoxy, or fluoro.

(4-2) The compound or a salt thereof as described in (4-1) above, in which $R^2$ is phenyl or thienyl, in which the phenyl may be substituted with the same or different 1 to 5 substituent(s) selected from the Group G21 and the thienyl may be substituted with the same or different 1 to 3 substituent(s) selected from the Group G32.

(4-3) The compound or a salt thereof as described in (4-2) above, in which $R^1$ is cyclic amino selected from the group consisting of pyrrolidin-1-yl and piperidin-1-yl, or —N(—$R^{11}$)(—$R^{12}$), and the cyclic amino may be substituted with $C_{1-6}$ alkyl which may be substituted with the same or different 1 to 3 substituent(s) selected from the group consisting of —O—($C_{1-6}$ alkyl) and halogen, $R^{12}$ is $C_{1-6}$ alkyl which may be substituted with —O—($C_{1-6}$ alkyl), $R^2$ is phenyl or thienyl, in which the phenyl may be substituted with the same or different 1 to 5 substituent(s) selected from the Group G22 and the thienyl may be substituted with the same or different 1 to 3 halogen(s), and $R^3$ is —H, —OH, or fluoro.

(4-4) The compound or a salt thereof as described in (4-3) above, in which $R^1$ is cyclic amino selected from the group consisting of pyrrolidin-1-yl and piperidin-1-yl, and the cyclic amino is substituted with $C_{1-6}$ alkyl which may be substituted with the same or different 1 to 3 —O—($C_{1-6}$ alkyl) group(s), and $R^2$ is phenyl or thienyl, in which the phenyl may be substituted with the same or different 1 to 3 substituent(s) selected from the Group G24 and the thienyl may be substituted with the same or different 1 to 3 halogen(s), and $R^3$ is —H.

(4-5) The compound or a salt thereof as described in (4-4) above, in which $R^1$ is cyclic amino selected from the group consisting of pyrrolidin-1-yl and piperidin-1-yl, and the cyclic amino is substituted with $C_{1-6}$ alkyl, and $R^2$ is phenyl or thienyl, in which the phenyl may be substituted with the same or different 1 to 3 substituent(s) selected from the Group G25 and the thienyl may be substituted with the same or different 1 to 3 halogen(s).

(4-6) The compound or a salt thereof as described in (4-5) above, in which $R^1$ is cyclic amino selected from the group consisting of pyrrolidin-1-yl and piperidin-1-yl, and the cyclic amino is substituted with the same or different 1 to 3 substituent(s) selected from the group consisting of methyl and ethyl, and $R^2$ is phenyl or thienyl, in which the phenyl may be substituted with the same or different 1 to 2 substituent(s) selected from the group consisting of trifluoromethyl and methoxy, and the thienyl may be substituted with one chloro.

(4-7) The compound or a salt thereof as described in (4-6) above, in which $R^2$ is phenyl which may be substituted with the same or different 1 to 2 substituent(s) selected from the group consisting of trifluoromethyl and methoxy.

(4-8) The compound or a salt thereof as described in (4-6) above, in which $R^2$ is thienyl which may be substituted with one chloro.

(4-9) The compound or a salt thereof, in which $R^1$ is cyclic amino which may be substituted with the same or different 1 to 5 substituent(s) selected from the Group G and oxo, $R^2$ is phenyl which may be substituted with the same or different 1 to 5 substituent(s) selected from the Group G, thienyl which may be substituted with the same or different 1 to 3 substituent(s) selected from the Group G, thiazolyl which may be substituted with the same or different 1 to 2 substituent(s) selected from the Group G, or 2,3-dihydro-1-benzofuranyl which may be substituted with the same or different 1 to 5 substituent(s) selected from the Group G, and $R^3$ is —H, —OH, methoxy, or fluoro.

(4-10) The compound or a salt thereof as described in (4-9) above, in which $R^2$ is phenyl which may be substituted with 1 to 5 substituent(s) selected from the Group G (4-11) The compound or a salt thereof as described in (4-9) above, in which $R^2$ is thienyl which may be substituted with 1 to 3 substituent(s) selected from the Group G.

(4-12) The compound or a salt thereof as described in (4-10) above, in which $R^1$ is cyclic amino selected from the group consisting of pyrrolidin-1-yl and piperidin-1-yl, and the cyclic amino is substituted with $C_{1-6}$ alkyl which may be substituted with the same or different 1 to 3 substituent(s) selected from the group consisting of —O—($C_{1-6}$ alkyl) and halogen, $R^2$ is phenyl which may be substituted with the same or different 1 to 5 substituent(s) selected from the Group G23, and $R^3$ is —H.

Specific examples of the compound included in the present invention include the following compounds or salts thereof:

1-{5-[(5-{[(2R)-2-ethylpyrrolidin-1-yl]methyl}-4-[4-propoxy-3-(trifluoromethyl)phenyl]-1,3-thiazol-2-yl)carbamoyl]pyrazin-2-yl}piperidine-4-carboxylic acid, 1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid, 1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylic acid, 1-{5-[(4-[4-isopropoxy-3-(trifluoromethyl)phenyl]-5-{[(2R)-2-propylpyrrolidin-1-yl]methyl}-1,3-thiazol-2-yl)carbamoyl]pyrazin-2-yl}piperidine-4-carboxylic acid, 1-(5-{[4-(3-chloro-5-fluoro-4-methoxyphenyl)-5-{[(2S)-2-(ethoxymethyl)pyrrolidin-1-yl]methyl}-1,3-thiazol-2-yl]carbamoyl}pyrazin-2-yl)piperidine-4-carboxylic acid, 1-{5-[(5-{[(2S)-2-(ethoxymethyl)pyrrolidin-1-yl]methyl}-4-[3-fluoro-4-methoxy-5-(trifluoromethyl)phenyl]-1,3-thiazol-2-yl)carbamoyl]pyrazin-2-yl}piperidine-4-carboxylic acid, 1-(5-{[4-(3,5-dichloro-4-methoxyphenyl)-5-{[(2R)-2-methylpyrrolidin-1-yl]methyl}-1,3-thiazol-2-yl]carbamoyl}pyrazin-2-yl)piperidine-4-carboxylic acid, 1-{5-[(5-{[(2R)-2-ethylpyrrolidin-1-yl]methyl}-4-[3-fluoro-5-(trifluoromethyl)phenyl]-1,3-thiazol-2-yl)carbamoyl]pyrazin-2-yl}piperidine-4-carboxylic acid, 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylic acid, 1-{5-[(4-[4-methoxy-3-(trifluoromethyl)phenyl]-5-{[(2R)-2-propylpyrrolidin-1-yl]methyl}-1,3-thiazol-2-yl)carbamoyl]pyrazin-2-yl}piperidine-4-carboxylic acid,
1-[5-({5-[(2-isopropylpyrrolidin-1-yl)methyl]-4-[4-methoxy-3-(trifluoromethyl)phenyl]-1,3-thiazol-2-yl}carbamoyl)pyrazin-2-yl]piperidine-4-carboxylic acid,
1-(5-{[4-(4-chloro-2-thienyl)-5-{[(2R)-2-ethylpyrrolidin-1-yl]methyl}-1,3-thiazol-2-yl]carbamoyl}pyrazin-2-yl)piperidine-4-carboxylic acid, and
1-{5-[(4-[4-ethoxy-3-(trifluoromethyl)phenyl]-5-{[(2R)-2-methylpyrrolidin-1-yl]methyl}-1,3-thiazol-2-yl)carbamoyl]pyrazin-2-yl}piperidine-4-carboxylic acid.

In another embodiment, specific examples of the compound included in the present invention include the following compounds or salts thereof:
1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid,
1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylic acid,
1-{5-[(5-{[(2R)-2-ethylpyrrolidin-1-yl]methyl}-4-[3-fluoro-5-(trifluoromethyl)phenyl]-1,3-thiazol-2-yl)carbamoyl]pyrazin-2-yl}piperidine-4-carboxylic acid, and
1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylic acid.

The compound of the formula (I) may exist in the form of tautomers or geometrical isomers depending on the kind of substituents. In the present specification, the compound of the formula (I) shall be described in only one isomer form, yet the present invention includes any other isomers, in their isolated form, or as mixtures thereof.

In addition, the compound of the formula (I) may have asymmetric carbon atoms or axial asymmetries in some cases, and therefore, optical isomers may exist based thereon. The present invention includes isolated forms of optical isomers of the compound of the formula (I) or any mixture thereof.

Moreover, the present invention also includes a pharmaceutically acceptable prodrug of the compound of the formula (I). The pharmaceutically acceptable prodrug is a compound having a group that can be converted into an amino group, a hydroxyl group, a carboxyl group, or the like through solvolysis or under physiological conditions. Examples of the group forming the prodrug include the groups described in Prog. Med., 5, 2157-2161 (1985) and "Pharmaceutical Research and Development" (Hirokawa Publishing Company, 1990), Vol. 7, Molecular Design, 163-198.

Moreover, the salt of the compound of the formula (I) is a pharmaceutically acceptable salt of the compound of the formula (I) and may form an acid addition salt or a salt with a base depending on the kind of substituents. Specific examples thereof include acid addition salts with inorganic acids such as hydrochloric acid, hydrobromic acid, hydroiodic acid, sulfuric acid, nitric acid, and phosphoric acid, and with organic acids such as formic acid, acetic acid, propionic acid, oxalic acid, malonic acid, succinic acid, fumaric acid, maleic acid, lactic acid, malic acid, mandelic acid, tartaric acid, dibenzoyltartaric acid, ditoluoyltartaric acid, citric acid, methanesulfonic acid, ethanesulfonic acid, benzenesulfonic acid, p-toluenesulfonic acid, aspartic acid, and glutamic acid, and salts with inorganic bases such as sodium, potassium, magnesium, calcium, and aluminum, or organic bases such as methylamine, ethylamine, ethanolamine, lysine, and ornithine, salts with various amino acids or amino acid derivatives such as acetylleucine, ammonium salts, and the like.

Furthermore, the present invention also includes various hydrates or solvates, and polymorphic crystalline substances of the compound of the formula (I) or a salt thereof. In addition, the present invention also includes compounds labeled with various radioactive or non-radioactive isotopes.

(Preparation Methods)

The compound of the formula (I) and salts thereof can be prepared using the characteristics based on the basic structure or the type of substituents thereof and by applying various known synthesis methods. During the preparation, replacing the relevant functional group with a suitable protective group (a group that can be easily converted into the relevant functional group) at the stage from starting material to an intermediate may be effective depending on the type of the functional group in the production technology in some cases. The protective group for such a functional group may include, for example, the protective groups described in "Greene's Protective Groups in Organic Synthesis ($4^{th}$ edition, 2006)", P. G. M. Wuts and T. W. Greene, and one of these may be selected and used as necessary depending on the reaction conditions. In this kind of method, a desired compound can be obtained by introducing the protective group, by carrying out the reaction and by eliminating the protective group as necessary.

In addition, prodrugs of the compound of the formula (I) can be prepared by introducing a specific group or by carrying out the reaction using the obtained compound of the formula (I) at the stage from a starting material to an intermediate, just as in the case of the above-mentioned protective group. The reaction can be carried out using methods known to a person skilled in the art, such as ordinary esterification, amidation, dehydration, and the like.

Hereinbelow, representative preparation methods for the compound of the formula (I) will be described. Each production process may also be carried out with reference to the References appended in the present description. Further, the preparation methods of the present invention are not limited to the examples as shown below.

[Chem. 4]

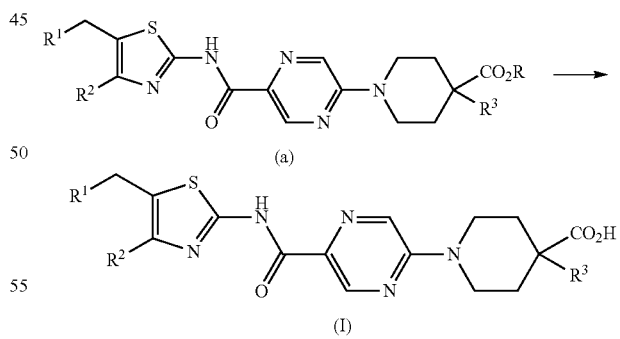

(in which R represents lower alkyl or benzyl, the same shall apply hereinafter.)

The present reaction is a method in which a compound of the formula (a) is deprotected to prepare the compound of the formula (I) which is the compound of the present invention.

The present reaction is carried out by using the compound of the formula (a) and a deprotecting reagent in equivalent amounts, or either thereof in an excess amount, and stirring the mixture in a solvent which is inert to the reaction or in the absence of a solvent, in a range from cooling to heating to reflux, usually for 0.1 hours to 5 days. Alternatively, in the case where R is benzyl, the present reaction may also be carried out by subjecting the compound of the formula (a) to a hydrogenation reaction, using a metal catalyst under a hydrogen atmosphere. Examples of the solvent herein used are not particularly limited, but include alcohols such as methanol, ethanol, n-propanol, or the like, dimethylformamide (DMF), tetrahydrofuran and the like. Further, a mixed solvent of the solvent with water may be suitable for the reaction in some cases. Examples of the deprotecting reagent are not particularly limited, but include bases such as an aqueous sodium hydroxide solution, an aqueous potassium hydroxide solution or the like, and acids such as hydrochloric acid, trifluoroacetic acid, or the like. In addition, examples of the metal catalyst that can be used for the hydrogenation condition include palladium-supported carbon, palladium hydroxide, and the like.

(Starting Material Synthesis 1-1)

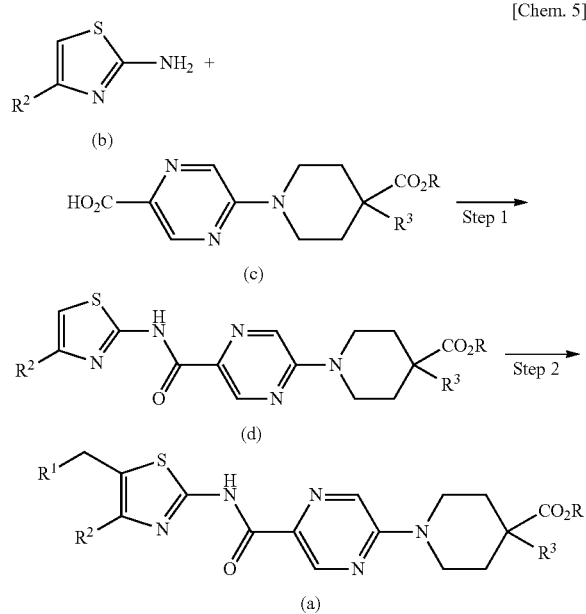

(Step 1)

The present step is a step in which a compound of the formula (b) and a compound of the formula (c) are subjected to an amidation reaction to obtain a compound of the formula (d).

In this reaction, the compound of the formula (b) and the compound of the formula (c) are used in equivalent amounts, or either thereof in an excess amount, and their mixture is stirred in a range from cooling to heating, preferably at a temperature from −20° C. to 150° C., usually for 0.1 hours to 5 days, in a solvent which is inert to the reaction, in the presence of a condensing reagent. Examples of the solvent herein used are not particularly limited, but include aromatic hydrocarbons such as benzene, toluene, xylene, or the like, halogenated hydrocarbons such as dichloromethane, 1,2-dichloroethane, chloroform, or the like, ethers such as diethyl ether, tetrahydrofuran, dioxane, dimethoxyethane, cyclopentylmethyl ether, or the like, N,N-dimethylformamide, dimethylsulfoxide (DMSO), ethyl acetate, acetonitrile, or water, and any mixture thereof. Examples of condensing reagent include, but are not limited to, 1-(3-dimethylaminopropyl)-3-ethylcarbodiimide, dicyclohexylcarbodiimide, 1,1'-carbonyldiimidazole, diphenylphosphoryl azide, phosphorous oxychloride, and O-(benzotriazol-1-yl)-N,N,N',N'-tetramethyluronium tetrafluoroborate. It may be preferable in some cases for the reaction to use an additive (for example, 1-hydroxybenzotriazole). It may be advantageous in some cases for smooth progress of the reaction to carry out the reaction in the presence of organic bases such as triethylamine, N,N-diisopropylethylamine, N-methylmorpholine, or the like, or inorganic bases such as potassium carbonate, sodium carbonate, potassium hydroxide, or the like. In addition, it may be advantageous in some cases for the smooth progress of the reaction to heat the reaction mixture under irradiation with microwaves.

Furthermore, it is also possible to use a method in which a carboxylic acid (c) is converted to a reactive derivative and afterward reacted with an amine (b). Examples of the reactive derivative of the carboxylic acid include acid halides that can be obtained by the reaction with a halogenating reagent such as phosphorus oxychloride, thionyl chloride, or the like, mixed acid anhydrides obtained by the reaction with isobutyl chloroformate, or the like, and active esters obtained by condensation with 1-hydroxybenzotriazole or the like. The reaction of these reactive derivatives with the compound (b) can be carried out in a range from cooling to heating, and preferably from −20° C. to 60° C., in a solvent which is inert to the reaction, such as halogenated hydrocarbons, aromatic hydrocarbons, ethers, and the like.

DOCUMENTS

"Organic Functional Group Preparations", S. R. Sandler and W. Karo, $2^{nd}$ edition, Vol. 1, Academic Press Inc., 1991

The Chemical Society of Japan, "Courses in Experimental Chemistry ($5^{th}$ edition)" Vol. 16 (2005) (Maruzen)

(Step 2)

The present step is a step in which an aminomethyl group is introduced into the 5-position of thiazole of a compound of the formula (d) using a Mannich reaction to prepare the compound of the formula (a). The method shown in Albertson, N. F.: Journal of American Chemistry 1948, 70, 669., or Bhargava, P. N.; Sharma, S. C.; Bulletin of the Chemical Society of Japan 1965, 38, 909., or a method analogous thereto can be employed.

(Starting Material Synthesis 1-2)

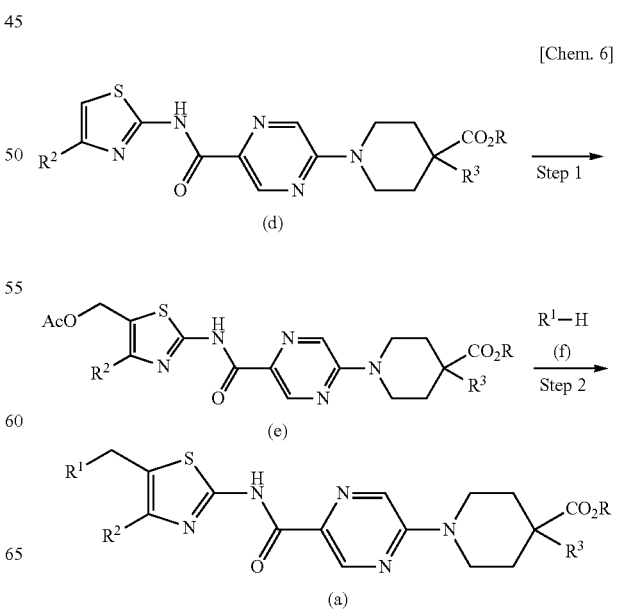

(Step 1)

The present step is a step in which an acetoxymethyl group is introduced into the 5-position of thiazole of a compound of the formula (d) to prepare a compound of the formula (e). The compound of the formula (d) is subjected to a reaction with an aqueous formaldehyde solution or paraformaldehyde in an acetic acid solvent, in a range from room temperature to heating, or in a range of room temperature to refluxing. Further, the reaction may also be carried out by adding acetic acid to a solvent which is inert to the reaction, such as halogenated hydrocarbons, aromatic hydrocarbons, ethers, or the like, instead of the acetic acid solvent. Further, the reaction may also be carried out by further adding acetic anhydride.

(Step 2)

The present step is a step in which under a basic condition, the compound of the formula (e) is subjected to a nucleophilic substitution reaction with a compound of the formula (f) to prepare the compound of the formula (a). The nucleophilic substitution reaction can be carried out by subjecting the compound of the formula (e) to a reaction with the compound of the formula (f) in an organic solvent which is inert to the reaction, such as halogenated hydrocarbons, aromatic hydrocarbons, ethers, esters, acetonitrile, DMF, DMSO, or the like, in the presence of organic bases such as triethylamine, diisopropylethylamine, or the like and/or inorganic bases such as potassium carbonate, sodium carbonate, cesium carbonate, sodium hydrogen carbonate, or the like. Further, in order to accelerate the reaction, a catalyst such as dimethylaminopyridine may also be added. In addition, instead of the organic bases and/or inorganic bases, the compound of the formula (f) may be used in an excess amount. The reaction can be carried out in a range from cooling to room temperature, in a range from room temperature to heating, or in a range from room temperature to refluxing.

(Starting Material Synthesis 2)

[Chem. 7]

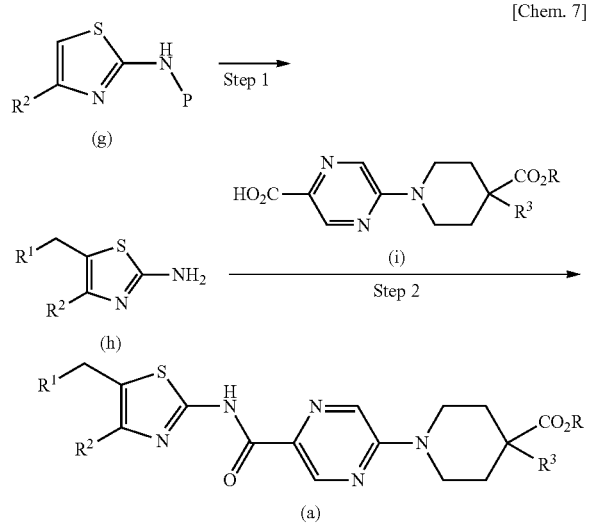

(in which P represents a protective group, for example, an acetyl group.)

(Step 1)

The present step is a step in which the compound of formula (g) is subjected to a deprotection reaction after the Mannich reaction to prepare a compound of the formula (h). The Mannich reaction is the same as Step 2 of Starting Material Synthesis 1-1. The subsequent deprotection of P which is a protective group of the amino group can be carried out with reference to "Protective Groups in Organic Synthesis", Greene and Wuts, 4$^{th}$ edition, John Wiley & Sons Inc, 2006 as described above.

(Step 2)

The present step is a step in which the compound of the formula (h) and a compound of the formula (i) are subjected to an amidation reaction to prepare the compound of the formula (a). The reaction conditions are the same as in Step 1 of Starting Material Synthesis 1-1.

(Starting Material Synthesis 3)

[Chem. 8]

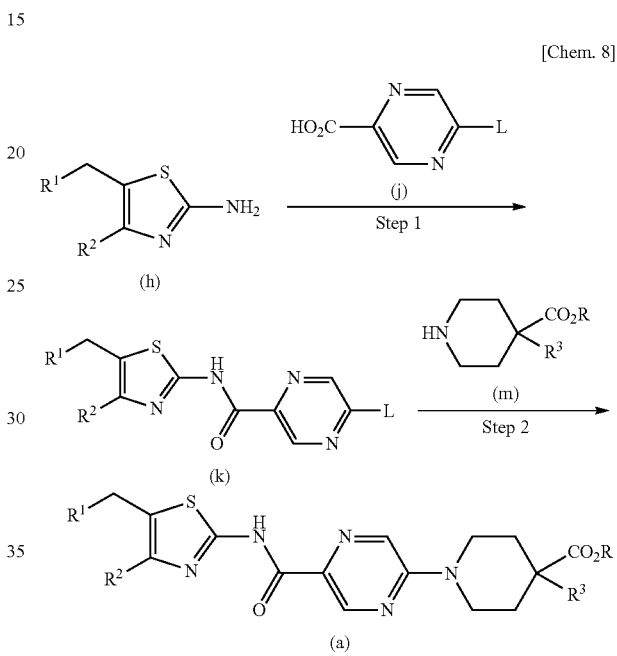

(in which L represents a leaving group, for example, chloro.).

(Step 1)

The present step is a method in which the compound of the formula (h) and a compound of the formula (j) are subjected to an amidation reaction to prepare a compound of the formula (k). The reaction conditions are the same as in Step 1 of Starting Material Synthesis 1-1.

(Step 2)

The present step is a step in which the compound of the formula (k) is reacted with a compound of the formula (m) to prepare the compound of the formula (a).

In this reaction, the compound (k) and a compound (m) are used in equivalent amounts, or either thereof in an excess amount, and their mixture is stirred in a range from cooling to heating to reflux, preferably at a temperature from 0° C. to 80° C., usually for 0.1 hours to 5 days, in a solvent which is inert to the reaction or in the absence of a solvent. Examples of the solvent herein used are not particularly limited, but include aromatic hydrocarbons such as benzene, toluene, xylene, or the like, ethers such as diethyl ether, tetrahydrofuran, dioxane, dimethoxyethane, or the like, halogenated hydrocarbons such as dichloromethane, 1,2-dichloroethane, chloroform, or the like, N,N-dimethylformamide, dimethylsulfoxide, ethyl acetate, acetonitrile, N-methylpyrrolidone and a mixture thereof. It may be advantageous in some cases for smooth progress of the reaction to carry out the reaction in the presence of organic bases such as triethylamine, N,N-diisopropylethylamine, N-methylmorpholine, or the like, or inorganic bases such as potassium carbonate, sodium carbonate, potassium hydroxide, or the like.

DOCUMENTS

"Organic Functional Group Preparations", S. R. Sandler and W. Karo, 2nd edition, Vol. 1, Academic Press Inc., 1991

The Chemical Society of Japan, "Courses in Experimental Chemistry (5th edition)" Vol. 14 (2005) (Maruzen)

The compounds of the formula (I) can be isolated and purified as free compounds, salts, hydrates, solvates, or crystal polymorph substances thereof. Salts of the compound of the formula (I) can be prepared by conventional salt forming reactions.

Isolation and purification are carried out by employing ordinary chemical operations such as extraction, fractional crystallization, and various types of fractional chromatography.

Various isomers can be prepared by selecting appropriate starting compounds or by separation using differences in physicochemical properties between the isomers. For example, optical isomers can be obtained by means of a general optical resolution method for racemic products (for example, fractional crystallization for inducing diastereomer salts with optically active bases or acids, and chromatography using a chiral column or the like), and further, the isomers can also be prepared from an appropriate optically active starting compound.

Pharmacological activities of the compound of the formula (I) were confirmed in the following tests.

Test Example 1

Evaluation of Muscarinic $M_3$ Receptor Positive Allosteric Modulator Activity a) Construction of Human Muscarinic $M_3$ Receptor Expression Vector A human muscarinic $M_3$ receptor gene (GenBank Accession No. NM_000740.2) was introduced into an expression vector pcDNA3.1™ (Life Technologies).

b) Construction of Cell Stably Expressing Human Muscarinic $M_3$ Receptor

The human muscarinic $M_3$ receptor expression vector was introduced into a CHO-K1 cell (ATCC No. CCL-61). The introduction was carried out by using a Lipofectoamine (registered trademark) 2000 reagent (Life Technologies) which is a gene introduction reagent, according to instructions attached. The cells were cultured in an alpha Modified Eagle Minimum Essential Medium (α-MEM) containing 2 mM glutamic acid, 10% fetal bovine serum, and 2.0 mg/mL Geneticin (registered trademark) (Life Technologies) for 4 weeks to acquire a drug-resistant clone.

c) Measurement of Intracellular $Ca^{2+}$ Concentration

On the day before the experiment, the cells obtained in b) above were suspended in an α-MEM containing 2 mM glutamic acid, 10% fetal bovine serum, and 0.2 mg/mL Geneticin (registered trademark), dispensed into a 384-well plate (Lot number 355962, BD Biosciences) to 1.2 to $1.5 \times 10^4$ cells/well, and cultured at 37° C. and 5% $CO_2$ overnight. The culture medium was replaced with a loading buffer (Assay Buffer (Hanks Balanced Salt Solution (HBSS), 1 g/L BSA, 20 mM HEPES (pH 7.5), and 2.5 mM Probenecid) containing 3.1 μM Fluo 4-AM (Dojindo Laboratories)), and left at room temperature for about 2 hours. Thereafter, the cells were washed with a plate washer ELx405™ (BIO-TEK Instruments) in which the assay buffer had been set, and placed in an intracellular $Ca^{2+}$ concentration measuring system (FLIPR$^{tetra}$ (registered trademark), Molecular Devices). A test substance (final concentration of 1 μM or 10 μM) and carbachol (Sigma, final concentration of 0.0024 nM to 100 μM) each of which had been dissolved in the assay buffer in advance were placed in a FLIPR$^{tetra}$ (registered trademark). In the device, the test substances were added to the cells, then carbachol was added to the cells about 5 minutes after adding the test substances, and increases in the intracellular $Ca^{2+}$ concentration by carbachol were measured (excitation wavelength of 470 nm to 495 nm and fluorescent wavelength of 515 nm to 575 nm).

For the activity of the muscarinic $M_3$ receptor positive allosteric modulator, a shift toward a lower concentration side of a carbachol concentration-response curve by the test substance was used as an index. That is, the minimum value of the carbachol response and the maximum value of the carbachol response from the concentration-response curve of carbachol were set to 0% and 100%, respectively. By a logistic regression method, the concentration of carbachol showing a 50% response was calculated as an $EC_{50}$ value, and the activity was determined by dividing the $EC_{50}$ value of carbachol in the absence of the test substance by the $EC_{50}$ value in the presence of the test substance. For example, when the $EC_{50}$ value of carbachol in the absence of the test substance is 0.1 μM and the $EC_{50}$ value of carbachol in the presence of the test substance is 0.01 μM, the value becomes 10, indicating that the test substance has a 10-fold shift toward a lower concentration side in the carbachol concentration response curve. In the table after described, the values in the case where the test substances were added at a final concentration of 10 μM are shown in the section of 10 μM (-fold shift), and the values in the case where the test substances were added at a final concentration of 1 μM are shown in the section of 1 μM (-fold shift).

Test Example 2

Evaluation of Human c-Mpl-Introduced Ba/F3 Cell Proliferative Activity

The human c-Mpl-introduced Ba/F3 cell proliferative activity was measured by the following method.

As a positive control, 1-(5-{[4-(4-chloro-2-thienyl)-5-{[(2R)-2-methylpyrrolidin-1-yl]methyl}-1,3-thiazol-2-yl]carbamoyl}-3-fluoropyridin-2-yl)piperidine-4-carboxylic acid hydrochloride, which is disclosed as Example 315 in Patent Document 1 and represented by the formula A1, was used. It is known that the compound has a good human c-Mpl-introduced Ba/F3 cell proliferative activity as disclosed in Table 1 of Patent Document 1.

a) Construction of Human c-Mpl Receptor Expression Vector

A human c-mpl receptor gene (GenBank Accession No. M90102.1) was introduced into an expression vector pEF-BOS (Nucleic Acids Res. 18, 5322, 1990).

b) Construction of Cell Stably Expressing Human c-Mpl Receptor

A human c-Mpl receptor expression vector was introduced into a Ba/F3 cell (RIKEN BRC: RCB0805). For the introduction, an electroporation method was used. pEF-BOS-c-mpl (10 μg), pSV2bsr (1 μg, Kaken Pharmaceutical Co., Ltd.) and $1 \times 10^7$ Ba/F3 cells were put into a cuvette having a gap width of 0.4 cm, and electroporated under the conditions of 1.5 kV (25 μF) by a Gene Pulser (registered trademark) (BioRad). The cells were cultured in an RPMI-1640 culture medium containing 0.5% WEHI conditioned media (BD Biosciences) and 10% fetal bovine serum for 3 days, and then cultured in an RPMI-1640 culture medium, to which 10 μg/mL blasticidin had been further added, for 30 days to acquire a drug-resistant clone.

c) Measurement of Cell Proliferative Activity

The cells obtained in b) above was cultured in an RPMI-1640 culture medium containing 0.5% WEHI conditioned media, 10% fetal bovine serum, and used. On the day before the experiment, test substances (final concentration of 100 nM to 10 μM) which had been dissolved in a culture medium for assay (RPMI-1640 culture medium containing 10% fetal bovine serum) were added to a 384-well plate (Lot No. 781185, Greiner Bio-One). The cells in the culture medium that had been replaced with a culture medium for assay were dispensed into a 384-well plate, to which the test substances had been added in advance, to $1 \times 10^4$ cells/well, and cultured at 37° C. and 5% $CO_2$ overnight. On the experiment day, a solution of a Cell Counting Kit (Dojindo Laboratories) was added to each well of the 384-well plate and cultured at 37° C. and 5% $CO_2$ for about 5 hours. Thereafter, the absorbance (absorption wavelength of 450 nm) of each well was measured using Safire$^2$™ (TECAN) and used as the index of the number of cells. Further, as a negative control, a well in which the test substance had been not added was prepared.

The absorbance of the well without the test substance was set to 0%, and the absorbance in the case where the positive control was added at a final concentration of 1 μM was set to 100%. From the absorbance in the case where the test substance had been added, a cell proliferation rate (%) was calculated. From the obtained results, the test substance concentration showing 30% proliferation was calculated as an $EC_{30}$ value by a logistic regression method.

The muscarinic $M_3$ receptor positive allosteric modulator activity (-fold shift) and the human c-Mpl-introduced Ba/F3 cell proliferative activity ($EC_{30}$ value, nM) of several Example compounds of the present invention are shown in combination in Table 1. Further, Ex represents Example No. as denoted after (this shall apply hereinafter).

TABLE 1

| | Test Example 1 | | |
|---|---|---|---|
| Ex. | 10 μM (-fold shift) | 1 μM (-fold shift) | Test Example 2 $EC_{30}$ (nM) |
| 1 | 187 | 11 | >10000 |
| 2 | 253 | 12 | >10000 |
| 3 | 260 | 19 | 4800 |
| 4 | 186 | 31 | 350 |
| 11 | 91 | 15 | >10000 |
| 19 | 151 | 10 | >10000 |
| 20 | 361 | 15 | >10000 |
| 21 | 116 | 14 | >10000 |
| 27 | 340 | 26 | >10000 |
| 38 | 126 | 14 | >10000 |
| 69 | 114 | 10 | >10000 |
| 84 | 184 | 17 | >10000 |
| 92 | 131 | 11 | >10000 |
| 115 | 245 | 10 | >10000 |
| 125 | 128 | 20 | >10000 |
| 128 | 533 | 64 | 8400 |
| 129 | 464 | 109 | 770 |
| 133 | 209 | 36 | 1100 |
| 142 | 110 | 15 | 380 |
| 146 | 201 | 18 | 820 |
| 150 | 213 | 17 | >10000 |
| 152 | 251 | 24 | 580 |

TABLE 1-continued

| | Test Example 1 | | |
|---|---|---|---|
| Ex. | 10 μM (-fold shift) | 1 μM (-fold shift) | Test Example 2 $EC_{30}$ (nM) |
| 156 | 269 | 19 | >10000 |
| 158 | 128 | 9 | >10000 |
| 179 | 373 | 34 | >10000 |
| 188 | 246 | 12 | >10000 |
| 196 | 186 | 38 | 380 |
| 197 | 100 | 20 | 1800 |
| 200 | 97 | 10 | >10000 |
| 203 | 203 | 16 | >10000 |
| 204 | 207 | 25 | >10000 |

In Test Example 1, for many Example compounds which had been subjected to the present test, the carbachol concentration response curve had an approximately 100-fold or more shift toward a lower concentration side when the compounds were added at a concentration of 10 μM, and the carbachol concentration response curve had an approximately 10-fold or more shift toward a lower concentration side when the compounds were added at a concentration of 1 μM. Further, it was confirmed that several Example compounds alone did not cause a change in the intracellular $Ca^{2+}$ concentrations, therefore it was confirmed that these compounds do not have a muscarinic $M_3$ receptor agonistic activity.

And, in Test Example 2, it was confirmed that a number of Example compounds which had been subjected to the present test had no or weak human c-Mpl-introduced Ba/F3 cell proliferative activity. In a certain embodiment, the compound of the present invention is a compound having an $EC_{30}$ value of the human c-Mpl-introduced Ba/F3 cell proliferative activity of 0.3 μM or more, preferably 1 μM or more, and further preferably 10 μM or more.

Test Example 3

Effects on Transmural Electrical Field Stimulation-Induced Contraction of Isolated Rat Bladder As an effect on the nerve stimulation-dependent bladder contraction in vitro, the effect of the Example compound of the present invention in the transmural electrical field stimulation-induced contraction of isolated rat bladder was measured by the following method. That is, from the bladder isolated from a Sprague-Dawley (SD) female rat (Japan SLC, Inc.), a longitudinal bladder strip having a width of about 2 mm and a length of about 10 mm was prepared. The prepared bladder strip was suspended in an organ bath filled with 10 mL of a Krebs-Henseleit solution. The Krebs-Henseleit solution was bubbled with 95% $O_2$ and 5% $CO_2$, and kept at 37° C. After stabilization at an initial tension of 1 g, contraction was induced twice with 60 mM KCl. The strip was washed with the Krebs-Henseleit solution and stabilized, and then contraction was induced with transmural electrical field stimulation at 20 V (stimulation frequency of 8 Hz, pulse width of 0.3 msec, and stimulation time of 10 seconds) by an electrical stimulation device (Nihon Kohden Corporation). At an interval of 2 minutes, transmural electrical field stimulation was repeated and the voltage was adjusted to make the contractile amplitude about 50% of the contractile response by 20 V. After stabilization of the contraction by the transmural electrical field stimulation, 10 μL of the test substance (final concentrations of 3 μM, 10

μM, and 30 μM), which had been dissolved in 100% dimethylsulfoxide in advance was added. The test substance was cumulatively administered at the next concentration after the contractile response at a lower concentration had been stabilized. The responses were put into a personal computer through PowerLab (registered trademark) (AD Instruments), and analyzed with LabChart (registered trademark) (AD Instruments). The area under the response of each contractile response (area under curve, AUC) was calculated and the value before the treatment with the test substance was set to 100%. Based on this, the enhancement rate of the isolated bladder contraction (% of pre) after the treatment with the test substance was calculated.

The enhancement rates of the isolated bladder contraction due to several 10 μM Example compounds which are the compounds of the formula (I) are shown in Table 2.

And, all of the Example compounds which had been subjected to the present test did not cause contraction in the absence of the electrical field stimulation, therefore it was confirmed that the compound alone did not exhibit a bladder contractile effect.

TABLE 2

| Ex. | Enhancement rate of isolated bladder contraction (% of pre) |
|---|---|
| 1 | 132 |
| 4 | 180 |
| 19 | 124 |
| 69 | 152 |
| 84 | 140 |
| 92 | 132 |
| 115 | 121 |
| 156 | 135 |
| 158 | 125 |
| 179 | 120 |
| 188 | 128 |
| 196 | 125 |

As seen from above, it was confirmed that the Example compounds which had been subjected to the present test do not exhibit a contractile effect in the isolated rat bladder when used alone, and have an activity for enhancing the transmural electrical field stimulation-induced contraction.

Test Example 4

Effect on Pelvic Nerve Electrical Stimulation-Induced Elevation of Intravesical Pressure in Anesthetized Rats As an effect on the nerve stimulation-dependent bladder contraction in vivo, the effect of the Example compound of the present invention in the pelvic nerve electrical stimulation-induced elevation of the intravesical pressure in rats was measured by the following method. That is, using SD female rats (Japan SLC, Inc.), the lower abdomen was incised in the midline under anesthesia with pentobarbital (50 mg/kg ip). The ureter on both sides was ligated and cut, and then a cannula for measuring the intravesical pressure (PE-50) was inserted into the bladder from the external urethral orifice and fixed by a clip. About 200 μL of physiological saline was injected through the cannula inserted into the bladder, the other side was then connected to a pressure transducer, and the intravesical pressure was measured. Under observation using a stereomicroscope, the pelvic nerve near the bladder was isolated and an electrode (Unique Medical) for nerve stimulation was placed. The abdominal cavity was filled with mineral oil (MP BIOMEDICALS). After the surgery, a stabilization period was applied, and an elevation of the intravesical pressure was induced by the electrical stimulation of the pelvic nerve (stimulation frequency of 8 Hz, pulse width of 0.3 msec, and stimulation time of 10 seconds) using an electrical stimulation device (Nihon Kohden Corporation). While adjusting the voltage, electrical stimulation was repeated at an interval of 2 minutes, and the voltage was adjusted to make the elevation of the intravesical pressure about 50% to 70% of that with stimulation at 10 V. Thereafter, the electrical stimulation at an interval of 10 minutes was repeated. After the elevation of the intravesical pressure by electrical stimulation was stabilized three times or more, the test substance (dose of 3 mg/kg) was administered at a volume of 1 mL/kg from a catheter placed in the vein and the effect of the test substance on the elevation of the intravesical pressure was measured for 1 hour. The test substance was dissolved in water containing 10% dimethylsulfoxide and 10% Cremophor.

The responses were put into a personal computer through PowerLab (registered trademark) (AD Instruments), and analyzed with LabChart (registered trademark). The AUC of each elevation of the intravesical pressure was calculated. The average value of three values before the treatment with the test substance was set to 100%, and the elevation rate of the intravesical pressure (% of pre) after the treatment with the test substance was calculated. The maximum effect during the one-hour period after the administration of the compound was considered as the effect of the test substance.

The elevation rates of the intravesical pressure (% of pre) when several Example compounds which are the compounds of the formula (I) were administered at 3 mg/kg are shown in Table 3.

TABLE 3

| Ex. | Elevation rate of intravesical pressure (% of pre) |
|---|---|
| 4 | 184 |
| 115 | 131 |
| 156 | 130 |

In addition, all of the Example compounds which had been evaluated in the present test did not cause an elevation of the intravesical pressure when electrical stimulation was not applied, therefore it was confirmed that the compound alone did not exhibit an elevating effect on the intravesical pressure.

As seen from above, it was confirmed that the Example compounds which are shown in Table 3 do not exhibit an elevating effect on the intravesical pressure when used alone, but have an enhancing effect on the pelvic nerve electrical stimulation-induced elevation of the intravesical pressure in the anesthetized rat.

As seen from the results of each test above, it was confirmed that the compound of the formula (I) has a muscarinic $M_3$ receptor positive allosteric modulator activity and enhances the bladder contraction in vitro in a nerve stimulation-dependent manner and enhances an elevation of the intravesical pressure in vivo in a nerve stimulation-dependent manner. Accordingly, the compound of the formula (I) can be used for preventing or treating bladder or urinary tract diseases, related to bladder contraction by a muscarinic $M_3$ receptor, in particular, voiding dysfunctions or storage dysfunctions in bladder or urinary tract diseases. For example, the compound of the formula (I) can be used for preventing or treating voiding dysfunctions or storage dysfunctions in underactive bladder, hypotonic bladder, acontractile bladder, detrusor underactivity, neurogenic bladder, urethral relaxation failure, detrusor-external urethral sphincter dyssynergia, overactive bladder, urinary frequency, nocturia, urinary incontinence, benign prostatic hyperplasia, interstitial cystitis, chronic prostatitis, urethral calculus, or the like. In particular, the compound of the formula (I) can be used for preventing or treating voiding dysfunctions or storage dysfunctions in underactive bladder, hypotonic bladder, acontractile bladder, detrusor underactivity, and neurogenic bladder.

Further, the compound of the formula (I) does not exhibit an agonistic effect on a muscarinic $M_3$ receptor when used alone, and has an effect on enhancing the nerve stimulation-dependent bladder contraction, thus avoiding the cholinergic side effects as reported in the existing drugs. Therefore, the compound of the formula (I) can be a therapeutic agent having superior safety.

Pharmaceutical compositions containing one or more kinds of the compound of the formula (I) or a salt thereof as an active ingredient can be prepared using excipients that are usually used in the art, that is, excipients for pharmaceutical preparation, carriers for pharmaceutical preparation, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, transdermal solutions, ointments, transdermal patches, transmucosal solutions, transmucosal patches, inhalers, and the like.

Solid compositions for oral administration are used in the form of tablets, powders, granules, or the like. In such solid compositions, one or more active ingredient(s) are mixed with at least one inactive excipient. In a conventional method, the composition may contain inactive additives, such as lubricants, disintegrating agents, stabilizers, or solubilization assisting agents. If necessary, tablets or pills may be coated with sugar or s gastric- or enteric-soluble substance films.

Liquid compositions for oral administration include pharmaceutically acceptable emulsions, solutions, suspensions, syrups, elixirs, or the like, and also include generally used inert diluents, for example, purified water or ethanol. In addition to the inert diluent, liquid compositions may also contain auxiliary agents, such as solubilization assisting agents, moistening agents, and suspending agents, sweeteners, flavors, aromatics, or antiseptics.

Injections for parenteral administration include sterile aqueous or non-aqueous solutions, suspensions, or emulsions. Aqueous solvents include, for example, distilled water for injection or physiological saline. Examples of non-aqueous solvents include alcohols such as ethanol. Such compositions may further contain tonicity agents, antiseptics, moistening agents, emulsifying agents, dispersing agents, stabilizers, or solubilization assisting agents. These are sterilized, for example, by filtration through bacteria retaining filter, blendings of bactericide, or irradiation. In addition, these can also be used by preparing sterile solid compositions, and dissolving or suspending in sterile water or sterile solvents for injection prior to use.

Agents for external use includes ointments, plasters, creams, jellies, poultices, sprays, lotions, and the like. The agents contain generally used ointment bases, lotion bases, aqueous or non-aqueous solutions, suspensions, emulsions, and the like.

As transmucosal agents such as inhalers, transnasal agents, and the like, those in the form of a solid, liquid, or semi-solid state are used, and can be prepared in accordance with conventionally known methods. For example, known excipients, and furthermore pH adjusting agents, antiseptics, surfactants, lubricants, stabilizers, thickening agents, or the like may be appropriately added thereto. For their administration, appropriate devices for inhalation or blowing can be used. For example, a compound may be administered alone or as a powder of formulated mixture, or as a solution or suspension in combination with pharmaceutically acceptable carriers, using a known device or sprayer, such as a measured administration inhalation device, and the like. Dry powder inhalers or the like may be for single or multiple administration use, and dry powder or powder-containing capsules may be used. Alternatively, these may be a pressurized aerosol spray which uses appropriate ejection agents, for example, a suitable gas such as chlorofluoroalkane, carbon dioxide, and the like.

For oral administration, a daily dose is generally from about 0.001 to 100 mg/kg, preferably from 0.1 to 30 mg/kg, and more preferably from 0.1 to 10 mg/kg, per body weight, administered in one portion or in 2 to 4 separate portions. In the case of intravenous administration, a daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. Doses are appropriately determined according to the individual according to the symptoms, age, gender, and the like.

Although varying depending on administration routes, formulations, administration sites, or the types of excipients or additives, the pharmaceutical composition of the present invention contains 0.01 to 100% by weight, and in a certain embodiment, 0.01 to 50% by weight of one or more kinds of the compound of the formula (I) or a salt thereof, which is an active ingredient.

The compound of the formula (I) can be used in combination with various agents for treating or preventing the diseases for which the compound of the formula (I) is considered to be effective, as described above. The combined preparation may be administered simultaneously, or separately and continuously, or at a desired time interval. The preparations to be administered simultaneously may be a mixture, or may be prepared individually.

EXAMPLES

Hereinbelow, the preparation methods for the compound of the formula (I) will be described in more detail with reference to Examples. The present invention is not limited to the compounds described in Examples as described below. Further, the production processes for the starting compounds will be described in Preparation Examples. Further, the preparation methods for the compound of the formula (I) are not limited to the preparation methods in specific Examples shown below, and the compound of the formula (I) can be prepared according to a combination of these preparation methods or methods apparent to those skilled in the art.

Further, in the present specification, nomenclature software such as ACD/Name (registered trademark, Advanced Chemistry Development, Inc.) may be used in some cases for the nomenclature of the compounds.

Moreover, the following abbreviations may be used in some cases in Examples, Preparation Examples, and Tables as described later.

PEx: Preparation Example number, Ex: Example number, PSyn: Preparation Example No. prepared by the same method, Syn: Example No. prepared by the same method, No.: Compound No., Str: Chemical structural formula (Me: methyl, Et: ethyl, nPr: n-propyl, iPr: isopropyl, cPr: cyclopropyl, nBu: n-butyl, iBu: isobutyl, Boc: tert-butyloxycarbonyl, Ac: acetyl, Z: benzyloxycarbonyl, and Ts: 4-methylphenylsulfonyl), DATA: Physicochemical data, ESI+: m/z values in mass spectroscopy (Ionization ESI, representing [M+H]$^+$ unless restricted), ESI−: m/z values in mass spectroscopy (Ionization ESI, representing [M−H]$^-$ unless restricted), APCI/ESI+: APCI/ESI-MS (Atmospheric chemical ionization APCI, APCI/ESI represents simultaneous measurement of APCI and ESI, representing [M+H]$^+$ unless limited), EI: m/z values in mass spectroscopy (Ionization EI, representing [M]$^+$ unless restricted), CI+: m/z values in mass spectroscopy (Ionization CI, representing [M+H]$^+$ unless restricted), m.p.: melting point, NMR (DMSO-d6): δ (ppm) of peak in $^1$H NMR in DMSO-d$_6$, s: singlet (spectrum), d: doublet (spectrum), t: triplet (spectrum), q: quartet (spectrum), br: broad line (spectrum) (for example, brs), and m: multiplet (spectrum). Further, in the structural formula, HCl denotes that the compound is monohydrochloride, 2HCl denotes that the compound is dihydrochloride, and 3HCl denotes that the compound is trihydrochloride.

Furthermore, for convenience, the concentration mol/L is expressed as M. For example, a 1 M aqueous sodium hydroxide solution means a 1 mol/L aqueous sodium hydroxide solution.

Further, the on-set temperatures of the DSC curve obtained by measurement under the following conditions are described as melting points in Tables below.

The DSC measurement was carried out using TA Instruments DSC Q20, under the conditions of a measurement temperature range from room temperature to 300° C., a temperature elevating rate of 10° C./min, a nitrogen flow rate of 50 mL/min, with an aluminum sample pan.

The powder X-ray diffraction was measured using RINT-TTRII under the conditions of a tube of Cu, a tube current of 300 mA, a tube voltage of 50 kV, a sampling width of 0.020°, a scanning speed of 4°/min, a wavelength of 1.54056 angstroms, and a measurement diffraction angle (2θ) of 2.5° to 40°.

Furthermore, for the powder X-ray diffraction spectrum, crystal lattice spacings or overall patterns are important in identity certification of crystals in the nature of the data. The diffraction angle and the diffraction intensity may vary more or less depending on the orientation of the crystal growth, the particle size, or the measurement conditions, and thus, the values should not be strictly interpreted.

Preparation Example 1

To a solution of 1-[4-hydroxy-3-(trifluoromethyl)phenyl]ethanone (1 g) in acetonitrile (10 mL) were added 1-bromopropane (0.90 mL), potassium carbonate (1.7 g), and tetrabutylammonium iodide (180 mg), followed by stirring at room temperature overnight. The insoluble materials were separated by filtration and the filtrate was concentrated under reduced pressure. The residue was purified by silica gel column chromatography (hexane-ethyl acetate) to obtain 1-[4-propoxy-3-(trifluoromethyl)phenyl]ethanone (1.16 g) as an oily substance.

Preparation Example 2

A mixture of 1-[4-hydroxy-3-(trifluoromethyl)phenyl]ethanone (1 g), iodoethane (1.19 mL), cesium carbonate (1.92 g), and N,N-dimethylformamide (15 mL) was stirred at 60° C. for 3 hours. The reaction mixture was cooled to room temperature and water was added thereto, followed by extraction with ethyl acetate. The organic layer was washed with water and a saturated aqueous sodium chloride solution, and dried over anhydrous sodium sulfate. The insoluble materials were then separated by filtration and the filtrate was concentrated under reduced pressure. The residue was purified by silica gel column chromatography (hexane-ethyl acetate) to obtain 1-[4-ethoxy-3-(trifluoromethyl)phenyl]ethanone (1.1 g) as a solid.

Preparation Example 3

To a solution of 1-[4-hydroxy-3-(trifluoromethyl)phenyl]ethanone (1 g) in tetrahydrofuran (10 mL) were added 2-propanol (0.46 mL), a 40% diethylazodicarboxylate solution in toluene (2.3 mL), and triphenyl phosphine (1.55 g), followed by stirring at room temperature overnight. The reaction mixture was concentrated under reduced pressure and the residue was purified by silica gel column chromatography (hexane-ethyl acetate) to obtain 1-[4-isopropoxy-3-(trifluoromethyl)phenyl]ethanone (1.05 g) as an oily substance.

Preparation Example 4

Under an argon atmosphere, zinc powder (1.86 g), cobalt (II) bromide (520 mg), and acetonitrile (20 mL) were mixed, and trifluoroacetic acid (0.14 mL) was added thereto, followed by stirring at room temperature for 15 minutes. To the reaction mixture were added a 1-bromo-3-methoxy-5-(trifluoromethoxy)benzene (4.61 g) in acetonitrile (10 mL) solution and acetic anhydride (1.93 mL), followed by stirring at room temperature for 5 hours. To the reaction mixture was added 1 M hydrochloric acid, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 1-[3-methoxy-5-(trifluoromethoxy)phenyl]ethanone (2.29 g) as an oily substance.

Preparation Example 5

1-[4-Methoxy-3-(trifluoromethyl)phenyl]ethanone (15 g) and tetrahydrofuran (270 mL) were mixed, and phenyltrimethylammonium tribromide (28.42 g) was added thereto, followed by stirring at room temperature for 30 minutes. The precipitated insoluble materials were separated by filtration and the filtrate was concentrated under reduced pressure. The obtained residue and ethanol (260 mL) were mixed, and thiourea (6.81 g) was added thereto, followed by stirring at 80° C. for 3 hours. The reaction mixture was cooled to room temperature, and water, a 1 M aqueous sodium hydroxide solution, and ethyl acetate was added thereto. The organic layer was washed with a 1 M aqueous sodium hydroxide solution, water, and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 4-[4-methoxy-3-(trifluoromethyl)phenyl]-1,3-thiazol-2-amine (16.18 g) as a solid.

Preparation Example 6

5-Chloropyrazine-2-carboxylic acid (3.00 g), N,N-dimethylformamide (30 mL), ethyl piperidine-4-carboxylate (5.83 mL), and diisopropylethylamine (6.50 mL) were mixed, followed by stirring at 80° C. overnight. The reaction mixture was cooled to room temperature and ethyl acetate was added thereto. The mixture was washed with an aqueous citric acid solution, water, and a saturated aqueous sodium chloride solution, and dried over anhydrous magnesium sulfate. The insoluble materials were then separated by filtration and the filtrate was concentrated under reduced pressure. The obtained solid was washed with diisopropyl ether and dried to obtain 5-[4-(ethoxycarbonyl)piperidin-1-yl]pyrazine-2-carboxylic acid (3.96 g) as a solid.

Preparation Example 7

To a mixture of 4-[4-propoxy-3-(trifluoromethyl)phenyl]-1,3-thiazol-2-amine (1.27 g), 5-[4-(ethoxycarbonyl)piperidin-1-yl]pyrazine-2-carboxylic acid (1.29 g), and pyridine (20 mL) was added dropwise phosphorous oxychloride (0.44 mL) at –10° C., followed by stirring at the same temperature for 1 hour. To the reaction mixture were added ethyl acetate and an aqueous citric acid solution, and the insoluble materials were dissolved therein. Then, silica gel was added thereto, followed by stirring. The insoluble materials were separated by filtration and the aqueous layer of the filtrate was separated, followed by extraction with ethyl acetate. The organic layer was combined and basic silica gel was added thereto, followed by stirring. The insoluble materials were then separated by filtration and the filtrate was concentrated under reduced pressure. To the residue was added diisopropyl ether, followed by stirring, and the solid was collected by filtration and dried to obtain ethyl 1-[5-({4-[4-propoxy-3-(trifluoromethyl)phenyl]-1,3-thiazol-2-yl}carbamoyl)pyrazin-2-yl]piperidine-4-carboxylate (1.38 g) as a solid.

Preparation Example 8

Under an argon atmosphere, to a solution of 1-tert-butyl 3-ethyl-3-methylpiperidine-1,3,3-tricarboxylate (2.35 g) in tetrahydrofuran (28 mL) was added a 3 M lithium borohydride/tetrahydrofuran solution (19.87 mL) at an internal temperature of –5° C. or lower, followed by stirring for 30 minutes, and then stirring at 60° C. for 20 hours. The reaction mixture was ice-cooled, and a saturated aqueous ammonium chloride solution was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (chloroform-methanol) to obtain tert-butyl 3,3-bis(hydroxymethyl)piperidine-1-carboxylate (1.22 g).

Preparation Example 9

4-[3-Methoxy-5-(trifluoromethyl)phenyl]-1,3-thiazol-2-amine (500 mg), tetrahydrofuran (10 mL), 5-[4-(ethoxycarbonyl)piperidin-1-yl]pyrazine-2-carboxylic acid (560 mg), O-(benzotriazol-1-yl)-N,N,N',N'-tetramethyluronium tetrafluoroborate (645 mg), and diisopropylethylamine (0.69 mL) were mixed, followed by stirring at 145° C. for 30 minutes under irradiation with microwaves. The reaction mixture was cooled to room temperature and ethyl acetate was added thereto. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) and the obtained solid was washed with diisopropyl ether and dried to obtain ethyl 1-[5-({4-[3-methoxy-5-(trifluoromethyl)phenyl]-1,3-thiazol-2-yl}carbamoyl)pyrazin-2-yl]piperidine-4-carboxylate (704 mg) as a solid.

Preparation Example 10

5-{[(2R)-2-Methylpyrrolidin-1-yl]methyl}-4-[3-methyl-5-(trifluoromethoxy)phenyl]-1,3-thiazol-2-amine (1.75 g), 5-chloropyrazine-2-carboxylic acid (1.13 g), N-[({[(1Z)-1-cyano-2-ethoxy-2-oxoethylidene]amino}oxy)(morpholin-4-yl)methylene]-N-methylmethanaminium hexafluorophosphate (3.1 g), dioxane (20 mL), and diisopropylethylamine (2.43 mL) were mixed, followed by stirring at room temperature for 1 hour, and to the reaction mixture was added ethyl acetate. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 5-chloro-N-(5-{[(2R)-2-methylpyrrolidin-1-yl]methyl}-4-[3-methyl-5-(trifluoromethoxy)phenyl]-1,3-thiazol-2-yl)pyrazine-2-carboxamide (1.71 g).

Preparation Example 11

5-Chloropyrazine-2-carboxylic acid (15.0 g) and ethyl acetate (200 mL) were mixed, and thionyl chloride (30 mL) and N,N-dimethylformamide (0.28 mL) were added thereto, followed by stirring at 55° C. to 60° C. for 1 hour. The reaction mixture was concentrated under reduced pressure, and an operation of adding toluene to the residue and concentrating the mixture was carried out twice.

4-[4-Methoxy-3-(trifluoromethyl)phenyl]-1,3-thiazol-2-amine (19.96 g) and cyclopentylmethyl ether (200 mL) were mixed, and to the mixture was added dropwise a solution of the residue obtained above in cyclopentylmethyl ether (40 mL) at 10° C. or lower, and the reaction mixture was warmed to room temperature and stirred for 5 hours. The reaction mixture was ice-cooled and water (600 mL) was added dropwise thereto at 15° C. or lower, followed by stirring at room temperature overnight. The precipitated solid was collected by filtration, washed with methyl ethyl ketone, and then dried to obtain 5-chloro-N-{4-[4-methoxy-3-(trifluoromethyl)phenyl]-1,3-thiazol-2-yl}pyrazine-2-carboxamide (29 g) as a solid.

Preparation Example 12

5-[4-(Ethoxycarbonyl)piperidin-1-yl]pyrazine-2-carboxylic acid (895 mg), N,N-dimethylformamide (10 mL), O-(7-azabenzotriazol-1-yl)-N,N,N',N'-tetramethyluronium tetrafluoroborate (1.34 g), and diisopropylethylamine (1.10 mL) were mixed, followed by stirring for 10 minutes. Under a nitrogen atmosphere, 4-[3,5-bis(trifluoromethyl)phenyl]-1, 3-thiazol-2-amine (1.0 g) and N,N-dimethylformamide (10 mL) were mixed, and sodium hydride (154 mg) was added thereto under ice-cooling, followed by stirring for 10 minutes. Then, the reaction mixture that had been prepared in advance was added thereto, followed by heating at 80° C. and stirring for 30 minutes. The reaction mixture was heated to 120° C. and further stirred for 1 hour. Then, 4-[3,5-bis(trifluoromethyl)phenyl]-1,3-thiazol-2-amine (0.72 g) was added thereto, followed by further stirring at the same temperature for 2 hours. The reaction mixture was cooled to room temperature and ethyl acetate was added thereto. The mixture was washed with water, a saturated aqueous sodium hydrogen carbonate solution, and a saturated aqueous sodium chloride solution, and dried over anhydrous magnesium sulfate. The insoluble materials were then separated by filtration and the filtrate was concentrated under reduced pressure. The residue was purified by silica gel column chromatography (chloroform-ethyl acetate). To the obtained residue was added diisopropyl ether, and the obtained solid was collected by filtration and dried to obtain ethyl 1-[5-({4-[3,5-bis(trifluoromethyl)phenyl]-1,3-thiazol-2-yl}carbamoyl)pyrazin-2-yl]piperidine-4-carboxylate (167 mg) as a solid.

Preparation Example 13

4-[4-Chloro-3-(trifluoromethyl)phenyl]-5-[(3-methoxy-3-methylpiperidin-1-yl)methyl]-1,3-thiazol-2-amine (80 mg), 5-[4-(ethoxycarbonyl)piperidin-1-yl]pyrazine-2-carboxylic acid (64 mg), N-[({[(1Z)-1-cyano-2-ethoxy-2-oxoethylidene]amino}oxy)(morpholin-4-yl)methylene]-N-methylmethanaminium hexafluorophosphate (101 mg), diisopropylethylamine (0.082 mL), and dioxane (1.2 mL) were mixed, followed by stirring at 80° C. for 30 minutes under irradiation with microwaves. The reaction mixture was concentrated under reduced pressure and the residue was purified by basic silica gel column chromatography (chloroform-hexane) and basic silica gel column chromatography (ethyl acetate-hexane). The obtained solid was washed with ethyl acetate-hexane and dried to obtain ethyl 1-[5-({4-[4-chloro-3-(trifluoromethyl)phenyl]-5-[(3-methoxy-3-methylpiperidin-1-yl)methyl]-1,3-thiazol-2-yl}carbamoyl)pyrazin-2-yl]piperidine-4-carboxylate (71 mg) as a solid.

Preparation Example 14

4-[3-Methyl-5-(trifluoromethoxy)phenyl]-1,3-thiazol-2-amine (500 mg), N,N-dimethylformamide (10 mL), 5-[4-(ethoxycarbonyl)piperidin-1-yl]pyrazine-2-carboxylic acid (764 mg), N-[({[(1Z)-1-cyano-2-ethoxy-2-oxoethylidene]amino}oxy)(morpholin-4-yl)methylene]-N-methylmethanaminium hexafluorophosphate (1.17 g), and diisopropylethylamine (0.94 mL) were mixed, followed by stirring at 150° C. for 30 minutes under irradiation with microwaves. The reaction mixture was cooled to room temperature and ethyl acetate was added thereto. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate), and the obtained residue was washed with diisopropyl ether and dried to obtain ethyl 1-[5-({4-[3-methyl-5-(trifluoromethoxy)phenyl]-1,3-thiazol-2-yl}carbamoyl)pyrazin-2-yl]piperidine-4-carboxylate (476 mg) as a solid.

Preparation Example 15

4-[4-Chloro-3-(trifluoromethyl)phenyl]-1,3-thiazol-2-amine (748 mg), 5-[4-(ethoxycarbonyl)piperidin-1-yl]pyrazine-2-carboxylic acid (500 mg), N,N-dimethylformamide (10 mL), O-(7-azabenzotriazol-1-yl)-N,N,N',N'-tetramethyluronium tetrafluoroborate (1.02 g), and diisopropylethylamine (0.93 mL) were mixed, followed by stirring at 100° C. overnight. The reaction mixture was cooled to room temperature and ethyl acetate was added thereto. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (chloroform-ethyl acetate), and the obtained residue was washed with diisopropyl ether and dried to obtain ethyl 1-[5-({4-[4-chloro-3-(trifluoromethyl)phenyl]-1,3-thiazol-2-yl}carbamoyl)pyrazin-2-yl]piperidine-4-carboxylate (294 mg) as a solid.

Preparation Example 16

4-[3-Methyl-5-(trifluoromethoxy)phenyl]-1,3-thiazol-2-amine (5.68 g), pyridine (17 mL), and acetic anhydride (7.8 mL) were mixed, followed by stirring at 60° C. for 1 hour. The reaction mixture was cooled to room temperature and ethyl acetate was added thereto. The mixture was washed with water, 1 M hydrochloric acid, and a saturated aqueous sodium chloride solution, and dried over anhydrous magnesium sulfate. The insoluble materials were then separated by filtration and the filtrate was concentrated under reduced pressure. The obtained solid was washed with diisopropyl ether and dried to obtain N-{4-[3-methyl-5-(trifluoromethoxy)phenyl]-1,3-thiazol-2-yl}acetamide (6.21 g) as a solid.

Preparation Example 17

To ethyl 1-[5-({4-[4-methoxy-3-(trifluoromethyl)phenyl]-1,3-thiazol-2-yl}carbamoyl)pyrazin-2-yl]piperidine-4-carboxylate (2.0 g) were added acetic acid (50 mL) and a 36% aqueous formaldehyde solution (1.5 mL), followed by stirring at 100° C. for 1.5 hours. To the reaction mixture was added acetic anhydride (0.71 mL), followed by further stirring at the same temperature for 1.5 hours. Then, acetic anhydride (0.71 mL) was added thereto again, followed by stirring for 0.5 hours. The reaction mixture was concentrated under reduced pressure, and to the residue was added ethanol, followed by stirring. The precipitated solid was collected by filtration and dried to obtain ethyl 1-[5-({5-(acetoxymethyl)-4-[4-methoxy-3-(trifluoromethyl)phenyl]-1,3-thiazol-2-yl}carbamoyl)pyrazin-2-yl]piperidine-4-carboxylate (1.77 g) as a solid.

Preparation Example 18

Ethyl 1-[5-({4-[3-methoxy-5-(trifluoromethyl)phenyl]-1,3-thiazol-2-yl}carbamoyl)pyrazin-2-yl]piperidine-4-carboxylate (1.87 g), acetic acid (8 mL), a 36% aqueous formaldehyde solution (2.69 mL), and acetic anhydride (3.30 mL) were mixed, followed by stirring at 150° C. for 30 minutes under irradiation with microwaves. The reaction mixture was concentrated under reduced pressure, and to the residue was added water and a saturated aqueous sodium hydrogen carbonate solution, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (chloroform-ethyl acetate) and the obtained solid was washed with diisopropyl ether, and dried to obtain ethyl 1-[5-({5-(acetoxymethyl)-4-[3-methoxy-5-(trifluoromethyl)phenyl]-1,3-thiazol-2-yl}carbamoyl)pyrazin-2-yl]piperidine-4-carboxylate (705 mg) as a solid.

Preparation Example 19

To ethyl 1-[5-({4-[4-propoxy-3-(trifluoromethyl)phenyl]-1,3-thiazol-2-yl}carbamoyl)pyrazin-2-yl]piperidine-4-carboxylate (1.38 g) were added acetic acid (35 mL), acetic anhydride (1.2 mL), and a 36% aqueous formaldehyde solution (0.98 mL), followed by stirring at 100° C. for 3 hours. The reaction mixture was concentrated under reduced pressure and the residue was purified by silica gel column chromatography (chloroform-ethyl acetate). The obtained residue was dissolved in pyridine (14 mL), and acetic anhydride (1.4 mL) was added thereto, followed by stirring at room temperature for 2 hours. The reaction mixture was concentrated under reduced pressure and the residue was purified by silica gel column chromatography (chloroform-ethyl acetate). The obtained solid was stirred in an ethyl acetate-diisopropyl ether mixed solvent, collected by filtration, and dried to obtain ethyl 1-[5-({5-(acetoxymethyl)-4-[4-propoxy-3-(trifluoromethyl)phenyl]-1,3-thiazol-2-yl}carbamoyl)pyrazin-2-yl]piperidine-4-carboxylate (771 mg) as a solid.

Preparation Example 20

Ethyl 1-[5-({4-[4-chloro-3-(trifluoromethyl)phenyl]-1,3-thiazol-2-yl}carbamoyl)pyrazin-2-yl]piperidine-4-carboxylate (1.15 g), acetic acid (12.0 mL), a 36% aqueous formaldehyde solution (2.0 mL), and acetic anhydride (2.5 mL) were mixed, followed by stirring at 150° C. for 1 hour under irradiation with microwaves. The reaction mixture was concentrated under reduced pressure, and to the residue were added pyridine (8 mL) and acetic anhydride (2.5 mL), followed by stirring at room temperature for 1 hour. The reaction mixture was concentrated under reduced pressure, and to the residue was added water, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The obtained solid was washed with a chloroform-ethyl acetate mixed solvent and dried to obtain ethyl 1-[5-({5-(acetoxymethyl)-4-[4-chloro-3-(trifluoromethyl)phenyl]-1,3-thiazol-2-yl}carbamoyl)pyrazin-2-yl]piperidine-4-carboxylate (564 mg) as a solid.

Preparation Example 21

5-Chloro-N-{4-[4-methoxy-3-(trifluoromethyl)phenyl]-1,3-thiazol-2-yl}pyrazine-2-carboxamide (4.27 g), acetic acid (50 mL), a 36% aqueous formaldehyde solution (4.0 mL), and (2R)-2-ethylpyrrolidine hydrochloride (7.0 g) were mixed and stirred at 90° C. for 1 hour, and dichloroethane (50 mL) was then added thereto, followed by stirring overnight. The reaction mixture was cooled to room temperature and concentrated under reduced pressure, and to the obtained residue was added ethyl acetate. The mixture was washed with a 1 M aqueous sodium hydroxide solution, water, and a saturated aqueous sodium chloride solution, and dried over anhydrous magnesium sulfate. The insoluble materials were then separated by filtration and the filtrate was concentrated under reduced pressure. To the obtained residue was added ethyl acetate, and the insoluble materials were separated by filtration. The filtrate was then concentrated under reduced pressure and the residue was purified by basic silica gel column chromatography (hexane-ethyl acetate). The obtained solid was washed with hexane and dried to obtain 5-chloro-N-(5-{[(2R)-2-ethylpyrrolidin-1-yl]methyl}-4-[4-methoxy-3-(trifluoromethyl)phenyl]-1,3-thiazol-2-yl)pyrazine-2-carboxamide (954 mg) as a solid.

Preparation Example 22

Ethyl 1-[5-({4-[4-(dimethylamino)-3-(trifluoromethyl)phenyl]-1,3-thiazol-2-yl}carbamoyl)pyrazin-2-yl]piperidine-4-carboxylate (200 mg), acetic acid (3 mL), a 36% aqueous formaldehyde solution (0.14 mL), and (2R)-2-methylpyrrolidine L-(+)-tartrate (425 mg) were mixed, followed by stirring at 110° C. for 30 minutes under irradiation with microwaves. The reaction mixture was neutralized by the addition of a saturated aqueous sodium hydrogen carbonate solution, followed by extraction with ethyl acetate. The organic layer was washed with a 1 M aqueous sodium hydroxide solution and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain ethyl 1-{5-[(4-[4-(dimethylamino)-3-(trifluoromethyl)phenyl]-5-{[(2R)-2-methylpyrrolidin-1-yl]methyl}-1,3-thiazol-2-yl)carbamoyl]pyrazin-2-yl}piperidine-4-carboxylate (110 mg) as a solid.

Preparation Example 23

Ethyl 1-[5-({5-(acetoxymethyl)-4-[4-methoxy-3-(trifluoromethyl)phenyl]-1,3-thiazol-2-yl}carbamoyl)pyrazin-2-yl]piperidine-4-carboxylate (2.5 g), (2R)-2-ethylpyrrolidine hydrochloride (690 mg), diisopropylethylamine (1.42 mL), and N,N-dimethylformamide (25 mL) were mixed, followed by stirring at 90° C. for 1 hour. The reaction mixture was diluted with ethyl acetate, washed with water, and dried over anhydrous sodium sulfate. The insoluble materials were then filtered and the filtrate was concentrated under reduced pressure. The residue was purified by basic silica gel column chromatography (chloroform-ethyl acetate) to obtain ethyl 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylate (2.28 g).

Preparation Example 24

To a solution of ethyl 1-[5-({5-(acetoxymethyl)-4-[4-chloro-3-(trifluoromethyl)phenyl]-1,3-thiazol-2-yl}carbamoyl)pyrazin-2-yl]piperidine-4-carboxylate (160 mg) in tetrahydrofuran (1.6 mL) were added (2R)-2-methylpyrrolidine hydrochloride (64 mg) and diisopropylethylamine (0.18 mL), followed by stirring at 150° C. for 1 hour under irradiation with microwaves. The reaction mixture was concentrated under reduced pressure and the residue was purified by silica gel column chromatography (hexane-ethyl acetate) to obtain ethyl 1-{5-[(4-[4-chloro-3-(trifluoromethyl)phenyl]-5-{[(2R)-2-methylpyrrolidin-1-yl]

methyl}-1,3-thiazol-2-yl)carbamoyl]pyrazin-2-yl}piperidine-4-carboxylate (117 mg) as an oily substance.

Preparation Example 25

To a solution of benzyl (2S)-2-(2-methoxypropan-2-yl)pyrrolidine-1-carboxylate (650 mg) in ethanol (6.5 mL) was added 10% palladium-supported carbon (50% wet, 150 mg), followed by stirring at room temperature for 1 hour at 1 atm under a hydrogen atmosphere. The insoluble materials were separated by filtration, and to the filtrate was added a 4 M hydrogen chloride/dioxane solution (2 mL), followed by concentration under reduced pressure. The residue was dried overnight to obtain (2S)-2-(2-methoxypropan-2-yl)pyrrolidine hydrochloride (438 mg) as a solid.

Preparation Example 26

To a solution of tert-butyl (2R)-2-ethylpyrrolidine-1-carboxylate (3.41 g) in dioxane (25 mL) was added a 4 M hydrogen chloride/dioxane solution (25 mL), followed by stirring at room temperature for 1 hour. The reaction mixture was concentrated under reduced pressure, and to the residue was added diethyl ether, followed by stirring. The precipitated solid was collected by filtration and dried to obtain (2R)-2-ethylpyrrolidine hydrochloride (2.1 g) as a solid.

Preparation Example 27

N-(5-{[(2R)-2-Methylpyrrolidin-1-yl]methyl}-4-[3-methyl-5-(trifluoromethoxy)phenyl]-1,3-thiazol-2-yl)acetamide (3.05 g), ethanol (20 mL), and a 6 M aqueous sodium hydroxide solution (12 mL) were mixed, followed by stirring at 120° C. for 15 minutes under irradiation with microwaves. To the reaction mixture was added water, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by basic silica gel column chromatography (hexane-ethyl acetate) to obtain 5-{[(2R)-2-methylpyrrolidin-1-yl]methyl}-4-[3-methyl-5-(trifluoromethoxy)phenyl]-1,3-thiazol-2-amine (1.75 g) as an oily substance.

Preparation Example 28

To a mixture of 2-(2,5-dimethyl-1H-pyrrol-1-yl)-4-[3-methoxy-4-(trifluoromethyl)phenyl]-1,3-thiazole (280 mg), ethanol (2.5 mL) and water (0.84 mL) were added hydroxylamine hydrochloride (828 mg) and triethylamine (0.55 mL), followed by stirring at 130° C. for 30 minutes under irradiation with microwaves. Ethanol was evaporated under reduced pressure and to the residue was added water, followed by extraction with chloroform. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) and purified by silica gel column chromatography (chloroform-methanol) to obtain 4-[3-methoxy-4-(trifluoromethyl)phenyl]-1,3-thiazol-2-amine (113 mg) as a solid.

Preparation Example 29

Under an argon atmosphere, to a solution of tert-butyl 3,3-bis(hydroxymethyl)piperidine-1-carboxylate (0.9 g) in tetrahydrofuran (18 mL) was added a 2.69 M n-butyllithium/tetrahydrofuran solution (1.39 mL) at −5° C. or lower, followed by stirring for 20 minutes. To the reaction mixture was added dropwise a solution of toluenesulfonyl chloride (0.7 g) in tetrahydrofuran (4.5 mL) at −5° C. or lower, followed by stirring for 40 minutes. To the resulted mixture was added a 2.69 M n-butyllithium/tetrahydrofuran solution (1.43 mL), followed by stirring for 30 minutes, then heating to 60° C., and further stirring for 1 hour. The reaction mixture was ice-cooled, and a saturated aqueous ammonium chloride solution was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain tert-butyl 2-oxa-6-azaspiro[3.5]nonane-6-carboxylate (436 mg).

Preparation Example 30

To a solution of (3R)-tetrahydrofuran-3-ol (1.0 g) in N-methylpyrrolidone (20 mL) was added a 60% oil dispersion of sodium hydride (430 mg) under ice-cooling, followed by stirring at the same temperature for 10 minutes. To the reaction mixture was added dropwise a solution of 1-[4-fluoro-3-(trifluoromethyl)phenyl]ethanone (2.0 g) in N-methylpyrrolidone (10 mL), and the mixture was stirred for 1 hour under ice-cooling. To the reaction mixture was added water, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 1-{4-[(3R)-tetrahydrofuran-3-yloxy]-3-(trifluoromethyl)phenyl}ethanone (1.84 g) as an oily substance.

Preparation Example 31

A mixture of 1-[4-fluoro-3-(trifluoromethyl)phenyl]ethanone (2.0 g), pyrrolidine (10 mL), potassium carbonate (2.0 g), and acetonitrile (3.0 mL) was stirred at 80° C. for 2 hours. The reaction mixture was cooled to room temperature and water was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain 1-[4-(pyrrolidin-1-yl)-3-(trifluoromethyl)phenyl]ethanone (2.5 g) as an oily substance.

Preparation Example 32

To a solution of 2-(2,5-dimethyl-1H-pyrrol-1-yl)-4-[3-fluoro-4-(trifluoromethyl)phenyl]-1,3-thiazole (300 mg) in tetrahydrofuran (2.4 mL) was added sodium methoxide (60 mg), followed by stirring at 100° C. for 30 minutes under irradiation with microwaves. To the reaction mixture was added sodium methoxide (90 mg), followed by stirring at 130° C. for 1 hour under irradiation with microwaves. Then sodium methoxide (150 mg) was added thereto, followed by stirring at 150° C. for 30 minutes under irradiation with microwaves. The reaction mixture was concentrated under reduced pressure and the residue was purified by silica gel column chromatography (hexane-ethyl acetate) to obtain 2-(2,5-dimethyl-1H-pyrrol-1-yl)-4-[3-methoxy-4-(trifluoromethyl)phenyl]-1,3-thiazole (289 mg) as an oily substance.

Preparation Example 33

4-(5-Chloro-3-thienyl)-1,3-thiazol-2-amine (4.30 g), dichloromethane (80 mL) and diisopropylethylamine (4.2 mL) were mixed, and trifluoroacetic anhydride (4.2 mL) was added thereto under ice-cooling, followed by warming to room temperature and stirring for 1 hour. The reaction mixture was diluted with chloroform, washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate), and the obtained solid was washed with hexane and dried to obtain N-[4-(5-chloro-3-thienyl)-1,3-thiazol-2-yl]-2,2,2-trifluoroacetamide (5.56 g) as a solid.

Preparation Example 34

To a solution of 4-[3-fluoro-4-(trifluoromethyl)phenyl]-1,3-thiazol-2-amine (600 mg) in toluene (3.6 mL) were added hexane-2,5-dione (0.32 mL) and p-toluenesulfonic acid (44 mg), followed by stirring at 170° C. for 30 minutes under irradiation with microwaves. The reaction mixture was concentrated under reduced pressure, and to the residue was added a saturated aqueous sodium hydrogen carbonate solution, followed by extraction with ethyl acetate. The organic layer was washed with a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 2-(2,5-dimethyl-1H-pyrrol-1-yl)-4-[3-fluoro-4-(trifluoromethyl)phenyl]-1,3-thiazole (634 mg) as a solid.

Preparation Example 35

To a solution of (2-methylpyrrolidin-2-yl)methanol (300 mg) in tetrahydrofuran (3 mL) was added a solution of di-tert-butyl dicarbonate (0.85 g) in tetrahydrofuran (1.5 mL) at room temperature, followed by stirring at room temperature for 3 days. Then, to the reaction mixture was added a 1 M aqueous sodium hydroxide solution (1.8 mL), followed by stirring at room temperature for 2 hours. To the reaction mixture was added water, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain tert-butyl 2-(hydroxymethyl)-2-methylpyrrolidine-1-carboxylate (396 mg) as an oily substance.

Preparation Example 36

To a solution of 2-[(2S)-pyrrolidin-2-yl]propan-2-ol hydrochloride (1.0 g) in dichloroethane (15 mL) was added triethylamine (2.52 mL), followed by water-cooling. Benzyl chlorocarbonate (1.29 mL) was added thereto, followed by warming to room temperature and stirring for 2 hours. The reaction mixture was concentrated under reduced pressure, and to the residue was added water, followed by extraction with ethyl acetate. The organic layer was dried over anhydrous magnesium sulfate, the insoluble materials were then separated by filtration, and the filtrate was concentrated under reduced pressure. The residue was purified by silica gel column chromatography (hexane-ethyl acetate) to obtain benzyl (2S)-2-(2-hydroxypropan-2-yl)pyrrolidine-1-carboxylate (1.01 g) as an oily substance.

Preparation Example 37

N-[4-(5-Chloro-3-thienyl)-1,3-thiazol-2-yl]-2,2,2-trifluoroacetamide (5.56 g), (2R)-2-methylpyrrolidine (3.36 g), acetic acid (60 mL), and a 36% aqueous formaldehyde solution (2.75 mL) were mixed, followed by stirring at 60° C. for 1 hour. The reaction mixture was concentrated under reduced pressure and the residue was diluted with ethyl acetate, washed with a saturated aqueous sodium hydrogen carbonate solution and a saturated aqueous sodium chloride solution, and dried over anhydrous magnesium sulfate. The insoluble materials were then separated by filtration and the filtrate was concentrated under reduced pressure. The obtained residue, ethanol (60 mL), and a 6 M aqueous sodium hydroxide solution (15 mL) were mixed, followed by stirring at 90° C. for 2 hours. The reaction mixture was cooled to room temperature and water was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by basic silica gel column chromatography (hexane-ethyl acetate) to obtain 4-(5-chloro-3-thienyl)-5-{[(2R)-2-methylpyrrolidin-1-yl]methyl}-1,3-thiazol-2-amine (2.28 g).

Preparation Example 38

1-[4-Hydroxy-3-(trifluoromethyl)phenyl]ethanone (3.0 g), N,N-dimethylformamide (36 mL), and water (3.6 mL) were mixed, and sodium chloro(difluoro)acetate (5.76 g) and cesium carbonate (7.2 g) were added thereto, followed by stirring at 100° C. for 3 hours. To the reaction mixture was added water, followed by extraction with ethyl acetate. The organic layer was washed with water and a saturated aqueous sodium chloride solution, and concentrated under reduced pressure. The residue was purified by silica gel column chromatography (hexane-ethyl acetate) to obtain 1-[4-(difluoromethoxy)-3-(trifluoromethyl)phenyl]ethanone (3.80 g) as an oily substance. 1-[4-(Difluoromethoxy)-3-(trifluoromethyl)phenyl]ethanone (3.80 g) and tetrahydrofuran (50 mL) were mixed, and phenyltrimethylammonium tribromide (5.66 g) was added thereto, followed by stirring at room temperature for 45 minutes. The precipitated insoluble materials were separated by filtration and the filtrate was concentrated under reduced pressure. The residue and ethanol (50 mL) were mixed, and thiourea (1.47 g) was added thereto followed by stirring at 80° C. for 2 hours. The reaction mixture was cooled to room temperature, and water (30 mL) and a 1 M aqueous sodium hydroxide solution (30 mL) were added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. To the residue was added diisopropyl ether, the mixture was concentrated under reduced pressure, and then diisopropyl ether and hexane were further added thereto. The resulting solid was collected by filtration and dried to obtain 4-[4-(difluoromethoxy)-3-(trifluoromethyl)phenyl]-1,3-thiazol-2-amine (3.48 g) as a solid.

Preparation Example 39

3-Bromo-5-(trifluoromethoxy)phenol (4.84 g), N,N-dimethylformamide (50 mL), potassium carbonate (3.12 g), and methyl iodide (2.35 mL) were mixed, followed by stirring at room temperature for 2 hours. To the reaction mixture was added water, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 1-bromo-3-methoxy-5-(trifluoromethoxy)benzene (4.61 g) as an oily substance.

Preparation Example 40

To a mixture of benzyl (2S)-2-(2-hydroxypropan-2-yl)pyrrolidine-1-carboxylate (1.0 g), Proton Sponge (registered trademark) (2.44 g), and dichloromethane (15 mL) was added trimethyloxonium tetrafluoroborate (1.77 g) under ice-cooling, followed by warming to room temperature and stirring overnight. The insoluble materials were separated by filtration, and to the filtrate were added water and a 10% aqueous citric acid solution, followed by extraction with chloroform. The organic layer was dried over anhydrous magnesium sulfate and the insoluble materials were then separated by filtration. The filtrate was concentrated under reduced pressure. The residue was purified by silica gel column chromatography (hexane-ethyl acetate) to obtain benzyl (2S)-2-(2-methoxypropan-2-yl)pyrrolidine-1-carboxylate (664 mg) as an oily substance.

Preparation Example 41

To a solution of diisopropylamine (5.05 mL) in tetrahydrofuran (30 mL) was added a 2.66 M n-butyllithium/hexane solution (12.86 mL) at −78° C. under an argon atmosphere, followed by stirring for 15 minutes. To the reaction mixture was added dropwise a solution of 1-tert-butyl 3-ethyl piperidine-1,3-dicarboxylate (4.0 g) in tetrahydrofuran (20 mL) over 10 minutes, followed by stirring for 30 minutes. To the reaction mixture was added dropwise a solution of methyl iodide (1.455 mL) in tetrahydrofuran (10 mL) over 10 minutes, and the obtained mixture was warmed to 0° C. for 1 hour, followed by stirring at the same temperature for 30 minutes, then further warming to room temperature, and stirring for 3 hours. To the reaction mixture was added a saturated aqueous ammonium chloride solution, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain 1-tert-butyl 3-ethyl 3-methylpiperidine-1,3-dicarboxylate (3.29 g) as an oily substance.

Preparation Example 42

Under an argon atmosphere, a mixture of a 55% oil dispersion of sodium hydride (126 mg) and tetrahydrofuran (3 mL) was water-cooled, and a solution of tert-butyl 3-(hydroxymethyl)-3-methylpiperidine-1-carboxylate (442 mg) in tetrahydrofuran (2 mL) was added thereto, followed by stirring at room temperature for 5 minutes and then stirring at 60° C. for 30 minutes. The reaction mixture was ice-cooled, and methyl iodide (0.3 mL) was added thereto, followed by warming to room temperature and stirring for 1.5 hours. To the reaction mixture was added a saturated aqueous ammonium chloride solution, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain tert-butyl 3-(methoxymethyl)-3-methylpiperidine-1-carboxylate (414 mg) as an oily substance.

Preparation Example 43

N-{4-[3-Fluoro-5-(trifluoromethyl)phenyl]-1,3-thiazol-2-yl}acetamide (2.84 g), acetic acid (20 mL), a 36% aqueous formaldehyde solution (3.6 mL), and acetic anhydride (4.40 mL) were mixed, followed by stirring at 170° C. for 30 minutes under irradiation with microwaves. The reaction mixture was concentrated under reduced pressure, and the obtained solid was washed with methanol and dried to obtain a white solid. The obtained solid, N-methylpyrrolidone (20 mL), (2R)-2-methylpyrrolidine (608 mg), and diisopropylethylamine (2.45 mL) were mixed, followed by stirring at 100° C. for 30 minutes. The reaction mixture was cooled to room temperature and water was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain N-(4-[3-fluoro-5-(trifluoromethyl)phenyl]-5-{[(2R)-2-methylpyrrolidin-1-yl]methyl}-1,3-thiazol-2-yl)acetamide (1.38 g) as a solid.

Preparation Example 44

3-Bromo-1,1,1-trifluoroacetone (3.0 g), ethyl amino(thioxo)acetate (2.10 g), and ethanol (45 mL) were mixed, followed by heating to reflux for 15 hours. The reaction mixture was cooled to room temperature and concentrated under reduced pressure. To the residue was added a saturated aqueous sodium hydrogen carbonate solution (50 mL), and water (50 mL) was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain ethyl 4-(trifluoromethyl)-1,3-thiazole-2-carboxylate (2.19 g) as an oily substance. To a solution of ethyl 4-(trifluoromethyl)-1,3-thiazole-2-carboxylate (2.07 g) in ethanol (50 mL) was added a 1 M aqueous sodium hydroxide solution (30 mL), followed by stirring at 50° C. for 30 minutes. The reaction mixture was cooled to room temperature, and 1 M hydrochloric acid (30 mL) and water (100 mL) were added thereto, followed by extraction with a chloroform-isopropanol mixed solvent. The organic layer was dried over anhydrous magnesium sulfate, the insoluble materials were separated by filtration and the filtrate was concentrated under reduced pressure to obtain a solid. To the obtained solid was added hexane, the solvent was removed by decantation, and the solid was then dried to obtain 4-(trifluoromethyl)-1,3-thiazole-2-carboxylic acid (832 mg) as a solid.

Preparation Example 45

To 4-(trifluoromethyl)-1,3-thiazole-2-carboxylic acid (790 mg) were added thionyl chloride (4.0 mL), dichloromethane (6 mL), and N,N-dimethylformamide (1 droplet), followed by stirring at 40° C. for 2 hours. The reaction mixture was concentrated under reduced pressure, azeotropic distilled with toluene twice, and then dried under reduced pressure. To a mixture of magnesium chloride (382 mg) and toluene (12 mL) were added dimethyl malonate (0.55 mL) and triethylamine (1.3 mL), and the mixture was stirred at room temperature for 1.5 hours. To the reaction mixture was added dropwise a solution of the previously obtained residue in toluene (3 mL), followed by stirring at room temperature for 16 hours. To the reaction mixture was slowly added 6 M hydrochloric acid (5 mL), and then water (30 mL) was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was dissolved in dimethyl disulfoxide (4 mL) and water (0.4 mL), followed by stirring at 160° C. for 2 hours. The reaction mixture was cooled to room temperature, and then water (30 mL) was added thereto, followed by extraction with ethyl acetate. The organic layer was washed with a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) to obtain 1-[4-(trifluoromethyl)-1,3-thiazol-2-yl]ethanone (498 mg) as an oily substance.

Preparation Example 46

To a solution of tert-butyl (2S)-2-(hydroxymethyl)pyrrolidine-1-carboxylate (17 g), triethylamine (17.66 mL), and 1-methyl-1H-imidazole (10.05 mL) in dichloromethane (255 mL) was added p-toluenesulfonyl chloride (17.71 g) under ice-cooling, followed by stirring at the same temperature for 1 hour. To the reaction mixture was added water, followed by extraction with dichloromethane. The organic layer was washed with a saturated aqueous sodium chloride solution and dried over anhydrous sodium sulfate. The insoluble materials were then separated by filtration and the filtrate was concentrated under reduced pressure. The residue was purified by silica gel column chromatography (hexane-ethyl acetate) to obtain tert-butyl (2S)-2-({[(4-methylphenyl)sulfonyl]oxy}methyl)pyrrolidine-1-carboxylate (29.51 g) as an oily substance.

Preparation Example 47

To a mixture of copper (I) iodide (9.4 g) and diethyl ether (180 mL) was added dropwise an about 1 M methyllithium/ diethyl ether solution (100 mL) at an internal temperature of 0° C. to 5° C. over 30 minutes, followed by stirring for 15 minutes after the dropwise addition. To the reaction mixture was added a solution of tert-butyl (2S)-2-({[(4-methylphenyl)sulfonyl]oxy}methyl)pyrrolidine-1-carboxylate (7.0 g) in dichloromethane (30 mL), and the solution was kept at an internal temperature of 5° C. or lower and added dropwise over 20 minutes, followed by stirring at room temperature for 2.5 hours. To the reaction mixture was added dropwise a saturated aqueous ammonium chloride solution, followed by extraction with ethyl acetate. The organic layer was dried over anhydrous sodium sulfate. The insoluble materials were then separated by filtration and the filtrate was concentrated under reduced pressure. The residue was purified by silica gel column chromatography (hexane-ethyl acetate) to obtain tert-butyl (2R)-2-ethylpyrrolidine-1-carboxylate (3.52 g) as an oily substance.

Preparation Example 48

Under an argon atmosphere, to a solution of diisopropylamine (10.09 mL) in tetrahydrofuran (60 mL) was added a 2.69 M n-butyllithium/hexane solution (25.43 mL) at −78° C., followed by stirring at the same temperature for 15 minutes, then warming to −20° C., and stirring for 30 minutes. The reaction mixture was cooled to −78° C. again, and a solution of 1-tert-butyl 3-ethyl piperidine-1,3-dicarboxylate (8.0 g) in tetrahydrofuran (20 mL) was added dropwise thereto over 20 minutes, followed by warming to −20° C. and stirring for 30 minutes. The obtained mixture was cooled to −78° C., and a solution of methyl chlorocarbonate (5.98 mL) in tetrahydrofuran (16 mL) was added dropwise thereto over 15 minutes, followed by warming to room temperature and then stirring for 2 hours. To the reaction mixture was added dropwise a saturated aqueous ammonium chloride solution, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain 1-tert-butyl 3-ethyl 3-methyl piperidine-1,3,3-tricarboxylate (5.63 g) as an oily substance.

Preparation Example 92

To a mixture of 5-chloro-N-{4-[4-methoxy-3-(trifluoromethyl)phenyl]-1,3-thiazol-2-yl}pyrazine-2-carboxamide (29 g) and N-methylpyrrolidone (150 mL) were added diisopropylethylamine (18 mL) and ethyl piperidine-4-carboxylate (14 mL), followed by stirring at room temperature for 2 hours. The reaction mixture was ice-cooled and water was added thereto, followed by stirring at room temperature for 1 hour. The solid was collected by filtration and dried to obtain ethyl 1-[5-({4-[4-methoxy-3-(trifluoromethyl)phenyl]-1,3-thiazol-2-yl}carbamoyl)pyrazin-2-yl]piperidine-4-carboxylate (36.85 g) as a solid.

Preparation Example 209

A mixture of 1-[4-fluoro-3-(trifluoromethyl)phenyl]ethanone (3.75 g) and dimethylamine (2 M tetrahydrofuran solution, 22.3 mL) was stirred at 110° C. for 30 minutes under irradiation with microwaves. The reaction mixture was concentrated under reduced pressure and the residue was purified by silica gel column chromatography (hexane-ethyl acetate). To the obtained compound was added dimethylamine (2 M tetrahydrofuran solution, 15 mL), followed by stirring at 130° C. for 1 hour under irradiation with microwaves. The reaction mixture was concentrated under reduced pressure and the residue was purified by silica gel column chromatography (hexane-ethyl acetate) to obtain 1-[4-(dimethylamino)-3-(trifluoromethyl)phenyl]ethanone (2.89 g).

In the similar manner as the methods of Preparation Examples 1 to 48, 92, and 209, the compounds of Preparation Example 49 to 91, 93 to 208 and 210 to 212 in Tables below were prepared. The structures, the physicochemical data, and the preparation methods of the compounds of Preparation Examples are shown in Tables 4 to 36.

Example 1

To a solution of ethyl 1-{5-[(5-{[(2R)-2-ethylpyrrolidin-1-yl]methyl}-4-[4-propoxy-3-(trifluoromethyl)phenyl]-1,3 thiazol-2-yl)carbamoyl]pyrazin-2-yl}piperidine-4-carboxylate (159 mg) in dioxane (2 mL) was added a 1 M aqueous sodium hydroxide solution (2 mL), followed by stirring at 60° C. for 30 minutes. The reaction mixture was cooled to room temperature, neutralized by the addition of 1 M hydrochloric acid, extracted with chloroform, and concentrated under reduced pressure. The residue was purified by silica gel column chromatography (chloroform-methanol) to obtain a pale yellow solid.

The obtained solid was dissolved in dioxane (2 mL), a 4 M hydrogen chloride/dioxane solution (0.25 mL) was added thereto, and the precipitated solid was stirred in acetonitrile, then collected by filtration, and dried to obtain 1-{5-[(5-{[(2R)-2-ethylpyrrolidin-1-yl]methyl}-4-[4-propoxy-3-(trifluoromethyl)phenyl]-1,3-thiazol-2-yl)carbamoyl]pyrazin-2-yl}piperidine-4-carboxylic acid dihydrochloride (132 mg) as a solid.

Example 2

Ethyl 1-[5-({5-(acetoxymethyl)-4-[3-methoxy-5-(trifluoromethyl)phenyl]-1,3-thiazol-2-yl}carbamoyl)pyrazin-2-yl]piperidine-4-carboxylate (100 mg), N,N-dimethylformamide (2 mL), (2R)-2-methylpiperidine hydrochloride (45 mg), and diisopropylethylamine (0.115 mL) were mixed, followed by stirring at 100° C. for 1 hour. The reaction mixture was cooled to room temperature and diluted with ethyl acetate. The obtained mixture was washed with water and a saturated aqueous sodium chloride solution, and dried over anhydrous magnesium sulfate. The insoluble materials were then separated by filtration and the filtrate was concentrated under reduced pressure. The residue was purified by basic silica gel column chromatography (hexane-ethyl acetate). The obtained residue was mixed with ethanol (2 mL) and tetrahydrofuran (1 mL), and a 1 M aqueous sodium hydroxide solution (0.83 mL) was added thereto, followed by stirring at 50° C. for 20 minutes. The reaction mixture was cooled to room temperature, and 1 M hydrochloric acid (0.83 mL) and water were added thereto, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was mixed with ethyl acetate, and a 4 M hydrogen chloride/ethyl acetate solution (0.3 mL) was added thereto, followed by concentration under reduced pressure. The obtained solid was washed with ethyl acetate and dried to obtain 1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid dihydrochloride (56 mg) as a solid.

Example 3

5-Chloro-N-(5-{[(2R)-2-methylpyrrolidin-1-yl]methyl}-4-[3-methyl-5-(trifluoromethoxy)phenyl]-1,3-thiazol-2-yl)pyrazine-2-carboxamide (170 mg), N-methylpyrrolidone (3 mL), ethyl 4-fluoropiperidine-4-carboxylate (120 mg), and diisopropylethylamine (0.23 mL) were mixed, followed by stirring at 70° C. for 1 hour. The reaction mixture was cooled to room temperature and diluted with ethyl acetate. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate).

The obtained residue was mixed with ethanol (4 mL) and tetrahydrofuran (2 mL), and a 1 M aqueous sodium hydroxide solution (1.7 mL) was added thereto, followed by stirring at 50° C. for 20 minutes. The reaction mixture was cooled to room temperature and 1 M hydrochloric acid (1.7 mL) and water was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was mixed with ethyl acetate, and a 4 M hydrogen chloride/ethyl acetate solution (0.5 mL) was added thereto, followed by concentration under reduced pressure. The obtained solid was washed with ethyl acetate and dried to obtain 4-fluoro-1-{5-[(5-{[(2R)-2-methylpyrrolidin-1-yl]methyl}-4-[3-methyl-5-(trifluoromethoxy)phenyl]-1,3-thiazol-2-yl)carbamoyl]pyrazin-2-yl}piperidine-4-carboxylic acid dihydrochloride (116 mg) as a solid.

Example 4

Ethyl 1-(5-{[4-(4-chloro-2-thienyl)-1,3-thiazol-2-yl]carbamoyl}pyrazin-2-yl)piperidine-4-carboxylate (26.27 g), acetic acid (545 mL), a 36% aqueous formaldehyde solution (16.98 mL), and (2R)-2-methylpyrrolidine L-(+)-tartrate (51.71 g) were mixed, followed by stirring at 110° C. for 2 hours. The reaction mixture was cooled to room temperature and concentrated under reduced pressure, and the residue was diluted with ethyl acetate. The mixture was washed with an aqueous sodium hydrogen carbonate solution and a saturated aqueous sodium chloride solution, and dried over anhydrous sodium sulfate. The insoluble materials were then separated by filtration and the filtrate was concentrated under reduced pressure. The residue was purified by basic silica gel column chromatography (hexane-ethyl acetate).

The obtained residue was mixed with ethanol (450 mL), and a 1 M aqueous sodium hydroxide solution (150 mL) was added thereto, followed by stirring at 70° C. for 1 hour. The reaction mixture was cooled to room temperature, and water and 1 M hydrochloric acid (150 mL) were added thereto. The precipitated solid was collected by filtration, washed with water, and dried under reduced pressure. The obtained solid was mixed with ethyl acetate, and an excess amount of a 4 M hydrogen chloride/ethyl acetate solution was added thereto, followed by stirring at room temperature for 1 hour. The solid was collected by filtration and dried to obtain 1-(5-{[4-(4-chloro-2-thienyl)-5-{[(2R)-2-methylpyrrolidin-

47

1-yl]methyl}-1,3-thiazol-2-yl]carbamoyl}pyrazin-2-yl)piperidine-4-carboxylic acid dihydrochloride (23 g) as a solid.

Example 5

4-(5-Chloro-3-thienyl)-5-{[(2R)-2-methylpyrrolidin-1-yl]methyl}-1,3-thiazol-2-amine (300 mg) and dichloromethane (6 mL) were mixed, and 5-[4-(ethoxycarbonyl)piperidin-1-yl]pyrazine-2-carboxylic acid (347 mg), N-[3-(dimethylamino)propyl]-N'-ethylcarbodiimide hydrochloride (240 mg), and 4-(dimethylamino)pyridine (35 mg) were added thereto, followed by stirring at 40° C. for 1 hour. The reaction mixture was cooled to room temperature and diluted with ethyl acetate. The mixture was washed with water and a saturated aqueous sodium chloride solution, dried over anhydrous magnesium sulfate, and then filtered, and the filtrate was concentrated under reduced pressure. The residue was purified by silica gel column chromatography (hexane-ethyl acetate) and purified by basic silica gel column chromatography (hexane-ethyl acetate). The obtained residue was mixed with ethanol (4 mL) and tetrahydrofuran (2 mL), and a 1 M aqueous sodium hydroxide solution (3 mL) was added thereto, followed by stirring at 50° C. for 30 minutes. The reaction mixture was cooled to room temperature, and water and 1 M hydrochloric acid (3 mL) was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The obtained solid was washed with diisopropyl ether. The obtained solid was mixed with ethyl acetate, and a 4 M hydrogen chloride/ethyl acetate solution (1 mL) was added thereto, followed by concentration under reduced pressure.

The obtained solid was washed with ethyl acetate and dried to obtain 1-[5-{[4-{5-chloro-3-thienyl}-5-{[(2R)-2-methylpyrrolidin-1-yl]methyl}-1,3-thiazol-2-yl]carbamoyl}pyrazin-2-yl)piperidine-4-carboxylic acid dihydrochloride (143 mg) as a solid.

Example 6

Ethyl 1-[5-({4-[4-methoxy-3-(trifluoromethyl)phenyl]-1,3-thiazol-2-yl}carbamoyl)pyrazin-2-yl]piperidine-4-carboxylate (1.45 g), acetic acid (10 mL), a 36% aqueous formaldehyde solution (1.50 mL), and acetic anhydride (1.8 mL) were mixed, followed by stirring at 170° C. for 30 minutes under irradiation with microwaves. The reaction mixture was concentrated under reduced pressure, and to the residue were added water and a saturated aqueous sodium hydrogen carbonate solution, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (chloroform-ethyl acetate). The obtained residue was mixed with N,N-dimethylformamide (15 mL), N-(2-methoxyethyl)-2-methylpropane-1-amine hydrochloride (685 mg), and diisopropylethylamine (1.4 mL), followed by stirring at 100° C. for 1 hour. The reaction mixture was cooled to room temperature and ethyl acetate was added thereto. The mixture was washed with water and a saturated aqueous sodium chloride solution, and dried over anhydrous magnesium sulfate. The insoluble materials were then separated by filtration and the filtrate was concentrated under reduced pressure. The residue was purified by silica gel column chromatography (hexane-ethyl acetate) and the obtained solid was washed with diisopropyl ether. The obtained solid was mixed with ethanol (5 mL), and a 1 M aqueous sodium hydroxide solution (2.8 mL) was added thereto, followed by stirring at 60° C. for 15 minutes. The reaction mixture was cooled to room temperature, and water and 1 M hydrochloric acid (2.8 mL) was added thereto, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The obtained solid was washed with diisopropyl ether and dried to obtain 1-{5-[(5-{[isobutyl(2-methoxyethyl)amino]methyl}-4-[4-methoxy-3-(trifluoromethyl)phenyl]-1,3-thiazol-2-yl)carbamoyl]pyrazin-2-yl}piperidine-4-carboxylic acid (224 mg) as a solid.

Example 7

To a solution of tert-butyl 2-oxa-6-azaspiro[3,5]nonane-6-carboxylate (110 mg) in dichloromethane (1.1 mL) was added trifluoroacetic acid (0.30 mL) under ice-cooling, followed by warming to room temperature and stirring for 2 hours. The reaction mixture was concentrated under reduced pressure to obtain a 2-oxa-6-azaspiro[3,5]nonane trifluoroacetate. The obtained 2-oxa-6-azaspiro[3,5]nonane trifluoroacetate was used in the next step without further purification.

To a solution of ethyl 1-[5-({5-(acetoxymethyl)-4-[4-methoxy-3-(trifluoromethyl)phenyl]-1,3-thiazol-2-yl}carbamoyl)pyrazin-2-yl]piperidine-4-carboxylate (118 mg) in N,N-dimethylformamide (2.4 mL) were added diisopropylethylamine (0.33 mL) and the 2-oxa-6-azaspiro[3,5]nonane trifluoroacetate synthesized above, followed by stirring at 100° C. for 1.5 hours. The reaction mixture was concentrated under reduced pressure, and to the residue was added water. The resulting solid was collected by filtration, dried, and then purified by basic silica gel column chromatography (hexane-ethyl acetate). To a solution of the obtained residue (66 mg) in ethanol (2 mL) was added a 1 M aqueous sodium hydroxide solution (0.29 mL), followed by stirring at 60° C. for 1 hour. The reaction mixture was neutralized by the addition of 1 M hydrochloric acid, and water, a saturated aqueous sodium chloride solution, and chloroform were added thereto, and the organic layer was separated using a phase separator (International Sorbent Technology), and concentrated under reduced pressure. The residue was purified by silica gel column chromatography (chloroform-methanol), and the obtained solid was washed with ethanol and dried to obtain 1-[5-({4-[4-methoxy-3-(trifluoromethyl)phenyl]-5-(2-oxa-6-azaspiro[3,5]non-6-yl-methyl)-1,3-thiazol-2-yl}carbamoyl)pyrazin-2-yl]piperidine-4-carboxylic acid (52 mg) as a solid.

Example 8

To a mixture of ethyl 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylate (21.6 g) and ethanol (216 mL) was added a 1 M aqueous sodium hydroxide solution (74 mL), followed by stirring at 50° C. to 55° C. for 1.5 hours. To the reaction mixture was further added a 1 M aqueous sodium hydroxide solution (36 mL), followed by stirring at the same temperature for 2 hours. To the reaction mixture was added acetic acid (6.5 mL) at the same temperature, and the pH of the mixture was adjusted to 5 to 6. Water (106 mL) was added thereto, followed by stirring at 55° C. overnight. The mixture was cooled to room temperature and the solid was collected by filtration.

The obtained solid and ethanol (80 mL) were mixed and dissolved under heating to reflux. After cooling to room temperature, the precipitated solid was collected by filtration and ethanol (80 mL) was added thereto again, followed by heating to reflux for 1 hour and then cooling to room temperature. The precipitated solid was collected by filtration and dried to obtain 1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylic acid (12.78 g) as crystals.

The crystals obtained in Example 8 had peaks around 2θ (°) 5.0, 7.1, 10.0, 11.0, 11.8, 12.0, 15.6, 17.1, 20.4, 23.1, 24.9, and 26.8 in powder X-ray diffraction.

Example 103

To a mixture of ethyl 1-[5-({5-acetoxymethyl)-4-[4-methoxy-3-(trifluoromethyl)phenyl]-1,3-thiazol-2-yl}carbamoyl)pyrazin-2-yl]piperidine-4-carboxylate (110 mg) and N,N-dimethylformamide (2.2 mL) were added (3-methylpiperidin-3-yl)methanol hydrochloride (65 mg) and diisopropylethylamine (0.16 mL), followed by stirring at 100° C. for 1.5 hours. The reaction mixture was concentrated under reduced pressure and the residue was purified by silica gel column chromatography (hexane-ethyl acetate). The obtained compound was mixed with ethanol (1.8 mL), and a 1 M aqueous sodium hydroxide solution (0.35 mL) was added thereto, followed by stirring at 60° C. for 1 hour. The reaction mixture was neutralized by the addition of 1 M hydrochloric acid and concentrated under reduced pressure. To the residue were added water and chloroform, and the organic layer was separated using a phase separator (International Sorbent Technology) and concentrated under reduced pressure. The obtained solid was washed with ethanol/diisopropyl ether, collected by filtration, and dried to obtain 1-{5-[(5-{[3-(hydroxymethyl)-3-methylpiperidin-1-yl]methyl}-4-[4-methoxy-3-(trifluoromethyl)phenyl]-1,3-thiazol-2-yl)carbamoyl]pyrazin-2-yl}piperidine-4-carboxylic acid (36 mg).

Example 107

A mixture of ethyl 1-[5-({5-(acetoxymethyl)-4-[4-(morpholin-4-yl)-3-(trifluoromethyl)phenyl]-1,3-thiazol-2-yl}carbamoyl)pyrazin-2-yl]piperidine-4-carboxylate (300 mg), (2R)-2-propylpyrrolidine hydrochloride (150 mg), diisopropylethylamine (0.40 mL), and N,N-dimethylformamide (5.0 mL) was stirred at 100° C. for 2 hours. The reaction mixture was cooled to room temperature and water was added thereto, followed by extraction with ethyl acetate. The organic layer was washed with a saturated aqueous sodium chloride solution and dried over anhydrous magnesium sulfate. The insoluble materials were then separated by filtration and the filtrate was concentrated under reduced pressure. The residue was purified by silica gel column chromatography (hexane-ethyl acetate) to obtain a solid (200 mg). The obtained compound was mixed with tetrahydrofuran (5 mL) and ethanol (5 mL), and a 1 M aqueous sodium hydroxide solution were added thereto, followed by stirring at 60° C. for 1 hour. The reaction mixture was cooled to room temperature and concentrated under reduced pressure. The residue was purified by ODS silica gel column chromatography (acetonitrile-water). The obtained solid was mixed with hexane (20 mL), and the solid was collected by filtration and dried to obtain sodium 1-{5-[(4-[4-(morpholin-4-yl)-3-(trifluoromethyl)phenyl]-5-{[(2R)-2-propylpyrrolidin-1-yl]methyl}-1,3-thiazol-2-yl)carbamoyl]pyrazin-2-yl}piperidine-4-carboxylate (190 mg).

Example 141

Ethyl 1-(5-{[4-(4-chloro-2-thienyl)-1,3-thiazol-2-yl]carbamoyl}pyrazin-2-yl)piperidine-4-carboxylate (200 mg), acetic acid (4 mL), a 36% aqueous formaldehyde solution (0.113 mL) and 2-ethylpyrrolidine (208 mg) were mixed, followed by stirring at 90° C. for 3 hours. The reaction mixture was cooled to room temperature and concentrated under reduced pressure. The residue was diluted with ethyl acetate, and washed with a 1 M aqueous sodium hydroxide solution, water, and a saturated aqueous sodium chloride solution. The organic layer was dried over anhydrous magnesium sulfate. The insoluble materials were then separated by filtration and the filtrate was concentrated under reduced pressure. The residue was purified by silica gel column chromatography (hexane-ethyl acetate). The obtained compound and ethanol (4 mL) were mixed, and tetrahydrofuran (2 mL) and a 1 M aqueous sodium hydroxide solution (2.10 mL) were added thereto, followed by stirring at 50° C. for 20 minutes. The reaction mixture was cooled to room temperature, and water and 1 M hydrochloric acid (2.10 mL) was added thereto, followed by extraction with ethyl acetate. The organic layer was washed with water and a saturated aqueous sodium chloride solution, and dried over anhydrous magnesium sulfate. The insoluble materials were then separated by filtration and the filtrate was concentrated under reduced pressure. The obtained solid was washed with diisopropyl ether, collected by filtration, and dried to obtain 1-[5-({4-(4-chloro-2-thienyl)-5-[(2-ethylpyrrolidin-1-yl)methyl]-1,3-thiazol-2-yl}carbamoyl)pyrazin-2-yl]piperidine-4-carboxylic acid (129 mg).

Example 206

To a mixture of ethyl 1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylate (695 mg), ethanol (5 mL), and tetrahydrofuran (5 mL) was added a 1 M aqueous sodium hydroxide solution (5 mL), followed by stirring at 50° C. for 30 minutes. To the reaction mixture was added acetic acid (0.29 mL), followed by concentration under reduced pressure and then addition of water (5 mL). The mixture was stirred at 50° C. for 3 hours, then cooled to room temperature, and stirred overnight, and the precipitated solid was then collected by filtration. The obtained solid and ethanol (4 mL) were mixed, followed by stirring at 80° C. for 30 minutes. The mixture was cooled to room temperature, followed by stirring for 18 hours. The solid was collected by filtration and dried to obtain crystals of 1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylic acid (567 mg).

The crystals obtained in Example 206 had peaks around 2θ (°) 4.8, 6.6, 9.1, 10.3, 13.3, 14.5, 15.7, 17.2, 18.3, 19.0, 24.7, and 26.0 in powder X-ray diffraction.

Example 207

To a mixture of ethyl 1-{5-[(4-[3-methoxy-5-(trifluoromethyl)phenyl]-5-{[(2R)-2-methylpiperidin-1-yl]methyl}-1, 3-thiazol-2-yl)carbamoyl]pyrazin-2-yl}piperidine-4-carboxylate (987 mg) and ethanol (5 mL) was added a 1 M aqueous sodium hydroxide solution (5 mL), followed by stirring at 50° C. for 30 minutes. To the reaction mixture were added acetic acid (0.29 mL) and water. The mixture was stirred at 50° C. for 3 hours, then cooled to room temperature, and stirred overnight, and the precipitated solid was collected by filtration. The obtained solid and ethanol (4 mL) were mixed, followed by stirring at 80° C. for 3 hours. The mixture was cooled to room temperature and stirred for 3 days. The precipitated solid was collected by filtration to obtain crystals of 1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid (275 mg).

The crystals obtained in Example 207 had peaks around 2θ (°) 4.7, 7.5, 9.6, 10.4, 13.7, 16.9, 17.1, 18.0, 18.3, 19.2, 20.1, and 25.9 in powder X-ray diffraction.

In the similar manner as the methods of Examples 1 to 8, the compounds of Example 9 to 205 in Tables below were prepared. For the compounds of Examples, the structures are shown in Tables 37 to 81, and the physicochemical data and the preparation methods are shown in Tables 82 to 97.

Furthermore, the structures of the other compounds of the formula (I) are shown in Tables 98 to 113. These can be easily prepared by the preparation the methods described in the Preparation Examples and the Examples above, the methods apparent to those skilled in the art, or modified methods thereof.

TABLE 4

| PEx | PSyn | Str | DATA |
|-----|------|-----|------|
| 1 | 1 | | ESI+: 247 |
| 2 | 2 | | ESI+: 233 |
| 3 | 3 | | ESI+: 247 |
| 4 | 4 | | ESI+: 235 |
| 5 | 5 | | ESI+: 275 |
| 6 | 6 | | ESI−: 278 |

TABLE 4-continued
| PEx | PSyn | Str | DATA |
|---|---|---|---|
| 7 | 7 | 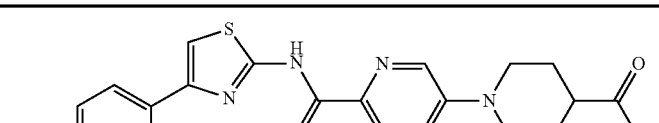 | ESI+: 564 |
| 8 | 8 | | ESI+: 246 |
TABLE 5
| PEx | PSyn | Str | DATA |
|---|---|---|---|
| 9 | 9 | 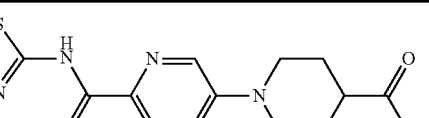 | ESI+: 536 |
| 10 | 10 | | ESI+: 512 |
| 11 | 11 | | ESI+: 415 |
| 12 | 12 | | ESI+: 574 |

TABLE 5-continued
| PEx | PSyn | Str | DATA |
|---|---|---|---|
| 13 | 13 | 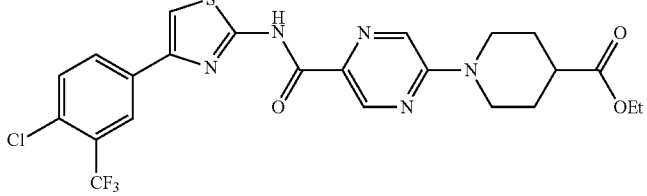 | ESI+: 681 |
| 14 | 14 | 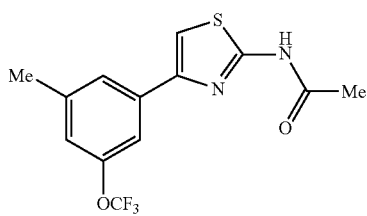 [SMILES: CC(=O)Nc1nc(-c2cc(C)cc(OC(F)(F)F)c2)cs1] | ESI+: 536 |
TABLE 6
| PEx | PSyn | Str | DATA |
|---|---|---|---|
| 15 | 15 | 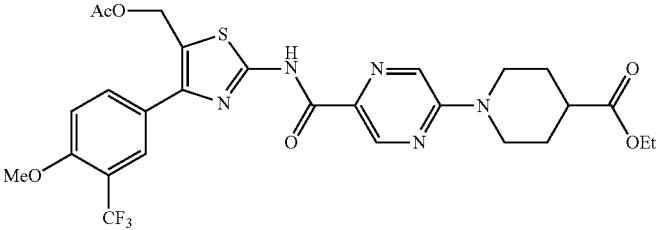 [SMILES: CCOC(=O)C1CCN(c2cnc(C(=O)Nc3nc(-c4ccc(OC)c(C(F)(F)F)c4)c(COC(C)=O)s3)cn2)CC1] | ESI+: 540 |
| 16 | 16 | | ESI+: 317 |
| 17 | 17 | | ESI+: 608 |

TABLE 6-continued
| PEx | PSyn | Str | DATA |
|---|---|---|---|
| 18 | 18 | 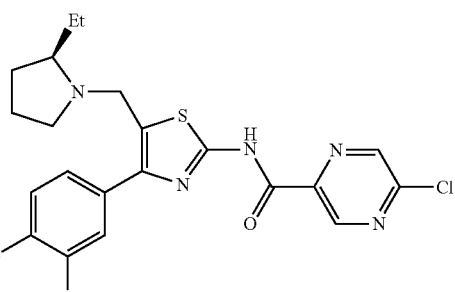 | ESI+: 608 |
| 19 | 19 | | ESI+: 636 |
| 20 | 20 | | ESI+: 612, 614 |
TABLE 7
| PEx | PSyn | Str | DATA |
|---|---|---|---|
| 21 | 21 | 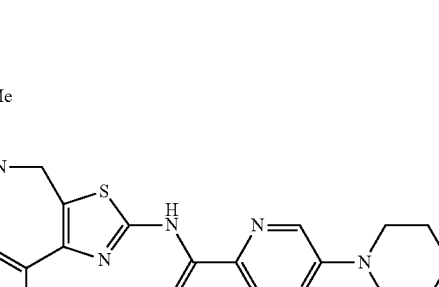 | ESI+: 526 |
| 22 | 22 | | ESI+: 646 |

TABLE 7-continued

| PEx | PSyn | Str | DATA |
|---|---|---|---|
| 23 | 23 | (structure) | ESI+: 647 |
| 24 | 24 | (structure) | ESI+: 637, 639 |
| 25 | 25 | (structure) | ESI+: 144 |
| 26 | 26 | (structure) | ESI+: 100 |

TABLE 8

| PEx | PSyn | Str | DATA |
|---|---|---|---|
| 27 | 27 | (structure) | ESI+: 372 |
| 28 | 28 | (structure) | ESI+: 275 |
| 29 | 29 | (structure) | ESI+: 228 |
| 30 | 30 | (structure) | EI: 274 |

TABLE 8-continued

| PEx | PSyn | Str | DATA |
|---|---|---|---|
| 31 | 31 | [structure] | ESI+: 258 |
| 32 | 32 | [structure] | ESI+: 353 |
| 33 | 33 | [structure] | ESI+: 313 |

TABLE 9

| PEx | PSyn | Str | DATA |
|---|---|---|---|
| 34 | 34 | [structure] | ESI+: 341 |
| 35 | 35 | [structure] | ESI+: 216 |
| 36 | 36 | [structure] | ESI+: 264 |
| 37 | 37 | [structure] | ESI+: 314 |

TABLE 9-continued

| PEx | PSyn | Str | DATA |
|---|---|---|---|
| 38 | 38 | [structure] | ESI−: 309 |
| 39 | 39 | [structure] | NMR-DMSO-d6: 3.82 (3H, s), 6.97-7.00 (1H, m), 7.18-7.21 (1H, m), 7.23-7.26 (1H, m) |
| 40 | 40 | [structure] | ESI+: 278 |

TABLE 10

| PEx | PSyn | Str | DATA |
|---|---|---|---|
| 41 | 41 | [structure] | ESI+: 272 |
| 42 | 42 | [structure] | ESI+: 244 |
| 43 | 43 | [structure] | ESI+: 402 |
| 44 | 44 | [structure] | ESI−: 196 |

TABLE 10-continued

| PEx | PSyn | Str | DATA |
|---|---|---|---|
| 45 | 45 | 2-acetyl-4-(trifluoromethyl)thiazole | EI: 195 |
| 46 | 46 | (S)-1-Boc-2-(tosyloxymethyl)pyrrolidine | ESI+: 378 [M + Na]+ |
| 47 | 47 | (S)-1-Boc-2-ethylpyrrolidine | ESI+: 200 |
| 48 | 48 | 1-Boc-3-(ethoxycarbonyl)-3-(methoxycarbonyl)piperidine | ESI+: 316 |

TABLE 11

| PEx | PSyn | Str | DATA |
|---|---|---|---|
| 49 | 1 | 1-(4-(3-methoxypropoxy)-3-(trifluoromethyl)phenyl)ethan-1-one | ESI+: 277 |
| 50 | 3 | 1-(4-(3-fluoropropoxy)-3-(trifluoromethyl)phenyl)ethan-1-one | ESI+: 265 |
| 51 | 3 | 1-(4-(2-methoxyethoxy)-3-(trifluoromethyl)phenyl)ethan-1-one | ESI+: 263 |
| 52 | 4 | 1-(3-fluoro-4-methoxy-5-(trifluoromethyl)phenyl)ethan-1-one | ESI+: 237 |

TABLE 11-continued

| PEx | PSyn | Str | DATA |
|---|---|---|---|
| 53 | 4 | 1-(4-methoxy-3-(trifluoromethoxy)phenyl)ethan-1-one | ESI+: 235 |
| 54 | 5 | 4-(4-fluoro-3-(trifluoromethyl)phenyl)thiazol-2-amine | ESI+: 263 |
| 55 | 5 | 4-(3-fluoro-4-methoxyphenyl)thiazol-2-amine | ESI+: 225 |

TABLE 12

| PEx | PSyn | Str | DATA |
|---|---|---|---|
| 56 | 5 | 4-(3,4-dimethylphenyl)thiazol-2-amine | ESI+: 205 |
| 57 | 5 | 4-(3-chloro-4-methoxyphenyl)thiazol-2-amine | ESI+: 241 |
| 58 | 5 | 4-(3,5-bis(trifluoromethyl)phenyl)thiazol-2-amine | ESI+: 313 |
| 59 | 5 | 4-(3-methyl-4-(trifluoromethyl)phenyl)thiazol-2-amine | ESI+: 259 |

TABLE 12-continued

| PEx | PSyn | Str | DATA |
|---|---|---|---|
| 60 | 5 | 4-(3-methoxy-5-(trifluoromethyl)phenyl)thiazol-2-amine | ESI+: 275 |
| 61 | 5 | 4-(4-fluoro-3-(trifluoromethoxy)phenyl)thiazol-2-amine | ESI+: 279 |
| 62 | 5 | 4-(3-methyl-5-(trifluoromethoxy)phenyl)thiazol-2-amine | ESI+: 275 |

TABLE 13

| PEx | PSyn | Str | DATA |
|---|---|---|---|
| 63 | 5 | 4-(3-chloro-5-fluoro-4-methoxyphenyl)thiazol-2-amine | ESI+: 259 |
| 64 | 5 | 4-(3-methoxy-5-(trifluoromethoxy)phenyl)thiazol-2-amine | ESI+: 291 |
| 65 | 5 | 4-(4-methoxy-3,5-dimethylphenyl)thiazol-2-amine | ESI+: 235 |

TABLE 13-continued

| PEx | PSyn | Str | DATA |
|---|---|---|---|
| 66 | 5 | 4-(3,5-difluoro-4-methoxyphenyl)thiazol-2-amine | ESI+: 243 |
| 67 | 5 | 4-(3-fluoro-4-methoxy-5-(trifluoromethyl)phenyl)thiazol-2-amine | ESI+: 293 |
| 68 | 5 | 4-(3,5-dichloro-4-methoxyphenyl)thiazol-2-amine | ESI+: 275 |
| 69 | 5 | 4-(5-chlorothiophen-3-yl)thiazol-2-amine | ESI+: 217 |

TABLE 14

| PEx | PSyn | Str | DATA |
|---|---|---|---|
| 70 | 5 | 4-(4-(dimethylamino)-3-(trifluoromethyl)phenyl)thiazol-2-amine | ESI+: 288 |
| 71 | 5 | 4-(3-fluoro-4-(trifluoromethyl)phenyl)thiazol-2-amine | ESI+: 263 |
| 72 | 5 | 4-(3,5-dichlorophenyl)thiazol-2-amine | ESI+: 245, 247 |

TABLE 14-continued

| PEx | PSyn | Str | DATA |
|---|---|---|---|
| 73 | 5 | 3-(trifluoromethyl)-4-(pyrrolidin-1-yl)phenyl thiazol-2-amine | ESI+: 314 |
| 74 | 5 | 3-(trifluoromethyl)-4-morpholinophenyl thiazol-2-amine | ESI+: 330 |
| 75 | 5 | (S)-tetrahydrofuran-3-yloxy-3-(trifluoromethyl)phenyl thiazol-2-amine | ESI+: 331 |
| 76 | 5 | (R)-tetrahydrofuran-3-yloxy-3-(trifluoromethyl)phenyl thiazol-2-amine | ESI+: 331 |

TABLE 15

| PEx | PSyn | Str | DATA |
|---|---|---|---|
| 77 | 5 | 4-(trifluoromethyl)thiazol-2-yl thiazol-2-amine | ESI+: 252 |

TABLE 15-continued

| PEx | PSyn | Str | DATA |
|---|---|---|---|
| 78 | 5 | 4-methylthiophen-2-yl thiazol-2-amine | ESI+: 197 |
| 79 | 5 | 4-isopropoxy-3-(trifluoromethyl)phenyl thiazol-2-amine | ESI+: 303 |
| 80 | 5 | 4-propoxy-3-(trifluoromethyl)phenyl thiazol-2-amine | ESI+: 303 |
| 81 | 5 | 4-(3-methoxypropoxy)-3-(trifluoromethyl)phenyl thiazol-2-amine | ESI+: 333 |
| 82 | 5 | 2,3-dihydrobenzofuran-5-yl thiazol-2-amine | ESI+: 219 |
| 83 | 5 | 3-fluoro-5-(trifluoromethyl)phenyl thiazol-2-amine | ESI+: 263 |

TABLE 16

| PEx | PSyn | Str | DATA |
|---|---|---|---|
| 84 | 5 | 4-methoxy-3-(trifluoromethoxy)phenyl thiazol-2-amine | ESI+: 291 |

TABLE 16-continued
| PEx | PSyn | Str | DATA |
|---|---|---|---|
| 85 | 5 | 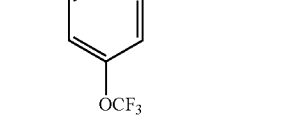 | ESI+: 295 |
| 86 | 5 | 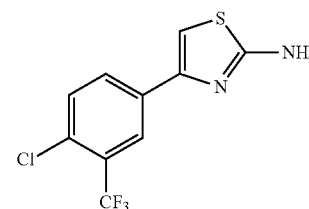 | ESI+: 279, 281 |
| 87 | 5 | 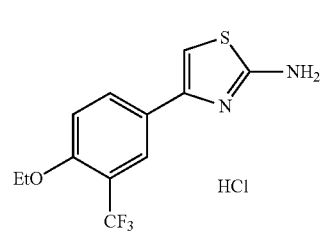 [SMILES: CCOc1ccc(-c2csc(N)n2)cc1C(F)(F)F ; Cl] | ESI+: 289 |
| 88 | 5 | 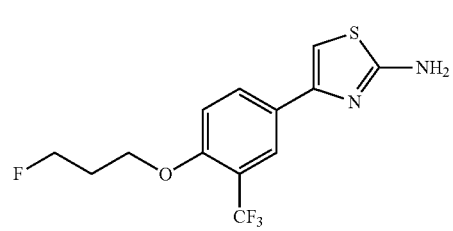 [SMILES: Nc1nc(-c2ccc(OCCCF)c(C(F)(F)F)c2)cs1] | ESI+: 321 |
| 89 | 5 | 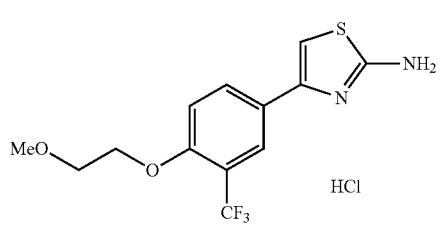 [SMILES: COCCOc1ccc(-c2csc(N)n2)cc1C(F)(F)F ; Cl] | ESI+: 319 |
| 90 | 7 | 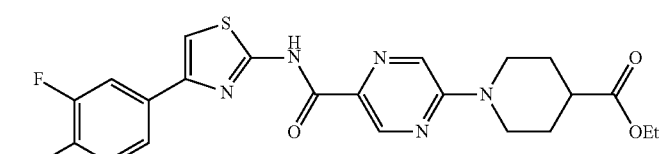 | ESI+: 486 |
TABLE 17
| PEx | PSyn | Str | DATA |
|---|---|---|---|
| 91 | 7 | | ESI+: 466 |

TABLE 17-continued
| PEx | PSyn | Str | DATA |
|---|---|---|---|
| 92 | 92 | | ESI+: 536 |
| 93 | 7 | | ESI+: 564 |
| 94 | 7 | | ESI+: 594 |
| 95 | 7 | | ESI+: 480 |
| 96 | 8 | | ESI+: 230 |
| 97 | 9 | | ESI+: 540 |
TABLE 18
| PEx | PSyn | Str | DATA |
|---|---|---|---|
| 98 | 9 | | ESI+: 502 |
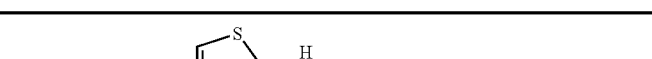

TABLE 18-continued

| PEx | PSyn | Str | DATA |
|---|---|---|---|
| 99 | 9 | 4-(3-fluoro-5-chloro-4-methoxyphenyl)thiazol-2-yl pyrazine-piperidine-CO2Et | ESI+: 520 |
| 100 | 9 | 4-(3-methoxy-5-trifluoromethoxyphenyl)thiazol-2-yl pyrazine-piperidine-CO2Et | ESI+: 552 |
| 101 | 9 | 4-(3,5-dimethyl-4-methoxyphenyl)thiazol-2-yl pyrazine-piperidine-CO2Et | ESI+: 496 |
| 102 | 9 | 4-(3-trifluoromethyl-4-difluoromethoxyphenyl)thiazol-2-yl pyrazine-piperidine-CO2Et | ESI+: 572 |
| 103 | 9 | 4-(3,5-difluoro-4-methoxyphenyl)thiazol-2-yl pyrazine-piperidine-CO2Et | ESI+: 504 |
| 104 | 9 | 4-(3-fluoro-5-trifluoromethyl-4-methoxyphenyl)thiazol-2-yl pyrazine-piperidine-CO2Et | ESI+: 554 |

TABLE 19

| PEx | PSyn | Str | DATA |
|---|---|---|---|
| 105 | 9 | | ESI+: 536 |
| 106 | 9 | | ESI+: 549 |
| 107 | 9 | | ESI+: 524 |
| 108 | 9 | | ESI+: 536 |
| 109 | 9 | | ESI+: 506, 508 |
| 110 | 9 | | ESI+: 591 |
| 111 | 9 | | ESI+: 575 |

TABLE 20

| PEx | PSyn | Str | DATA |
|---|---|---|---|
| 112 | 9 | | ESI+: 592 |
| 113 | 9 | | ESI+: 592 |
| 114 | 9 | | ESI+: 513 |
| 115 | 9 | | ESI+: 458 |
| 116 | 9 | | ESI+: 552 |
| 117 | 9 | | ESI+: 478, 480 |
| 118 | 9 | | ESI+: 524 |

TABLE 21
| PEx | PSyn | Str | DATA |
|---|---|---|---|
| 119 | 9 | 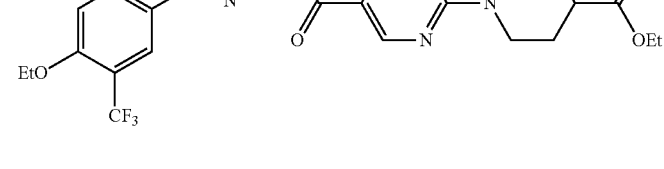 | ESI+: 550 |
| 120 | 9 | 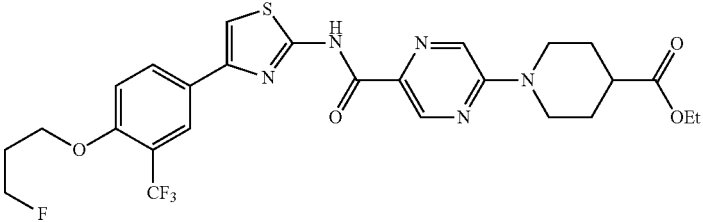 [SMILES: CCOC(=O)C1CCN(c2cnc(C(=O)Nc3nc(-c4ccc(OCCCF)c(C(F)(F)F)c4)cs3)cn2)CC1] | ESI+: 582 |
| 121 | 9 | 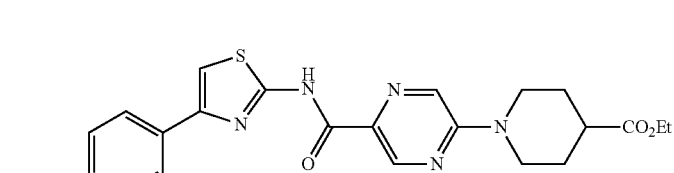 | ESI+: 580 |
| 122 | 10 | 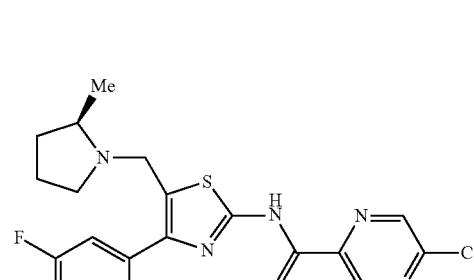 | ESI+: 500 |
| 123 | 10 | 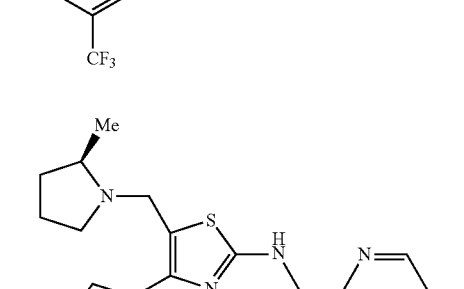 | ESI+: 454 |

TABLE 22
| PEx | PSyn | Str | DATA |
|---|---|---|---|
| 124 | 10 | 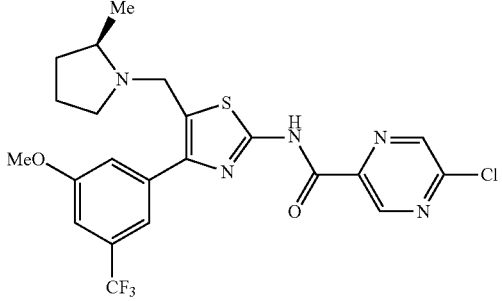 [SMILES: COc1cc(-c2nc(NC(=O)c3cnc(Cl)cn3)sc2CN2CCC[C@H]2C)cc(C(F)(F)F)c1] | ESI+: 512 |
| 125 | 10 | 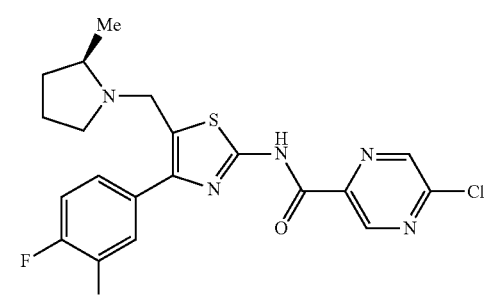 | ESI+: 500 |
| 126 | 10 | 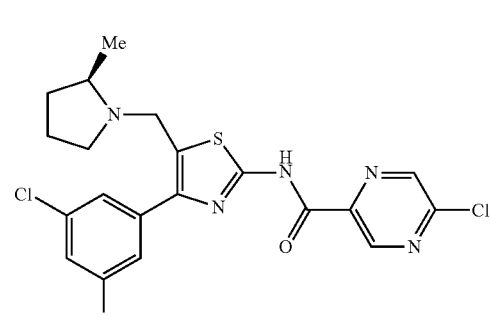 | ESI+: 516, 518 |
| 127 | 14 | 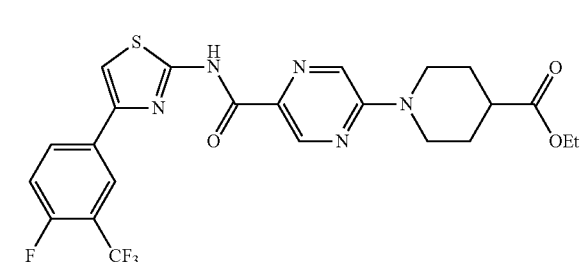 | ESI+: 524 |
| 128 | 15 | 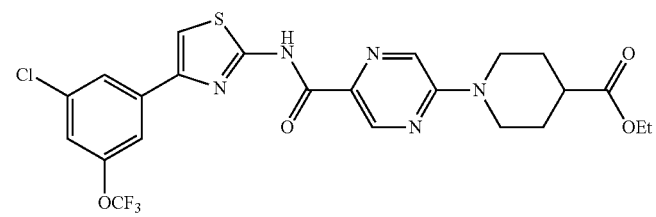 [SMILES: CCOC(=O)C1CCN(c2cnc(C(=O)Nc3nc(-c4cc(Cl)cc(OC(F)(F)F)c4)cs3)cn2)CC1] | ESI+: 556 |

TABLE 23

| PEx | PSyn | Str | DATA |
|---|---|---|---|
| 129 | 15 | | ESI+: 520 |
| 130 | 16 | | ESI+: 305 |
| 131 | 16 | | ESI+: 259 |
| 132 | 16 | | ESI+: 317 |
| 133 | 16 | | ESI+: 305 |
| 134 | 16 | | ESI+: 321 |
| 135 | 17 | | ESI+: 576 |

TABLE 24

| PEx | PSyn | Str | DATA |
|---|---|---|---|
| 136 | 17 | | ESI+: 647 |
| 137 | 17 | | ESI+: 664 |
| 138 | 17 | | ESI+: 664 |
| 139 | 17 | | ESI+: 636 |
| 140 | 17 | | ESI+: 666 |
| 141 | 17 | | ESI+: 552 |

TABLE 25

| PEx | PSyn | Str | DATA |
|-----|------|-----|------|
| 142 | 17 | (structure) | ESI+: 624 |
| 143 | 18 | (structure) | ESI+: 393 |
| 144 | 18 | (structure) | ESI+: 628 |
| 145 | 18 | (structure) | ESI+: 612 |
| 146 | 18 | (structure) | ESI+: 608 |
| 147 | 18 | (structure) | ESI+: 574 |

TABLE 26

| PEx | PSyn | Str | DATA |
|---|---|---|---|
| 148 | 18 | 4-(4-(3-chloro-5-fluoro-4-methoxyphenyl)-5-(acetoxymethyl)thiazol-2-ylcarbamoyl)pyrazin-2-yl piperidine-4-carboxylic acid ethyl ester | ESI+: 592 |
| 149 | 18 | 4-(4-(3-methoxy-5-(trifluoromethoxy)phenyl)-5-(acetoxymethyl)thiazol-2-ylcarbamoyl)pyrazin-2-yl piperidine-4-carboxylic acid ethyl ester | ESI+: 624 |
| 150 | 18 | 4-(4-(4-methoxy-3,5-dimethylphenyl)-5-(acetoxymethyl)thiazol-2-ylcarbamoyl)pyrazin-2-yl piperidine-4-carboxylic acid ethyl ester | APCI/ESI+: 568 |
| 151 | 18 | 4-(4-(4-(difluoromethoxy)-3-(trifluoromethyl)phenyl)-5-(acetoxymethyl)thiazol-2-ylcarbamoyl)pyrazin-2-yl piperidine-4-carboxylic acid ethyl ester | ESI+: 644 |
| 152 | 18 | 4-(4-(3-fluoro-4-methoxy-5-(trifluoromethyl)phenyl)-5-(acetoxymethyl)thiazol-2-ylcarbamoyl)pyrazin-2-yl piperidine-4-carboxylic acid ethyl ester | ESI+: 626 |
| 153 | 18 | 4-(4-(3-methoxy-4-(trifluoromethyl)phenyl)-5-(acetoxymethyl)thiazol-2-ylcarbamoyl)pyrazin-2-yl piperidine-4-carboxylic acid ethyl ester | ESI+: 608 |
| 154 | 18 | 4-(4-(3,5-dichloro-4-methoxyphenyl)-5-(acetoxymethyl)thiazol-2-ylcarbamoyl)pyrazin-2-yl piperidine-4-carboxylic acid ethyl ester | ESI+: 608 |

TABLE 27
| PEx | PSyn | Str | DATA |
|---|---|---|---|
| 155 | 18 | 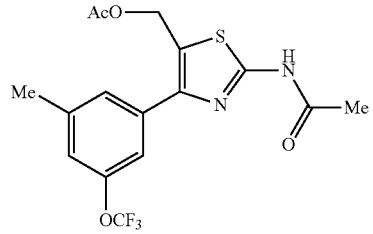 [SMILES: CC(=O)Nc1nc(-c2cc(C)cc(OC(F)(F)F)c2)c(COC(C)=O)s1] | ESI+: 389 |
| 156 | 18 | 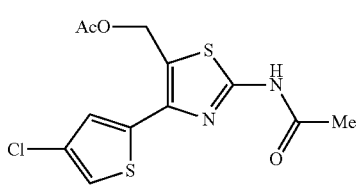 [SMILES: CC(=O)Nc1nc(-c2cc(Cl)cs2)c(COC(C)=O)s1] | ESI+: 331 |
| 157 | 18 | 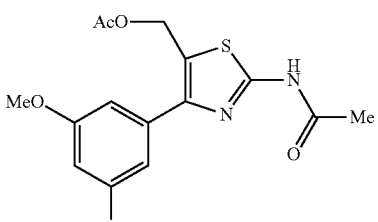 | ESI+: 389 |
| 158 | 18 | 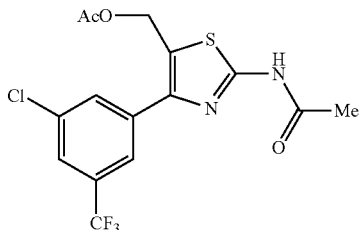 | ESI+: 393, 395 |
| 159 | 18 | 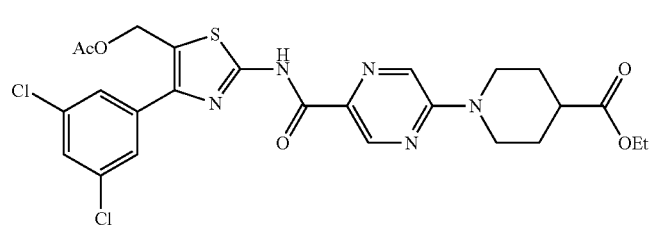 [SMILES: CCOC(=O)C1CCN(c2cnc(C(=O)Nc3nc(-c4cc(Cl)cc(Cl)c4)c(COC(C)=O)s3)cn2)CC1] | ESI+: 578, 580 |
| 160 | 18 | 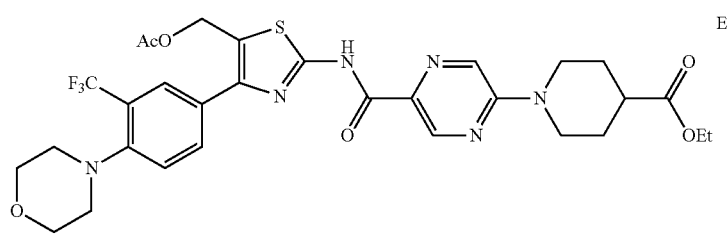 | ESI+: 663 |

TABLE 28

| PEx | PSyn | Str | DATA |
|---|---|---|---|
| 161 | 18 | | ESI+: 596 |
| 162 | 19 | | APCI/ESI+: 558 |
| 163 | 19 | | ESI+: 538 |
| 164 | 20 | | ESI+: 596 |
| 165 | 22 | | ESI+: 621 |
| 166 | 22 | | ESI+: 633 |

TABLE 29
| PEx | PSyn | Str | DATA |
|---|---|---|---|
| 167 | 23 | | ESI+: 414 |
| 168 | 23 | | ESI+: 356 |
| 169 | 23 | | ESI+: 414 |
TABLE 29-continued
| PEx | PSyn | Str | DATA |
|---|---|---|---|
| 170 | 23 | | ESI+: 462 |
| 171 | 23 | | ESI+: 418, 420 |
TABLE 30
| PEx | PSyn | Str | DATA |
|---|---|---|---|
| 172 | 23 | | ESI+: 675 |
| 173 | 23 | | ESI+: 689 |
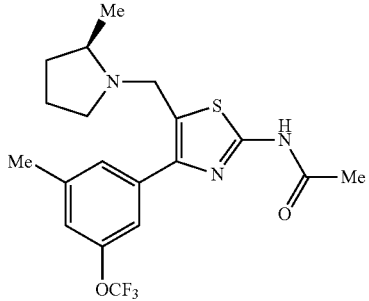 [SMILES: CC(=O)Nc1nc(-c2cc(C)cc(OC(F)(F)F)c2)c(CN2CCC[C@H]2C)s1]
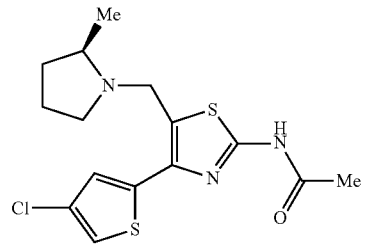 [SMILES: CC(=O)Nc1nc(-c2cc(Cl)cs2)c(CN2CCC[C@H]2C)s1]
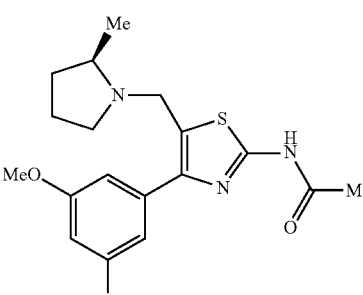
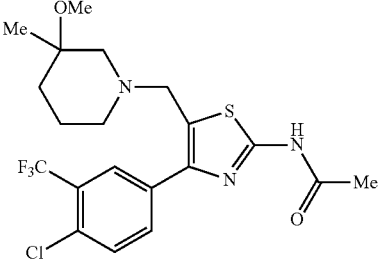 [SMILES: COC1(C)CCCN(Cc2sc(NC(C)=O)nc2-c2ccc(Cl)c(C(F)(F)F)c2)C1]
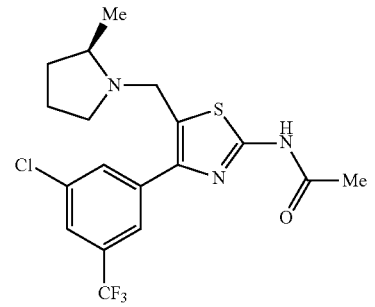 [SMILES: CC(=O)Nc1nc(-c2cc(Cl)cc(C(F)(F)F)c2)c(CN2CCC[C@H]2C)s1]
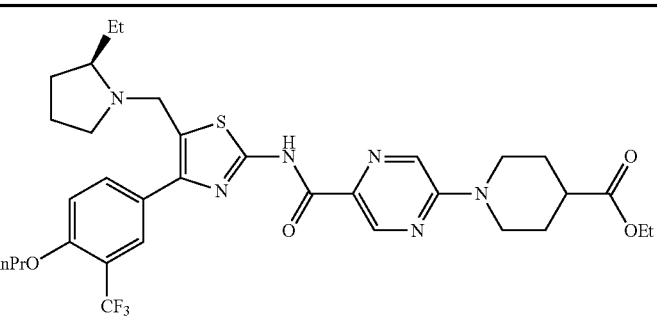
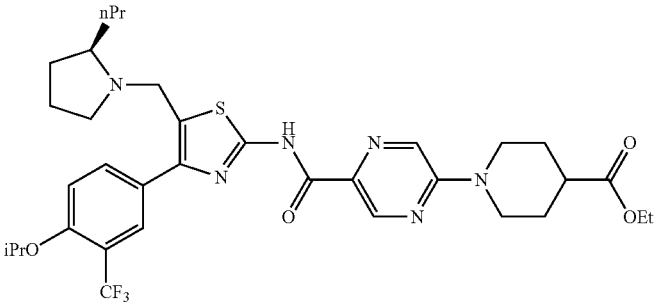 [SMILES: CCOC(=O)C1CCN(c2cnc(C(=O)Nc3nc(-c4ccc(OC(C)C)c(C(F)(F)F)c4)c(CN4CCC[C@H]4CC)s3)cn2)CC1]

TABLE 30-continued
| PEx | PSyn | Str | DATA |
|---|---|---|---|
| 174 | 23 | | ESI+: 675 |
| 175 | 23 | | ESI+: 689 |
| 176 | 23 | | ESI+: 675 |
TABLE 31
| PEx | PSyn | Str | DATA |
|---|---|---|---|
| 177 | 23 | | ESI+: 689 |
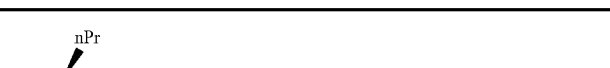

TABLE 31-continued
| PEx | PSyn | Str | DATA |
|---|---|---|---|
| 178 | 23 | 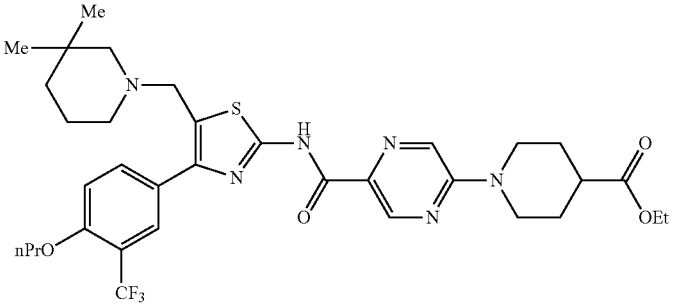 [SMILES: CCOC(=O)C1CCN(c2cnc(C(=O)Nc3nc(-c4ccc(OC(C)C)c(C(F)(F)F)c4)c(CN4CCCC(C)(C)C4)s3)cn2)CC1] | ESI+: 689 |
| 179 | 23 | 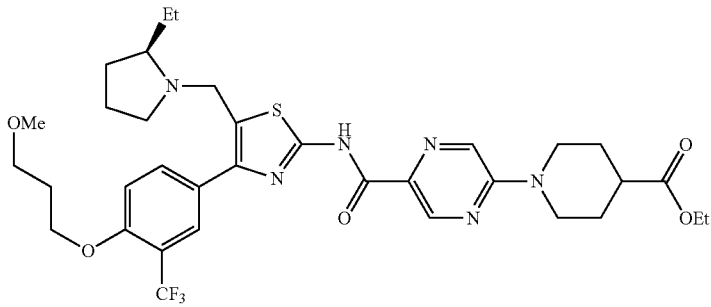 | ESI+: 705 |
| 180 | 23 | 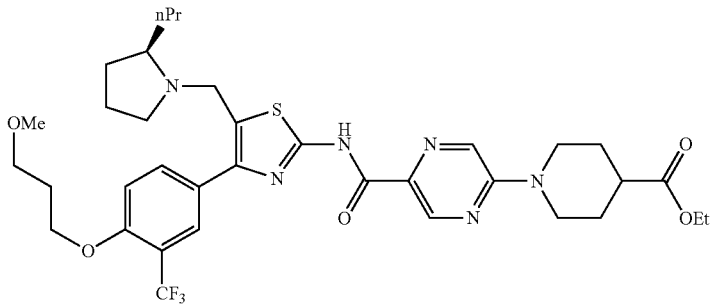 [SMILES: CCOC(=O)C1CCN(c2cnc(C(=O)Nc3nc(-c4ccc(OCCCOC)c(C(F)(F)F)c4)c(CN4CCC[C@H]4CC)s3)cn2)CC1] | ESI+: 719 |
| 181 | 23 | 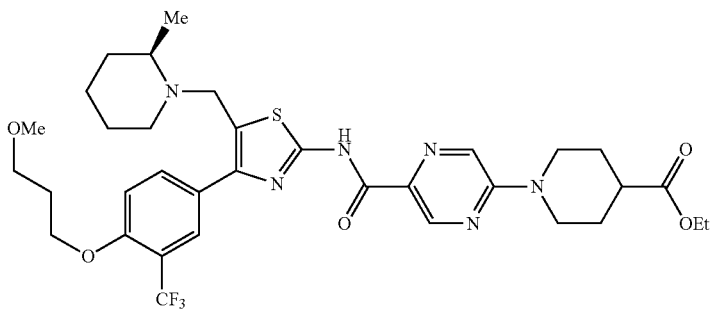 [SMILES: CCOC(=O)C1CCN(c2cnc(C(=O)Nc3nc(-c4ccc(OCCCOC)c(C(F)(F)F)c4)c(CN4CCCC[C@H]4C)s3)cn2)CC1] | ESI+: 705 |

TABLE 32

| PEx | PSyn | Str | DATA |
|---|---|---|---|
| 182 | 23 | | ESI+: 719 |
| 183 | 23 | | ESI+: 591 |
| 184 | 23 | | ESI+: 605 |
| 185 | 23 | | ESI+: 647 |
| 186 | 24 | | ESI+: 669, 671 |

TABLE 32-continued
| PEx | PSyn | Str | DATA |
|---|---|---|---|
| 187 | 24 |  | ESI+: 677 |
TABLE 33
| PEx | PSyn | Str | DATA |
|---|---|---|---|
| 188 | 26 | (3-methyl-piperidin-3-yl)methanol HCl | ESI+: 130 |
| 189 | 26 | 3-(methoxymethyl)-3-methylpiperidine HCl | ESI+: 144 |
| 190 | 26 | 2-(methoxymethyl)-2-methylpyrrolidine HCl | ESI+: 130 |
| 191 | 26 | (2S)-2-ethylpyrrolidine HCl | ESI+: 100 |
| 192 | 27 | thiazole derivative | ESI+: 360 |
| 193 | 27 | thiazole derivative | ESI−: 312 |
| 194 | 27 |  | ESI+: 372 |
TABLE 34
| PEx | PSyn | Str | DATA |
|---|---|---|---|
| 195 | 27 | thiazole derivative | ESI+: 360 |
| 196 | 27 | thiazole derivative | ESI+: 420 |

TABLE 34-continued
| PEx | PSyn | Str | DATA |
|---|---|---|---|
| 197 | 27 | 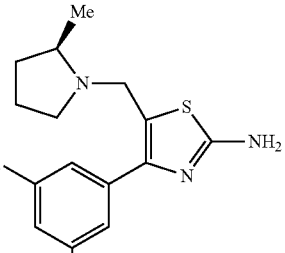 | ESI+: 376, 378 |
| 198 | 30 | 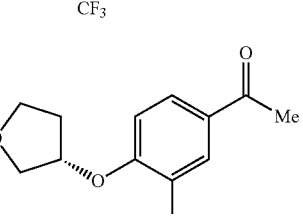 | EI: 274 |"
| 199 | 31 | 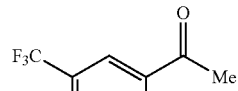 | ESI+: 274 |
| 200 | 39 |  | ESI+: 179 |
TABLE 35
| PEx | PSyn | Str | DATA |
|---|---|---|---|
| 201 | 39 | 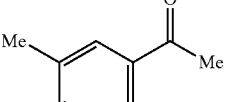 | ESI+: 219 |
| 202 | 40 | 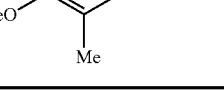 | ESI+: 230 |
| 203 | 43 | 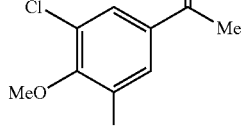 | ESI+: 402 |
| 204 | 46 | 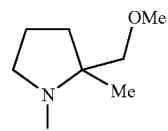 | ESI+: 356 |
| 205 | 47 | 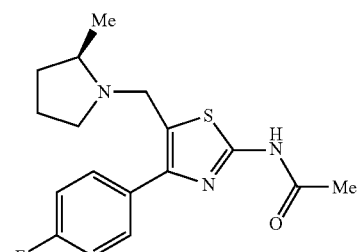 | CI+: 200 |

TABLE 35-continued

| PEx | PSyn | Str | DATA |
|---|---|---|---|
| 206 | 5 | 4-(3-chloro-5-(trifluoromethyl)phenyl)thiazol-2-amine | ESI+: 279 |
| 207 | 23 | (S)-2-methylpiperidine thiazole with iPrO/CF3 phenyl, pyrazine carboxamide, piperidine ethyl ester | ESI+: 675 |

TABLE 36

| PEx | PSyn | Str | DATA |
|---|---|---|---|
| 208 | 16 | N-(4-(4-chloro-3-(trifluoromethyl)phenyl)thiazol-2-yl)acetamide | ESI+: 321 |
| 209 | 209 | 1-(4-(dimethylamino)-3-(trifluoromethyl)phenyl)ethanone | ESI+: 232 |
| 210 | 21 | (S)-2-methylpyrrolidine thiazole with 4-chlorothiophene, pyrazine carboxamide, piperidine ethyl ester | ESI−: 573, 575 |

TABLE 36-continued

| PEx | PSyn | Str | DATA |
|---|---|---|---|
| 211 | 23 | (structure) | ESI+: 647 |
| 212 | 26 | (structure) | ESI+: 130 |

TABLE 37

| Ex | Str |
|---|---|
| 1 | (structure) 2HCl |
| 2 | (structure) 2HCl |
| 3 | (structure) 2HCl |

TABLE 37-continued
| Ex | Str |
|---|---|
| 4 | 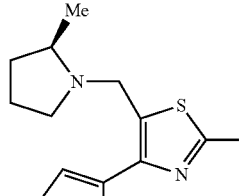 2HCl |
| 5 | 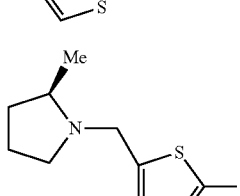 2HCl |
TABLE 38
| Ex | Str |
|---|---|
| 6 | 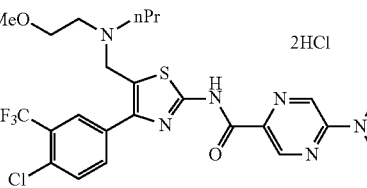 |
| 7 | |
| 8 | |
TABLE 38-continued
| Ex | Str |
|---|---|
| 9 | 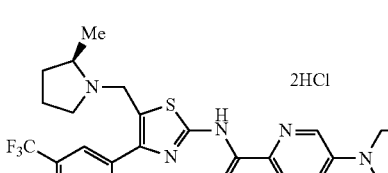 2HCl |
| 10 | Me, 2HCl |
TABLE 39
| Ex | Str |
|---|---|
| 11 | Me, 3HCl |

TABLE 39-continued
| Ex | Str |
|---|---|
| 12 |  |
| 13 | |
| 14 | |
| 15 | |
TABLE 40
| Ex | Str |
|---|---|
| 16 | |
| 17 | 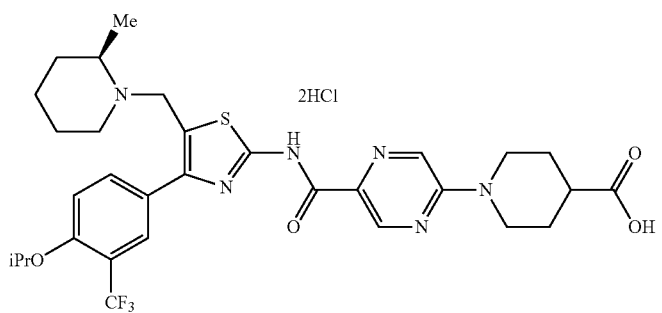 [SMILES: CC(C)Oc1ccc(-c2nc(NC(=O)c3cnc(N4CCC(C(=O)O)CC4)cn3)sc2CN2CCCC[C@H]2C)cc1C(F)(F)F ; "2HCl"] |
| 18 | 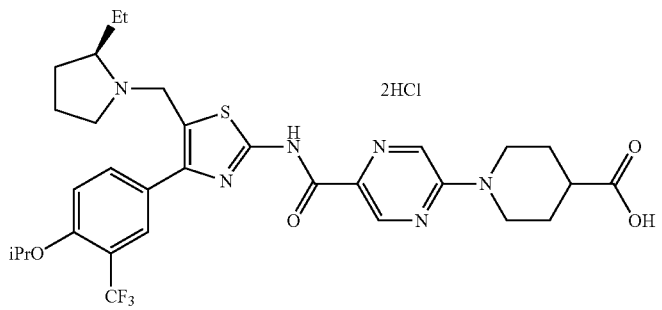 [SMILES: CC[C@@H]1CCCN1Cc1sc(NC(=O)c2cnc(N3CCC(C(=O)O)CC3)cn2)nc1-c1ccc(OC(C)C)c(C(F)(F)F)c1 ; "2HCl"] |

TABLE 40-continued
| Ex | Str |
|---|---|
| 19 |  |
TABLE 41
| Ex | Str |
|---|---|
| 20 | 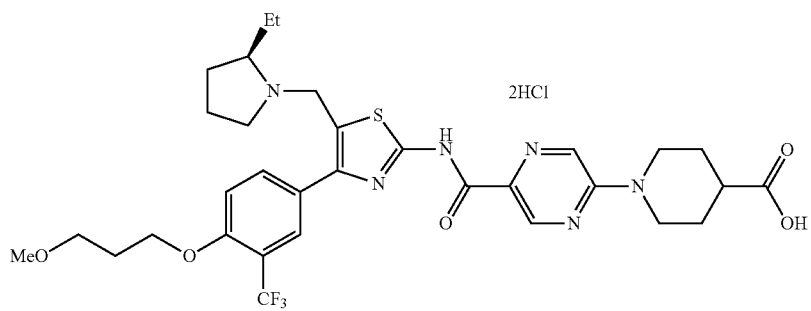 [SMILES: CC[C@@H]1CCCN1Cc1sc(NC(=O)c2cnc(N3CCC(C(=O)O)CC3)cn2)nc1-c1ccc(OCCCOC)c(C(F)(F)F)c1 ; "2HCl"] |
| 21 | 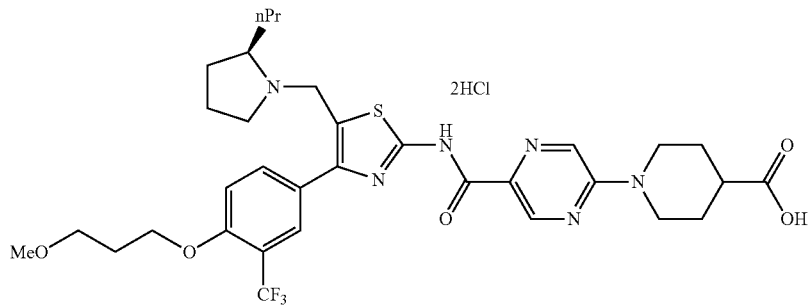 |
| 22 | |

TABLE 41-continued
| Ex | Str |
|---|---|
| 23 | 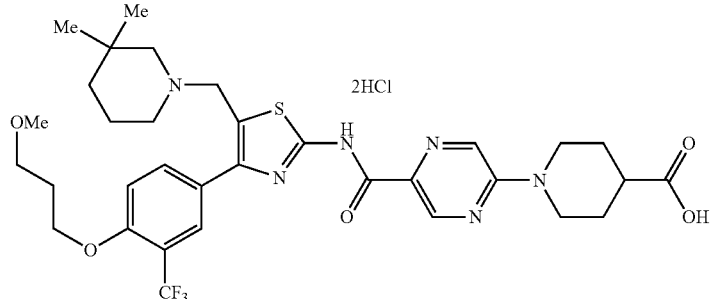 |
TABLE 42
| Ex | Str |
|---|---|
| 24 | 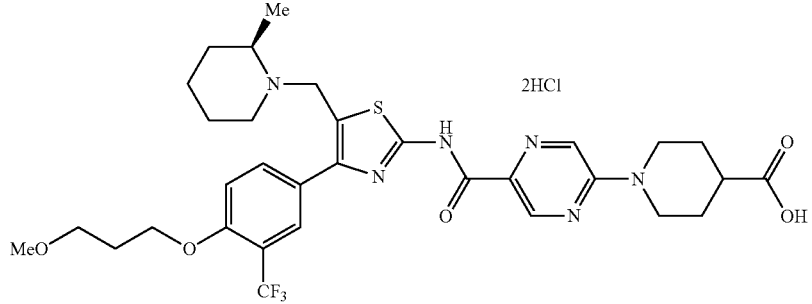 [SMILES: COCCCOc1ccc(-c2nc(NC(=O)c3cnc(N4CCC(C(=O)O)CC4)cn3)sc2CN2CCCC[C@H]2C)cc1C(F)(F)F ; "2HCl"] |
| 25 | 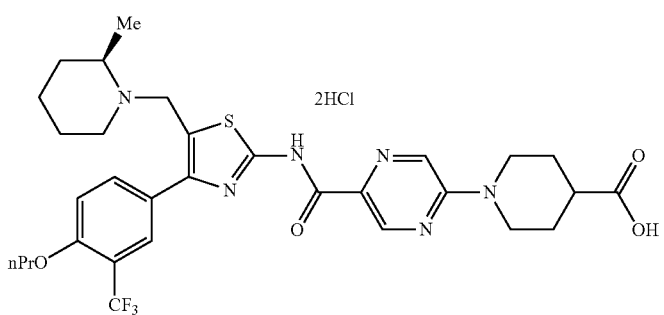 |
| 26 | 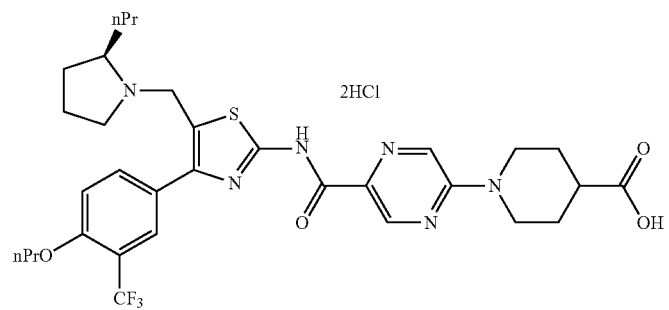 |

TABLE 42-continued

| Ex | Str |
|---|---|
| 27 | (structure, 2HCl) |
| 28 | (structure, HCl) |

TABLE 43

| Ex | Str |
|---|---|
| 29 | (structure, HCl) |
| 30 | (structure, 2HCl) |
| 31 | (structure, 2HCl) |
| 32 | (structure, 2HCl) |
| 33 | (structure, 2HCl) |

TABLE 44

| Ex | Str |
|---|---|
| 34 | (structure, 2HCl) |

TABLE 44-continued

| Ex | Str |
|---|---|
| 35 | (structure with nPr-pyrrolidine, thiazole, 4-fluoro-3-CF₃-phenyl, pyrazine carboxamide, piperidine-4-carboxylic acid) 2HCl |
| 36 | (structure with 3,3-dimethylpiperidine, thiazole, 3-fluoro-4-methoxyphenyl, pyrazine carboxamide, piperidine-4-carboxylic acid) 2HCl |
| 37 | (structure with 2-ethylpyrrolidine, thiazole, 3,4-dimethylphenyl, pyrazine carboxamide, piperidine-4-carboxylic acid) 2HCl |
| 38 | (structure with MeOCH₂CH₂N(iBu)-, thiazole, 3,5-bis(CF₃)phenyl, pyrazine carboxamide, piperidine-4-carboxylic acid) 2HCl |

TABLE 45

| Ex | Str |
|---|---|
| 39 | (structure with 3,3-dimethylpiperidine, thiazole, 4-chloro-3-CF₃-phenyl, pyrazine carboxamide, piperidine-4-carboxylic acid) 2HCl |
| 40 | (structure with 2-ethylpyrrolidine, thiazole, 3-chloro-5-OCF₃-phenyl, pyrazine carboxamide, piperidine-4-carboxylic acid) 2HCl |

TABLE 45-continued

| Ex | Str |
|---|---|
| 41 | (structure with nPr-pyrrolidine, thiazole, 3-chloro-5-OCF₃-phenyl, pyrazine carboxamide, piperidine-4-carboxylic acid) 2HCl |
| 42 | (structure with iBu-N-CH₂CH₂OMe, thiazole, 3-chloro-5-OCF₃-phenyl, pyrazine carboxamide, piperidine-4-carboxylic acid) 2HCl |

TABLE 46

| Ex | Str |
|---|---|
| 43 | (structure with MeOCH₂CH₂N(nPr)-, thiazole, 3-chloro-5-OCF₃-phenyl, pyrazine carboxamide, piperidine-4-carboxylic acid) 2HCl |
| 44 | (structure with 2-methylpyrrolidine, thiazole, 4-fluoro-3-OCF₃-phenyl, pyrazine carboxamide, piperidine-4-carboxylic acid) 2HCl |
| 45 | (structure with 2-CF₃-pyrrolidine, thiazole, 3-methoxy-5-CF₃-phenyl, pyrazine carboxamide, piperidine-4-carboxylic acid) 2HCl |
| 46 | (structure with 3,3-dimethylpiperidine, thiazole, 3-methoxy-5-CF₃-phenyl, pyrazine carboxamide, piperidine-4-carboxylic acid) 2HCl |

TABLE 47
| Ex | Str |
|---|---|
| 47 | 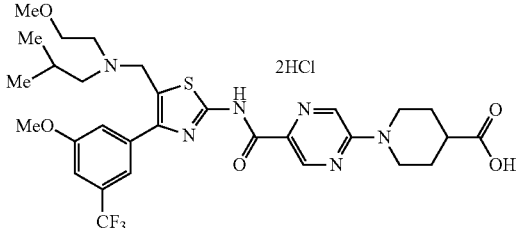 |
| 48 | 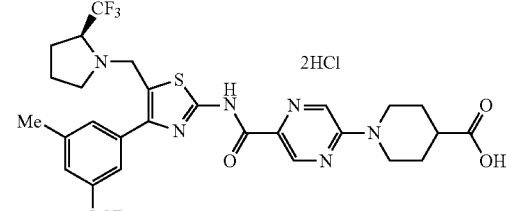 |
| 49 | 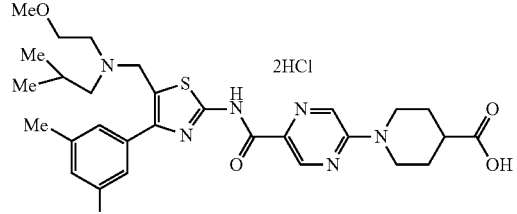 |
| 50 | 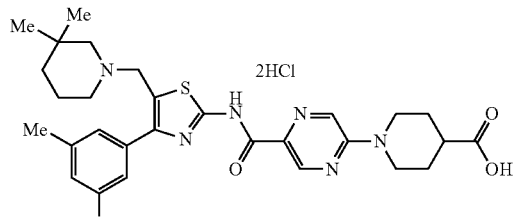 |
| 51 | 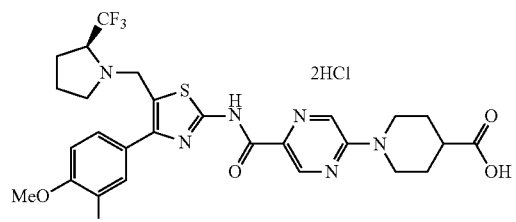 |
TABLE 48
| Ex | Str |
|---|---|
| 52 | 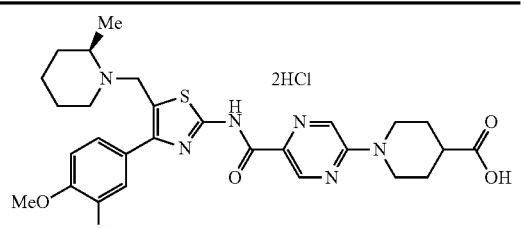 |
TABLE 48-continued
| Ex | Str |
|---|---|
| 53 | 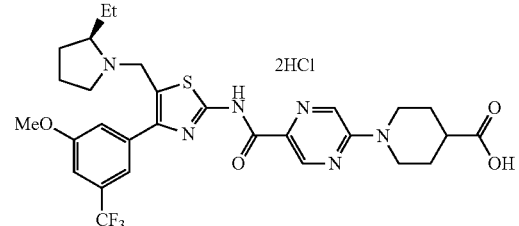 |
| 54 | 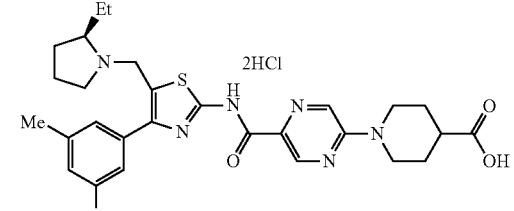 |
| 55 | 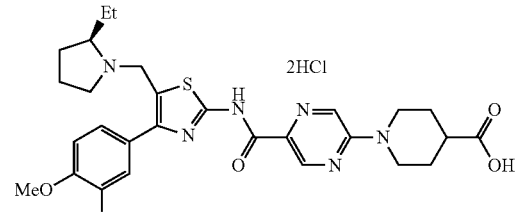 |
| 56 | 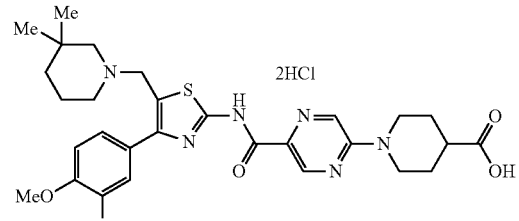 |
TABLE 49
| Ex | Str |
|---|---|
| 57 | 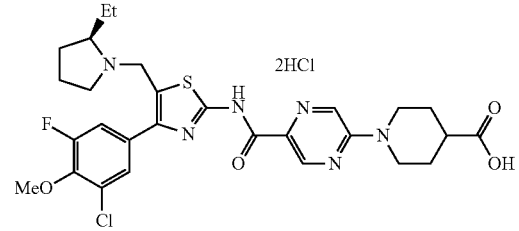 [SMILES: CC[C@@H]1CCCN1Cc1sc(NC(=O)c2cnc(N3CCC(C(=O)O)CC3)cn2)nc1-c1cc(F)c(OC)c(Cl)c1 ; "2HCl"] |
| 58 | 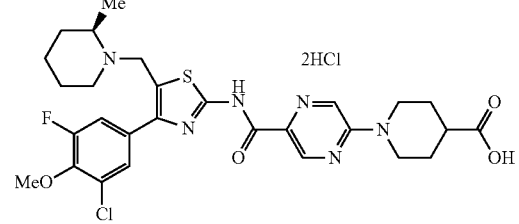 |

TABLE 49-continued
| Ex | Str |
|---|---|
| 59 | 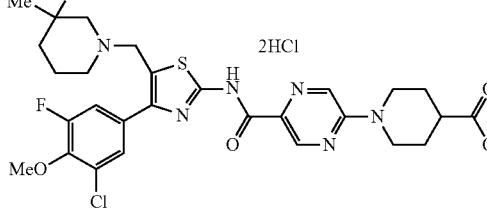 2HCl |
| 60 | 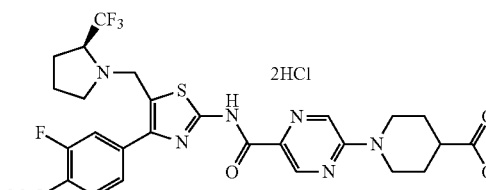 2HCl |
| 61 | 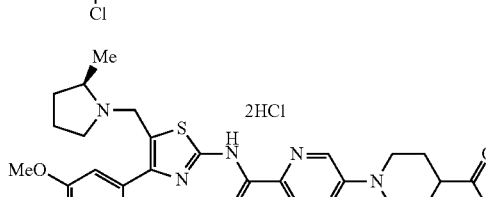 2HCl |
TABLE 50
| Ex | Str |
|---|---|
| 62 | 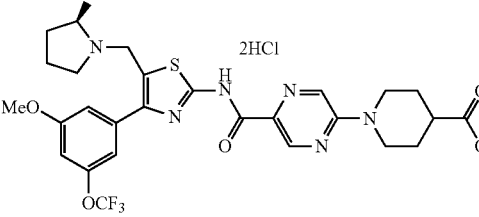 2HCl |
| 63 | 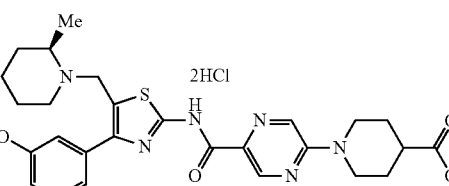 2HCl |
| 64 | 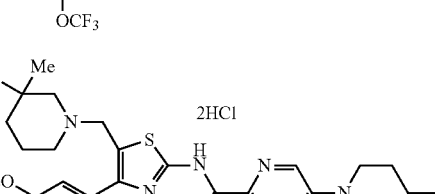 2HCl |
| 65 | 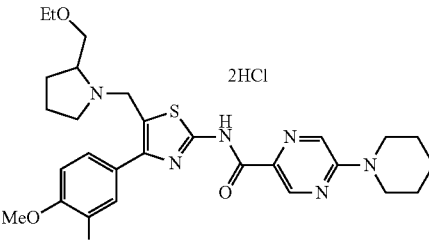 2HCl |
TABLE 51
| Ex | Str |
|---|---|
| 66 | 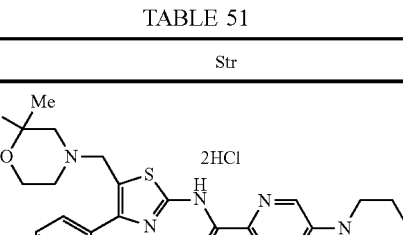 2HCl |
| 67 | 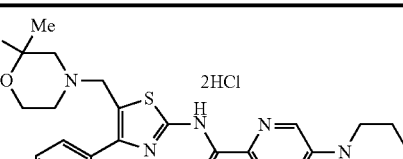 2HCl |
| 68 | 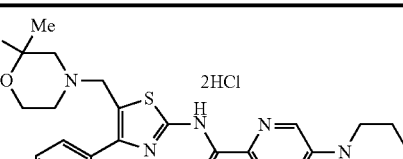 2HCl |

TABLE 51-continued
| Ex | Str |
|---|---|
| 69 | 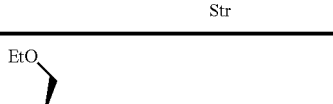 2HCl |
| 70 | 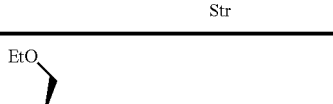 2HCl |
TABLE 52
| Ex | Str |
|---|---|
| 71 |  2HCl |
| 72 |  2HCl |
| 73 |  2HCl |

TABLE 52-continued
| Ex | Str |
|---|---|
| 74 | 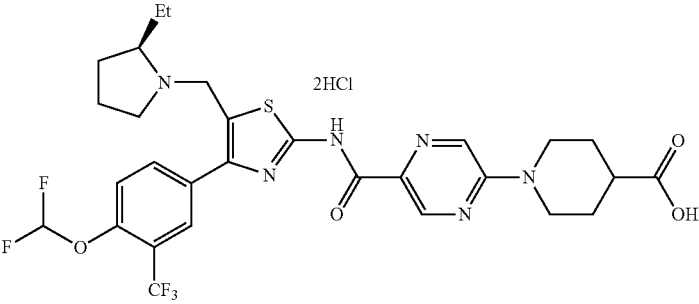 [SMILES: CC[C@@H]1CCCN1Cc1sc(NC(=O)c2cnc(N3CCC(C(=O)O)CC3)cn2)nc1-c1ccc(OC(F)F)c(C(F)(F)F)c1 ; "2HCl"] |
TABLE 53
| Ex | Str |
|---|---|
| 75 | 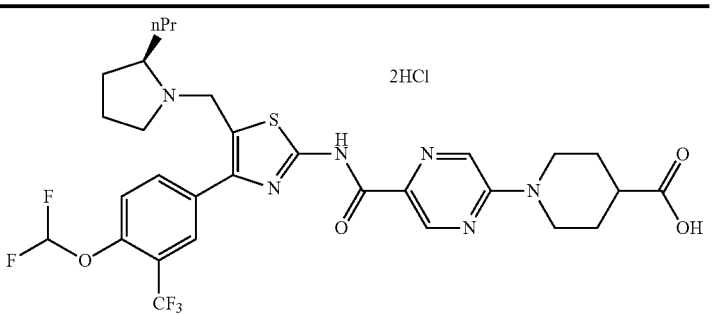 |
| 76 | 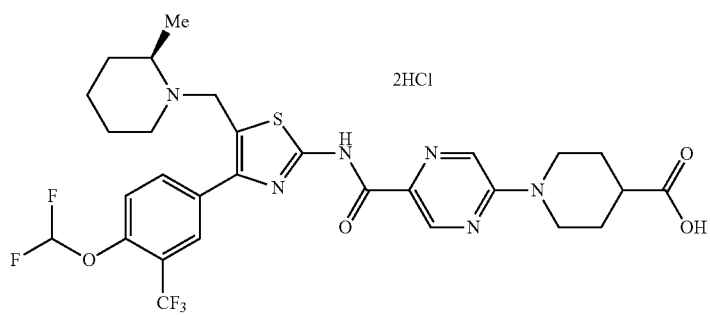 [SMILES: C[C@@H]1CCCCN1Cc1sc(NC(=O)c2cnc(N3CCC(C(=O)O)CC3)cn2)nc1-c1ccc(OC(F)F)c(C(F)(F)F)c1] |
| 77 | 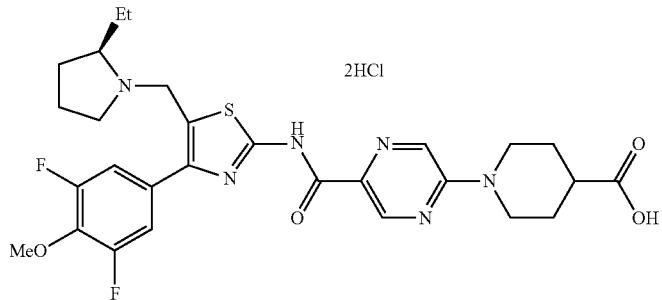 [SMILES: CC[C@@H]1CCCN1Cc1sc(NC(=O)c2cnc(N3CCC(C(=O)O)CC3)cn2)nc1-c1cc(F)c(OC)c(F)c1] |

TABLE 53-continued
| Ex | Str |
|---|---|
| 78 | 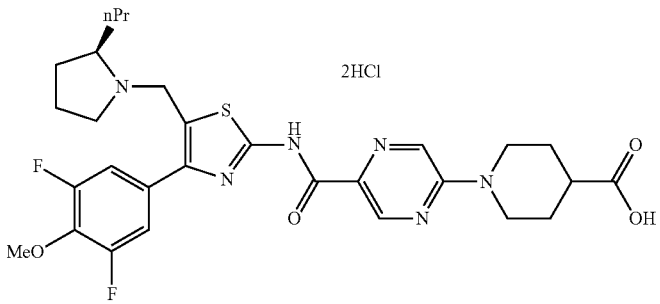 2HCl |
| 79 | 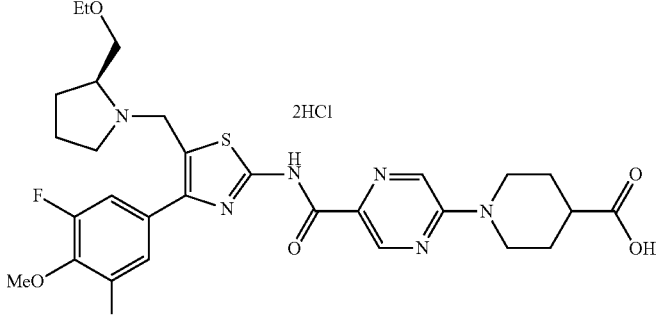 2HCl |
TABLE 54
| Ex | Str |
|---|---|
| 80 | 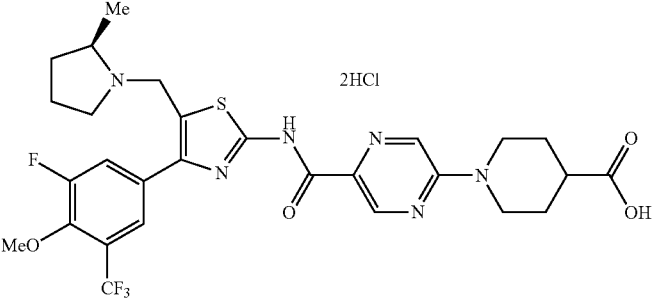 [SMILES: COc1c(F)cc(-c2nc(NC(=O)c3cnc(N4CCC(C(=O)O)CC4)cn3)sc2CN2CCC[C@H]2C)cc1C(F)(F)F] 2HCl |
| 81 | 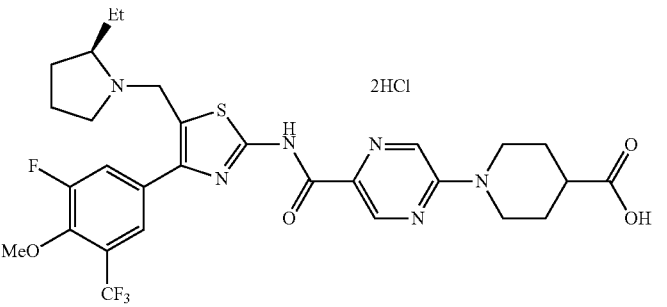 [SMILES: CC[C@@H]1CCCN1Cc1sc(NC(=O)c2cnc(N3CCC(C(=O)O)CC3)cn2)nc1-c1cc(F)c(OC)c(C(F)(F)F)c1] 2HCl |

TABLE 54-continued

| Ex | Str |
|---|---|
| 82 | (structure: (S)-2-nPr-pyrrolidine-CH2-thiazole[4-(3-F-4-MeO-5-CF3-phenyl)]-2-NHC(O)-pyrazine-5-(piperidine-4-COOH); 2HCl) |
| 83 | (structure: (S)-2-Me-piperidine-CH2-thiazole[4-(3-F-4-MeO-5-CF3-phenyl)]-2-NHC(O)-pyrazine-5-(piperidine-4-COOH); 2HCl) |

TABLE 55

| Ex | Str |
|---|---|
| 84 | (structure: (S)-2-(EtOCH2)-pyrrolidine-CH2-thiazole[4-(3-F-4-MeO-5-CF3-phenyl)]-2-NHC(O)-pyrazine-5-(piperidine-4-COOH); 2HCl) |
| 85 | (structure: (S)-2-(EtOCH2)-pyrrolidine-CH2-thiazole[4-(3-MeO-5-CF3-phenyl)]-2-NHC(O)-pyrazine-5-(piperidine-4-COOH); 2HCl) |

TABLE 55-continued
| Ex | Str |
|---|---|
| 86 | 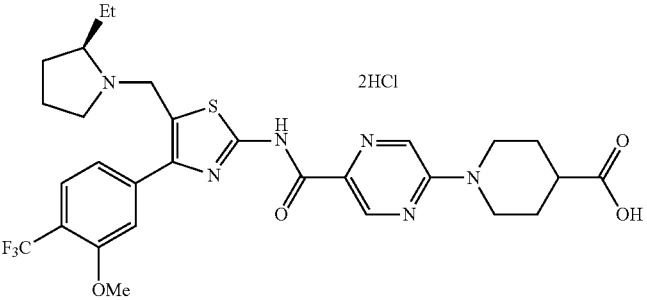 [SMILES: CC[C@@H]1CCCN1Cc1sc(NC(=O)c2cnc(N3CCC(C(=O)O)CC3)cn2)nc1-c1ccc(C(F)(F)F)c(OC)c1] 2HCl |
| 87 | 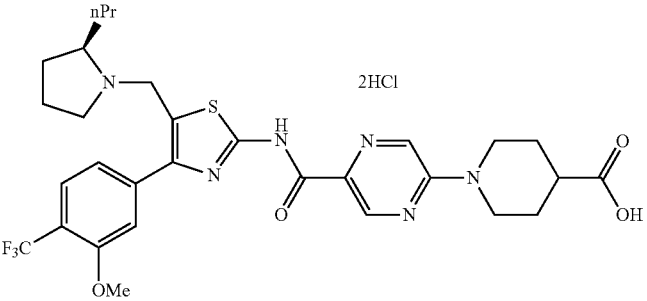 2HCl |
TABLE 56
| Ex | Str |
|---|---|
| 88 | 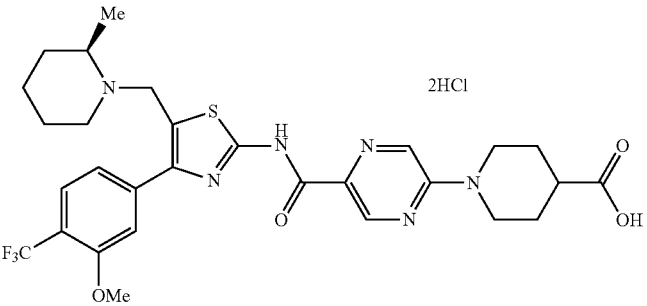 [SMILES: COc1cc(-c2nc(NC(=O)c3cnc(N4CCC(C(=O)O)CC4)cn3)sc2CN2CCCC[C@H]2C)ccc1C(F)(F)F] 2HCl |
| 89 | 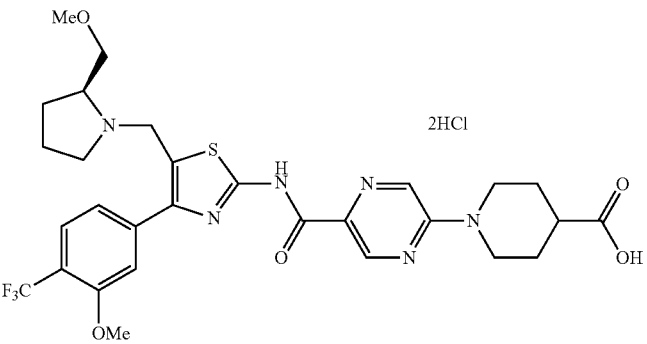 [SMILES: COC[C@@H]1CCCN1Cc1sc(NC(=O)c2cnc(N3CCC(C(=O)O)CC3)cn2)nc1-c1ccc(C(F)(F)F)c(OC)c1] 2HCl |

TABLE 56-continued
| Ex | Str |
|---|---|
| 90 | 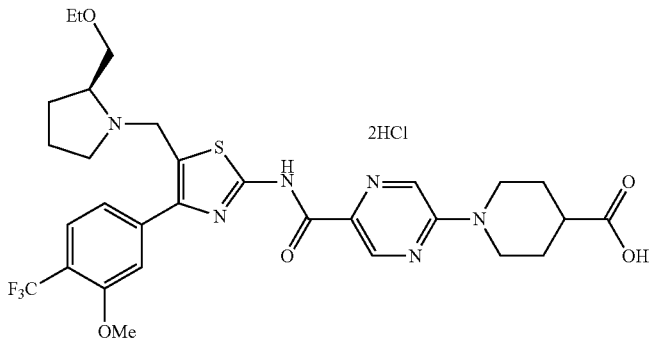 [SMILES: CCOC[C@@H]1CCCN1Cc1sc(NC(=O)c2cnc(N3CCC(C(=O)O)CC3)cn2)nc1-c1ccc(C(F)(F)F)c(OC)c1] |
| 91 | 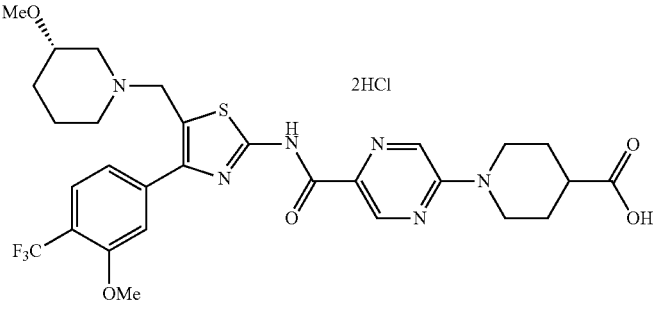 [SMILES: COc1cc(-c2nc(NC(=O)c3cnc(N4CCC(C(=O)O)CC4)cn3)sc2CN2CCC[C@H](OC)C2)ccc1C(F)(F)F] |
| 92 | 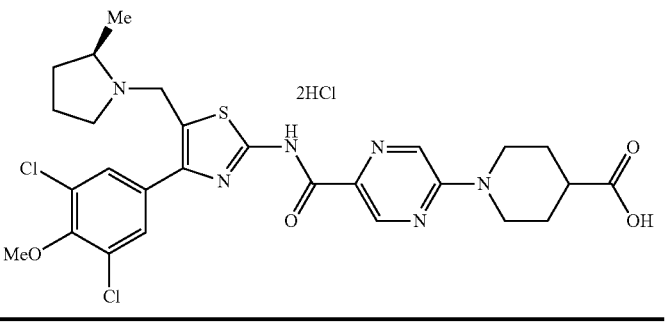 |
TABLE 57
| Ex | Str |
|---|---|
| 93 | 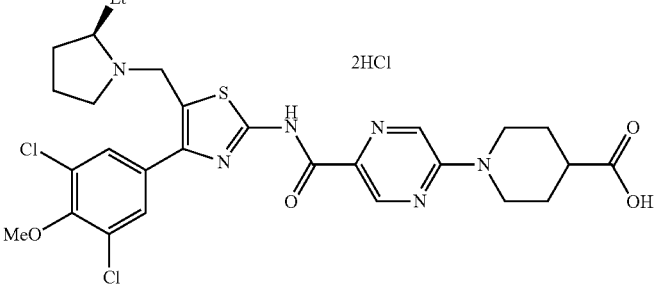 |

TABLE 57-continued
| Ex | Str |
|---|---|
| 94 | 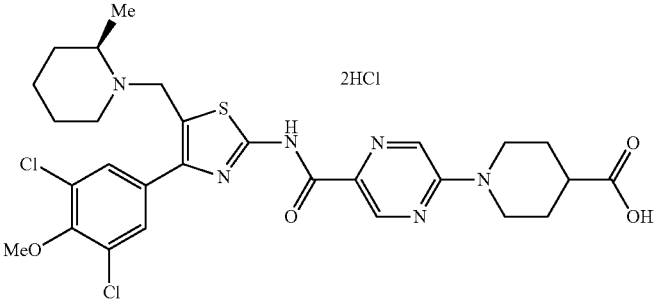 [SMILES: COc1c(Cl)cc(-c2nc(NC(=O)c3cnc(N4CCC(C(=O)O)CC4)cn3)sc2CN2CCCC[C@H]2C)cc1Cl] 2HCl |
| 95 | 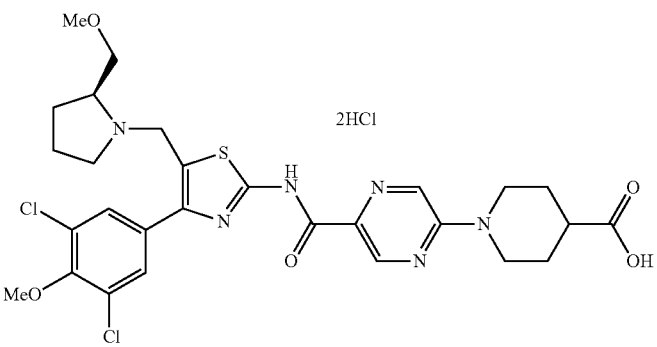 [SMILES: COC[C@@H]1CCCN1Cc1sc(NC(=O)c2cnc(N3CCC(C(=O)O)CC3)cn2)nc1-c1cc(Cl)c(OC)c(Cl)c1] 2HCl |
| 96 | 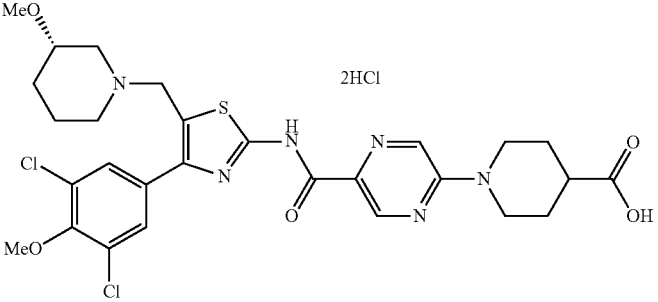 [SMILES: COc1c(Cl)cc(-c2nc(NC(=O)c3cnc(N4CCC(C(=O)O)CC4)cn3)sc2CN2CCC[C@H](OC)C2)cc1Cl] 2HCl |
| 97 | 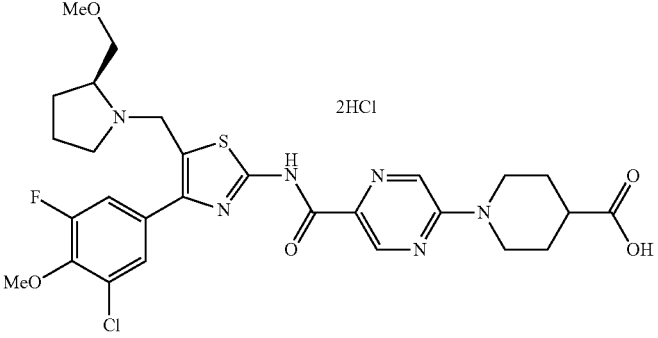 [SMILES: COC[C@@H]1CCCN1Cc1sc(NC(=O)c2cnc(N3CCC(C(=O)O)CC3)cn2)nc1-c1cc(F)c(OC)c(Cl)c1] 2HCl |

TABLE 58
| Ex | Str |
|---|---|
| 98 | 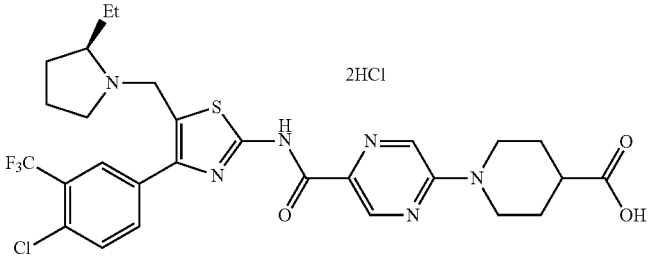 [SMILES: CC[C@@H]1CCCN1Cc1sc(NC(=O)c2cnc(N3CCC(C(=O)O)CC3)cn2)nc1-c1ccc(Cl)c(C(F)(F)F)c1] 2HCl |
| 99 | 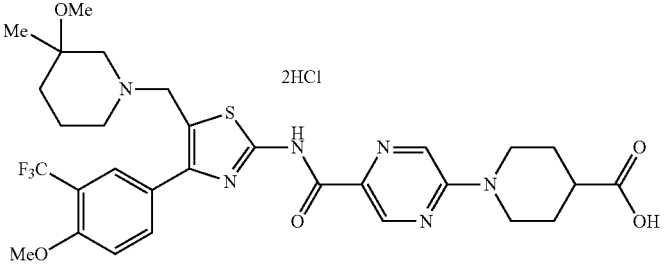 [SMILES: COc1ccc(-c2nc(NC(=O)c3cnc(N4CCC(C(=O)O)CC4)cn3)sc2CN2CCCC(C)(OC)C2)cc1C(F)(F)F] 2HCl |
| 100 | 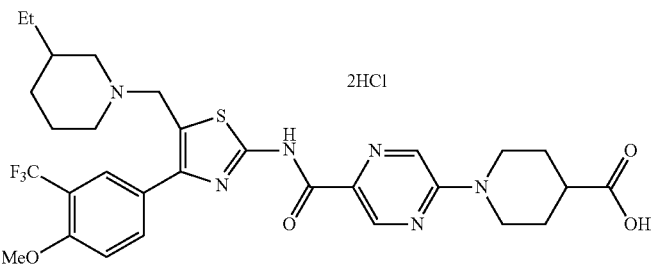 [SMILES: CCC1CCCN(Cc2sc(NC(=O)c3cnc(N4CCC(C(=O)O)CC4)cn3)nc2-c2ccc(OC)c(C(F)(F)F)c2)C1] 2HCl |
| 101 | 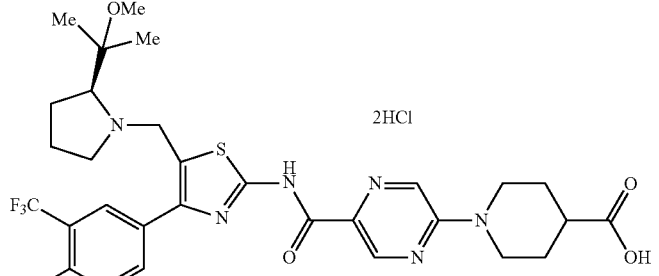 2HCl |
| 102 | 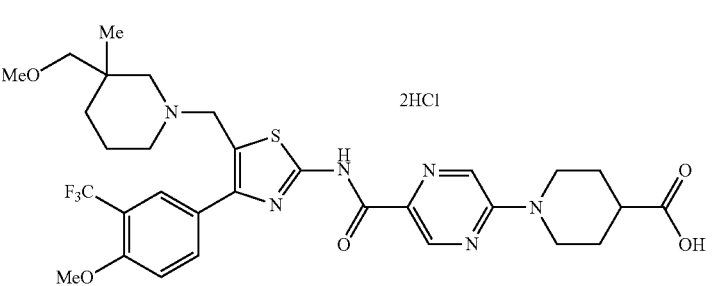 [SMILES: COCC1(C)CCCN(Cc2sc(NC(=O)c3cnc(N4CCC(C(=O)O)CC4)cn3)nc2-c2ccc(OC)c(C(F)(F)F)c2)C1] 2HCl |

TABLE 59
| Ex | Str |
|---|---|
| 103 | 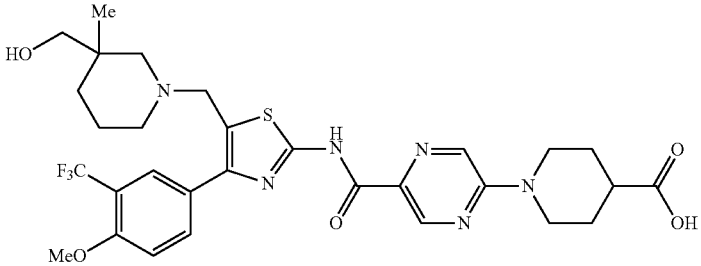 [SMILES: COc1ccc(-c2nc(NC(=O)c3cnc(N4CCC(C(=O)O)CC4)cn3)sc2CN2CCCC(C)(CO)C2)cc1C(F)(F)F] |
| 104 | 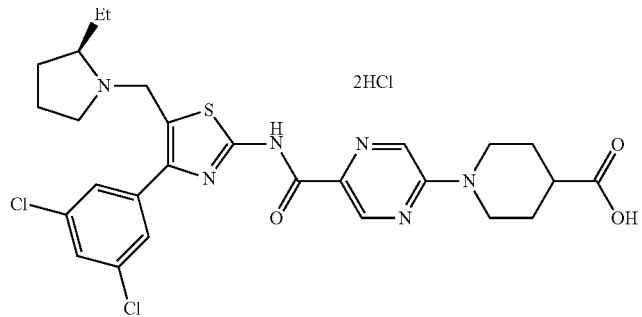 [SMILES: CC[C@@H]1CCCN1Cc1sc(NC(=O)c2cnc(N3CCC(C(=O)O)CC3)cn2)nc1-c1cc(Cl)cc(Cl)c1] |
| 105 | 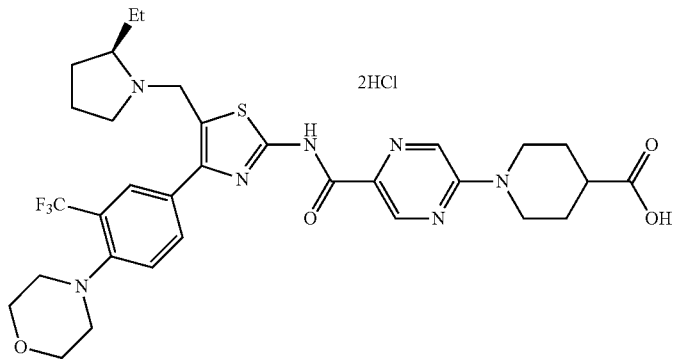 [SMILES: CC[C@@H]1CCCN1Cc1sc(NC(=O)c2cnc(N3CCC(C(=O)O)CC3)cn2)nc1-c1ccc(N2CCOCC2)c(C(F)(F)F)c1] |
| 106 | 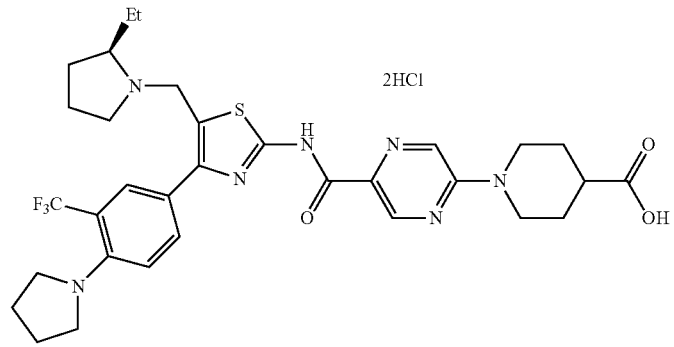 [SMILES: CC[C@@H]1CCCN1Cc1sc(NC(=O)c2cnc(N3CCC(C(=O)O)CC3)cn2)nc1-c1ccc(N2CCCC2)c(C(F)(F)F)c1] |

TABLE 59-continued
| Ex | Str |
|---|---|
| 107 | 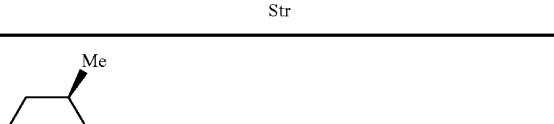 |
TABLE 60
| Ex | Str |
|---|---|
| 108 | |
| 109 | |
| 110 | |

TABLE 60-continued
| Ex | Str |
|---|---|
| 111 | 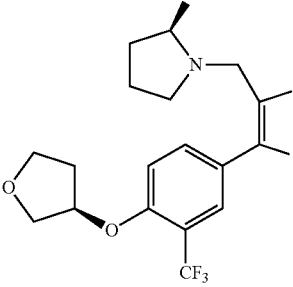 |
| 112 | 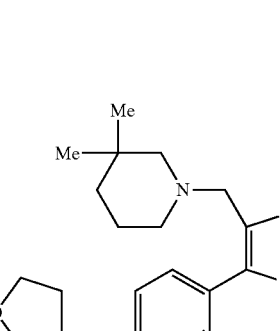 |
TABLE 61
| Ex | Str |
|---|---|
| 113 | 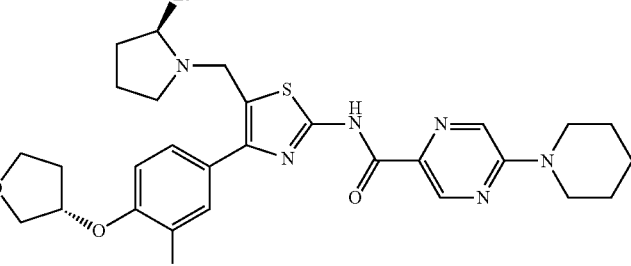 |
| 114 | 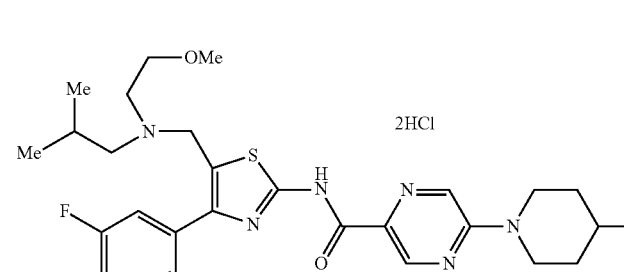 |

TABLE 61-continued
| Ex | Str |
|---|---|
| 115 | 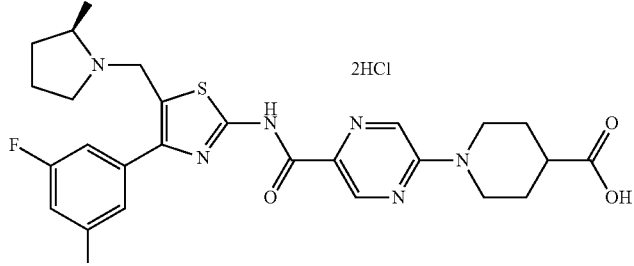 2HCl |
| 116 | 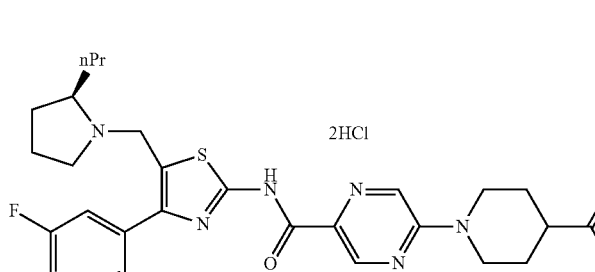 2HCl |
TABLE 62
| Ex | Str |
|---|---|
| 117 | 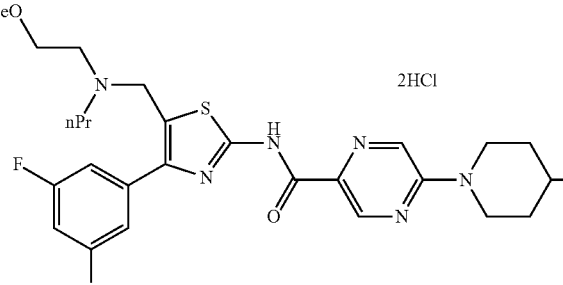 2HCl |
| 118 | 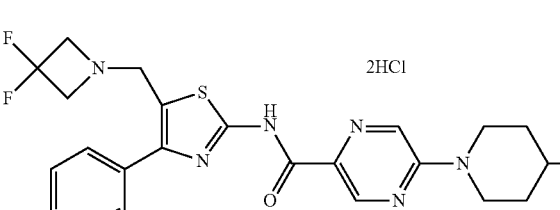 2HCl |

TABLE 62-continued
| Ex | Str |
|---|---|
| 119 | 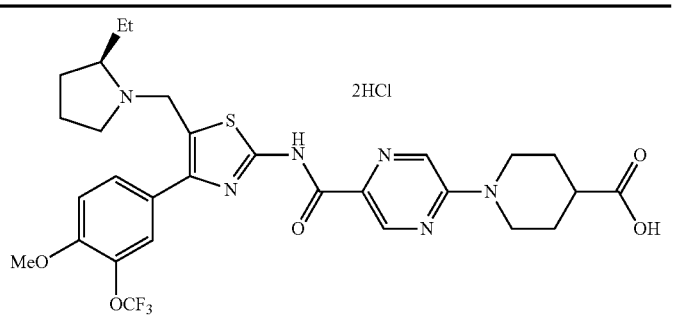 2HCl |
| 120 | 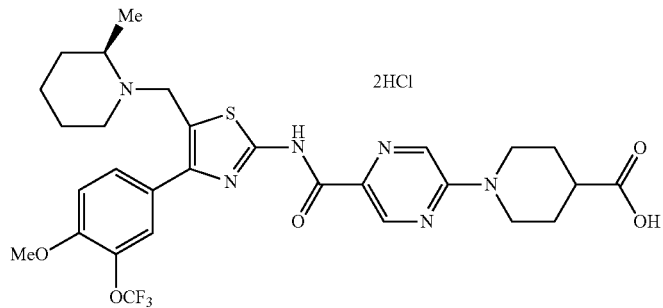 [SMILES: COc1ccc(-c2nc(NC(=O)c3cnc(N4CCC(C(=O)O)CC4)cn3)sc2CN2CCCC[C@H]2C)cc1OC(F)(F)F] 2HCl |
| 121 | 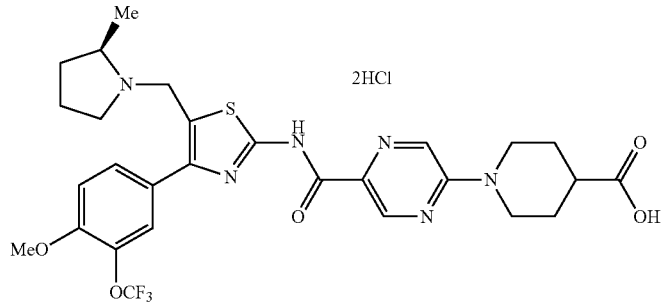 [SMILES: COc1ccc(-c2nc(NC(=O)c3cnc(N4CCC(C(=O)O)CC4)cn3)sc2CN2CCC[C@H]2C)cc1OC(F)(F)F] 2HCl |
TABLE 63
| Ex | Str |
|---|---|
| 122 | 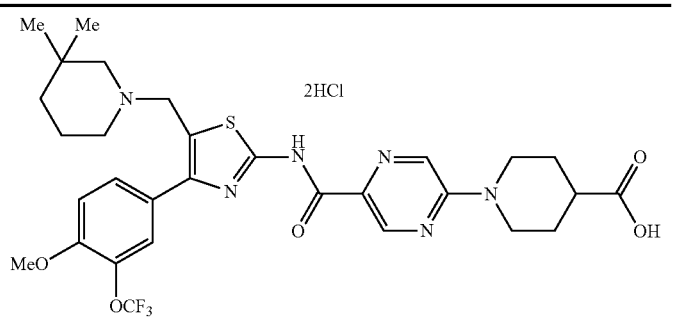 2HCl |

TABLE 63-continued
| Ex | Str |
|---|---|
| 123 | 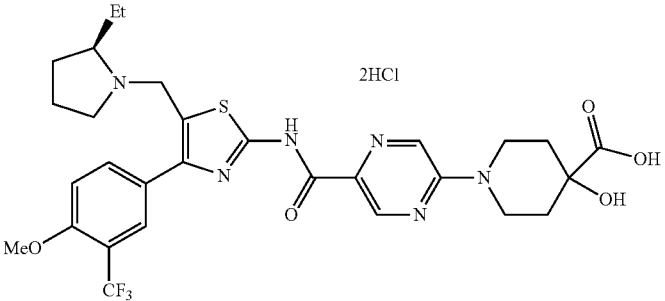 [SMILES: CC[C@@H]1CCCN1Cc1sc(NC(=O)c2cnc(N3CCC(O)(C(=O)O)CC3)cn2)nc1-c1ccc(OC)c(C(F)(F)F)c1] 2HCl |
| 124 | 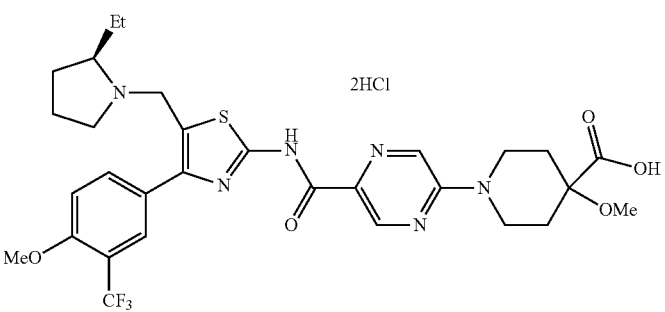 [SMILES: CC[C@@H]1CCCN1Cc1sc(NC(=O)c2cnc(N3CCC(OC)(C(=O)O)CC3)cn2)nc1-c1ccc(OC)c(C(F)(F)F)c1] 2HCl |
| 125 | 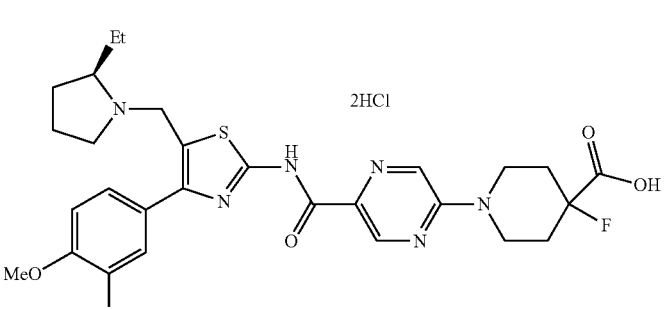 2HCl |
TABLE 64
| Ex | Str |
|---|---|
| 126 | 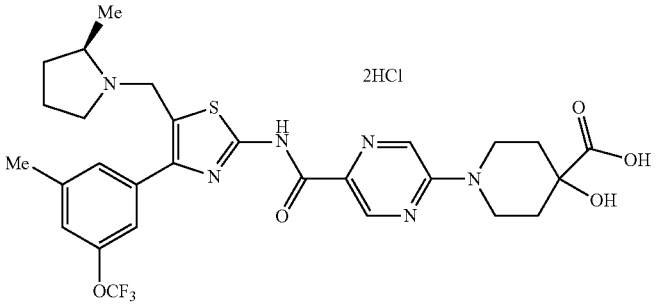 [SMILES: Cc1cc(OC(F)(F)F)cc(-c2nc(NC(=O)c3cnc(N4CCC(O)(C(=O)O)CC4)cn3)sc2CN2CCC[C@H]2C)c1] 2HCl |

TABLE 64-continued
| Ex | Str |
|---|---|
| 127 | 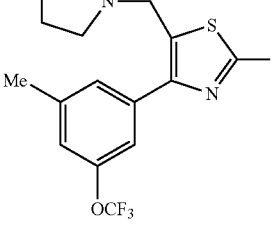 |
| 128 | 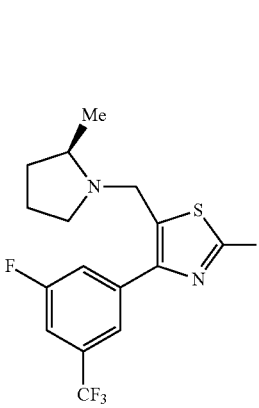 |
| 129 | 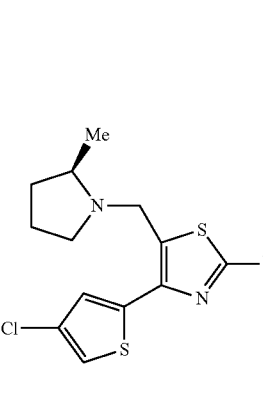 |
| 130 | 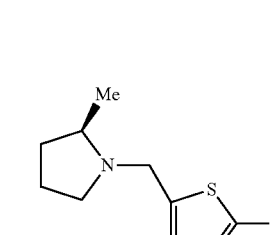 |

TABLE 65

| Ex | Str |
|---|---|
| 131 | (structure: 4-[(2S)-2-methylpyrrolidin-1-ylmethyl]-4-(3-methoxy-5-(trifluoromethyl)phenyl)thiazol-2-yl]amide of 5-(4-fluoro-4-carboxypiperidin-1-yl)pyrazine-2-carboxylic acid, 2HCl) |
| 132 | (structure: 4-[(2S)-2-methylpyrrolidin-1-ylmethyl]-4-(3-methoxy-5-(trifluoromethyl)phenyl)thiazol-2-yl]amide of 5-(4-methoxy-4-carboxypiperidin-1-yl)pyrazine-2-carboxylic acid, 2HCl) |
| 133 | (structure: 4-[(2S)-2-methylpyrrolidin-1-ylmethyl]-4-(4-fluoro-3-(trifluoromethyl)phenyl)thiazol-2-yl]amide of 5-(4-fluoro-4-carboxypiperidin-1-yl)pyrazine-2-carboxylic acid, 2HCl) |
| 134 | (structure: 4-[(2S)-2-methylpyrrolidin-1-ylmethyl]-4-(4-fluoro-3-(trifluoromethyl)phenyl)thiazol-2-yl]amide of 5-(4-hydroxy-4-carboxypiperidin-1-yl)pyrazine-2-carboxylic acid, 2HCl) |

TABLE 66

| Ex | Str |
|---|---|
| 135 | (structure: 2HCl salt; (2S)-2-methylpyrrolidin-1-ylmethyl-thiazole bearing 4-fluoro-3-(trifluoromethyl)phenyl, linked via amide to pyrazine-piperidine with 4-methoxy-4-carboxylic acid) |
| 136 | (structure: 2HCl salt; (2S)-2-methylpyrrolidin-1-ylmethyl-thiazole bearing 3-chloro-5-(trifluoromethyl)phenyl, linked via amide to pyrazine-piperidine-4-carboxylic acid) |
| 137 | (structure: 2HCl salt; 3,3-dimethylpiperidin-1-ylmethyl-thiazole bearing 4-chlorothiophen-2-yl, linked via amide to pyrazine-piperidine-4-carboxylic acid) |
| 138 | (structure: 2HCl salt; (2-methylpyrrolidin-1-yl)methyl-thiazole bearing 4-chlorothiophen-2-yl, linked via amide to pyrazine-piperidine-4-carboxylic acid) |
| 139 | (structure: 2HCl salt; 3-(trifluoromethyl)piperidin-1-ylmethyl-thiazole bearing 4-chlorothiophen-2-yl, linked via amide to pyrazine-piperidine-4-carboxylic acid) |

TABLE 67
| Ex | Str |
|---|---|
| 140 | 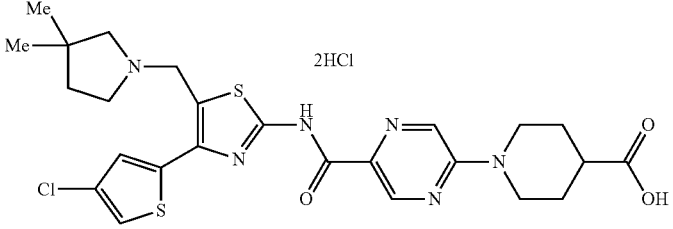 [SMILES: CC1(C)CCN(Cc2sc(NC(=O)c3cnc(N4CCC(C(=O)O)CC4)cn3)nc2-c2cc(Cl)cs2)C1] 2HCl |
| 141 | 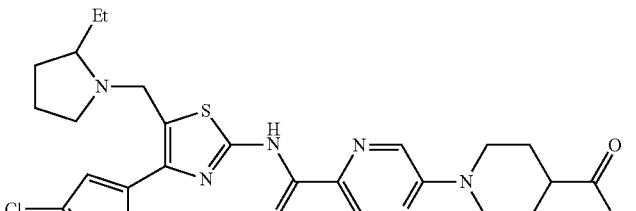 |
| 142 | 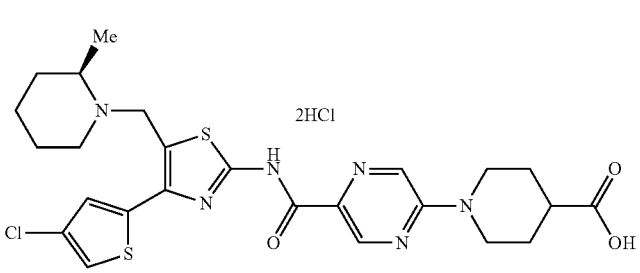 [SMILES: C[C@@H]1CCCCN1Cc1sc(NC(=O)c2cnc(N3CCC(C(=O)O)CC3)cn2)nc1-c1cc(Cl)cs1] 2HCl |
| 143 | 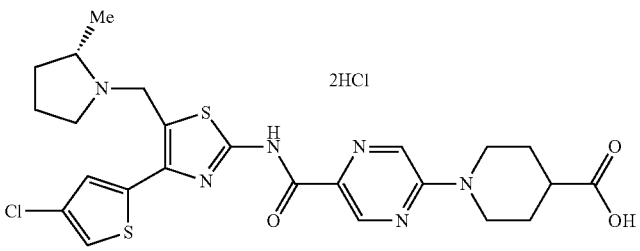 [SMILES: C[C@H]1CCCN1Cc1sc(NC(=O)c2cnc(N3CCC(C(=O)O)CC3)cn2)nc1-c1cc(Cl)cs1] 2HCl |
| 144 | 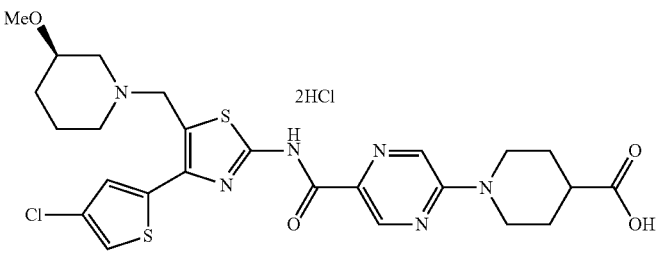 [SMILES: CO[C@@H]1CCCN(Cc2sc(NC(=O)c3cnc(N4CCC(C(=O)O)CC4)cn3)nc2-c2cc(Cl)cs2)C1] 2HCl |
| 145 | 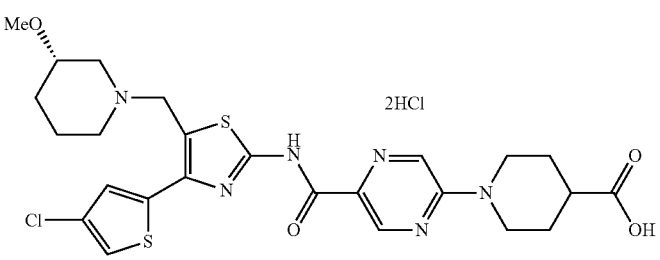 [SMILES: CO[C@H]1CCCN(Cc2sc(NC(=O)c3cnc(N4CCC(C(=O)O)CC4)cn3)nc2-c2cc(Cl)cs2)C1] 2HCl |

TABLE 68
| Ex | Str |
|---|---|
| 146 | 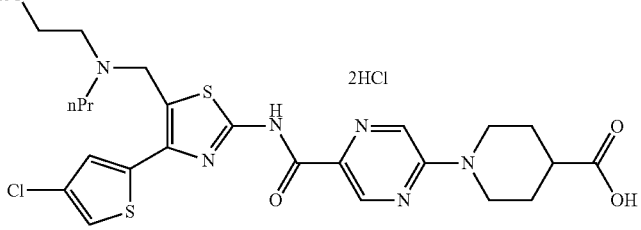 |
| 147 | 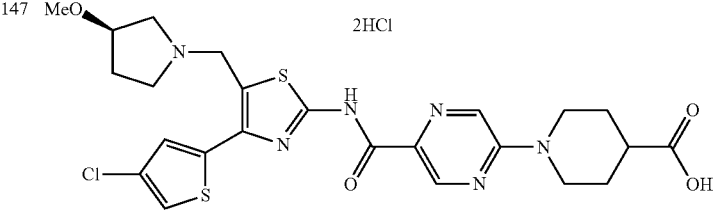 |
| 148 | 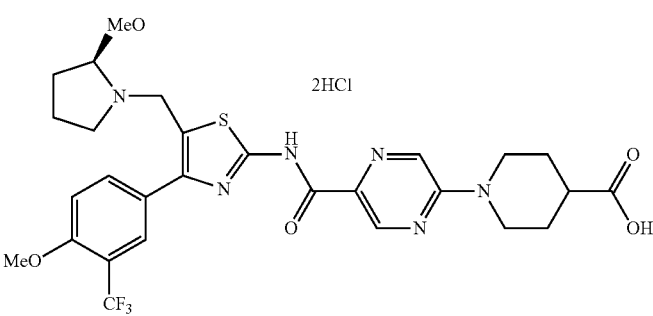 [SMILES: COc1ccc(-c2nc(NC(=O)c3cnc(N4CCC(C(=O)O)CC4)cn3)sc2CN2CCC[C@H]2OC)cc1C(F)(F)F] |
| 149 | 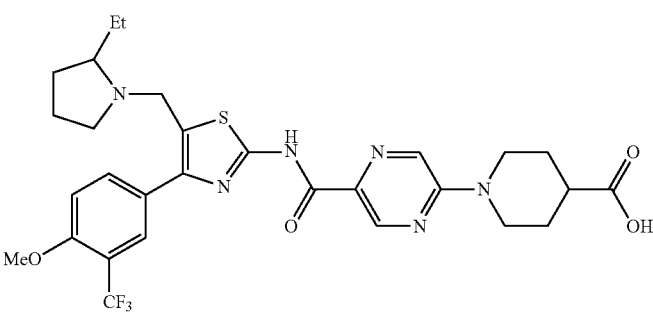 [SMILES: CCC1CCCN1Cc1sc(NC(=O)c2cnc(N3CCC(C(=O)O)CC3)cn2)nc1-c1ccc(OC)c(C(F)(F)F)c1] |
| 150 | 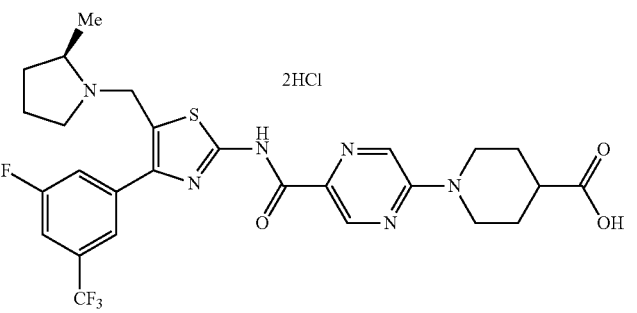 [SMILES: C[C@@H]1CCCN1Cc1sc(NC(=O)c2cnc(N3CCC(C(=O)O)CC3)cn2)nc1-c1cc(F)cc(C(F)(F)F)c1] |

TABLE 69
| Ex | Str |
|---|---|
| 151 | 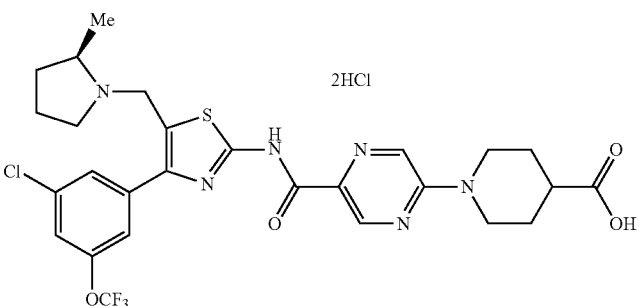 2HCl |
| 152 | 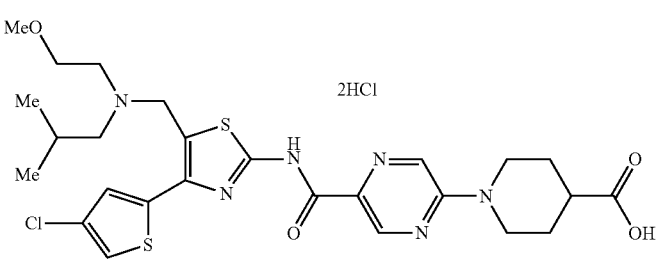 [SMILES: COCCN(Cc1sc(NC(=O)c2cnc(N3CCC(C(=O)O)CC3)cn2)nc1-c1cc(Cl)cs1)CC(C)C] 2HCl |
| 153 | 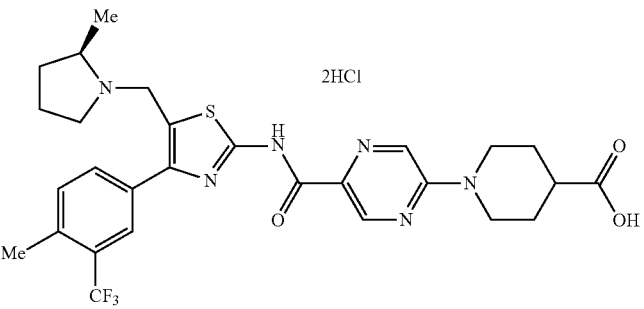 [SMILES: Cc1ccc(-c2nc(NC(=O)c3cnc(N4CCC(C(=O)O)CC4)cn3)sc2CN2CCC[C@H]2C)cc1C(F)(F)F] 2HCl |
| 154 | 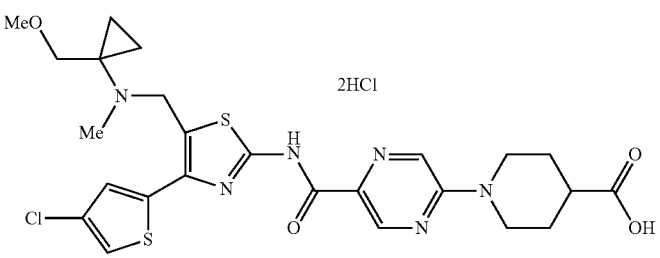 [SMILES: COCC1(N(C)Cc2sc(NC(=O)c3cnc(N4CCC(C(=O)O)CC4)cn3)nc2-c2cc(Cl)cs2)CC1] 2HCl |
| 155 | 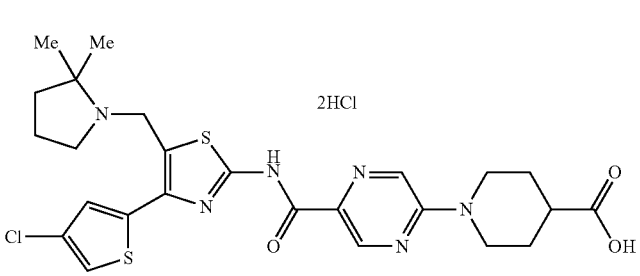 [SMILES: CC1(C)CCCN1Cc1sc(NC(=O)c2cnc(N3CCC(C(=O)O)CC3)cn2)nc1-c1cc(Cl)cs1] 2HCl |

TABLE 70
| Ex | Str |
|---|---|
| 156 | 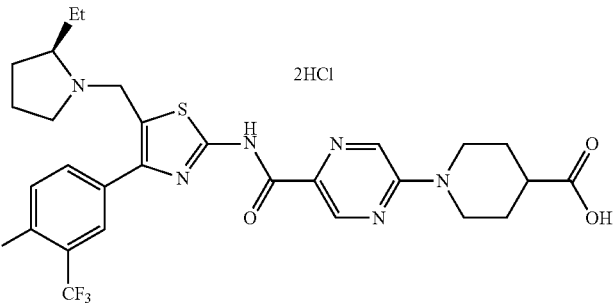 |
| 157 | 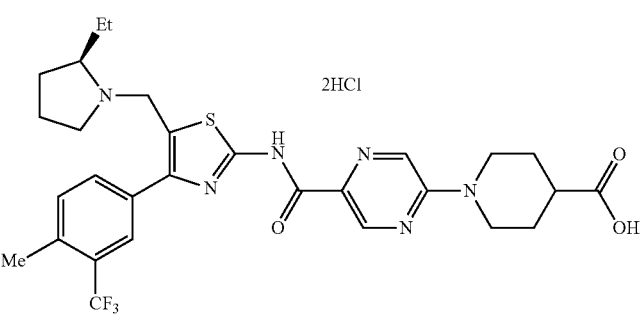 |
| 158 | 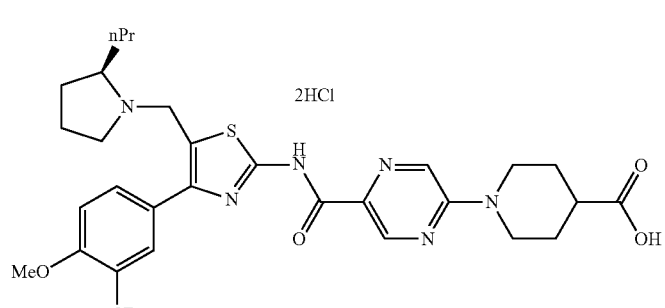 |
| 159 | 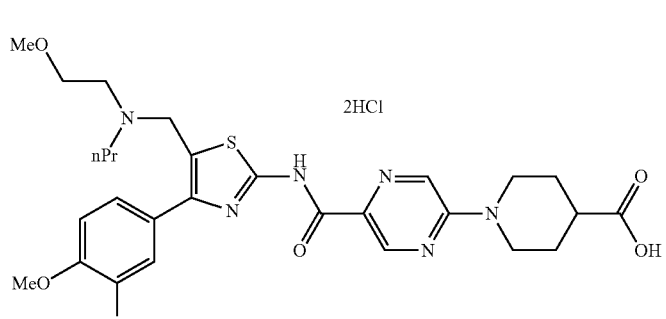 |

TABLE 71

| Ex | Str |
|---|---|
| 160 | (2S)-2-methylpyrrolidin-1-ylmethyl-[4-(3-methoxy-5-trifluoromethylphenyl)thiazol-2-yl]-NH-C(O)-pyrazine-piperidine-4-carboxylic acid · 2HCl |
| 161 | (2S)-2-nPr-pyrrolidin-1-ylmethyl-[4-(3-methoxy-5-trifluoromethylphenyl)thiazol-2-yl]-NH-C(O)-pyrazine-piperidine-4-carboxylic acid · 2HCl |
| 162 | (2S)-2-methylpyrrolidin-1-ylmethyl-[4-(3-methoxy-5-trifluoromethoxyphenyl)thiazol-2-yl]-NH-C(O)-pyrazine-piperidine-4-carboxylic acid · 2HCl |
| 163 | (2S)-2-methylpiperidin-1-ylmethyl-[4-(4-methoxy-3-trifluoromethylphenyl)thiazol-2-yl]-NH-C(O)-pyrazine-piperidine-4-carboxylic acid · 2HCl |

TABLE 72
| Ex | Str |
|---|---|
| 164 | 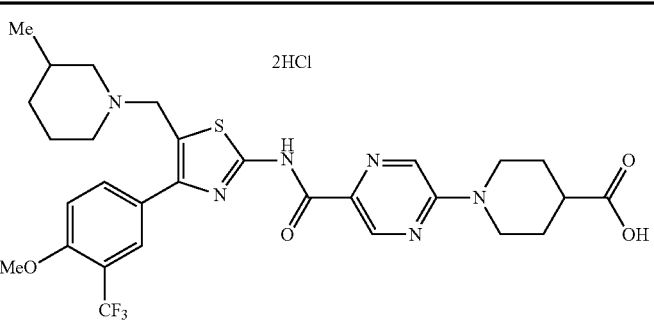 2HCl |
| 165 | 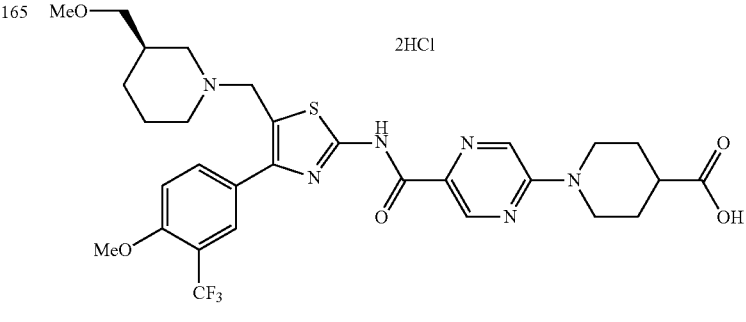 2HCl |
| 166 | 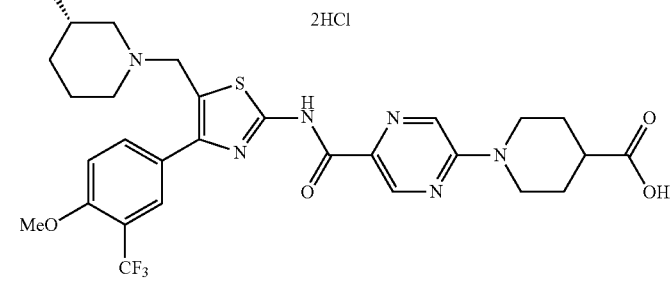 2HCl |
| 167 | 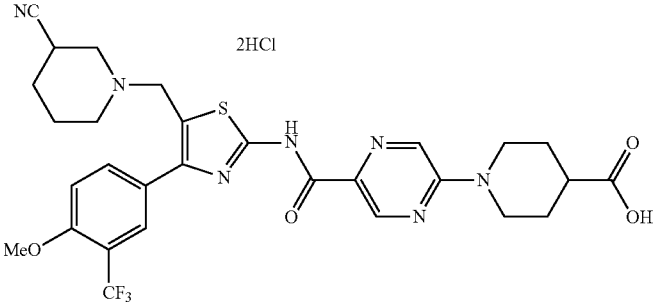 [SMILES: COc1ccc(-c2nc(NC(=O)c3cnc(N4CCC(C(=O)O)CC4)cn3)sc2CN2CCCC(C#N)C2)cc1C(F)(F)F] 2HCl |
| 168 | 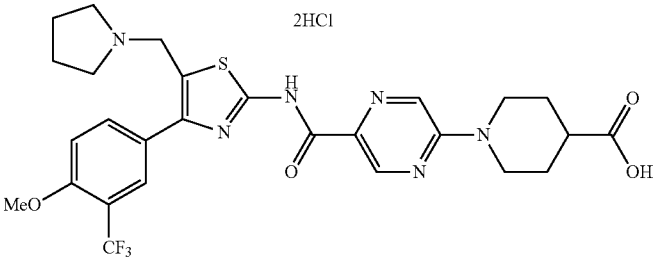 [SMILES: COc1ccc(-c2nc(NC(=O)c3cnc(N4CCC(C(=O)O)CC4)cn3)sc2CN2CCCC2)cc1C(F)(F)F] 2HCl |

TABLE 73
| Ex | Str |
|---|---|
| 169 | 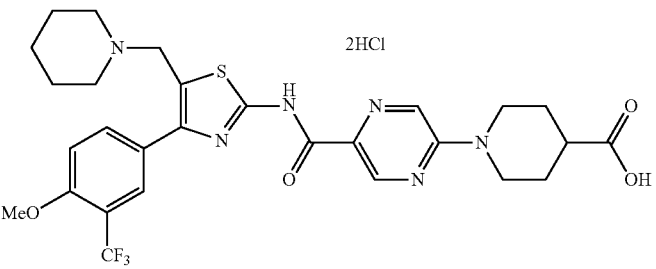 [SMILES: COc1ccc(-c2nc(NC(=O)c3cnc(N4CCC(C(=O)O)CC4)cn3)sc2CN2CCCCC2)cc1C(F)(F)F] 2HCl |
| 170 | 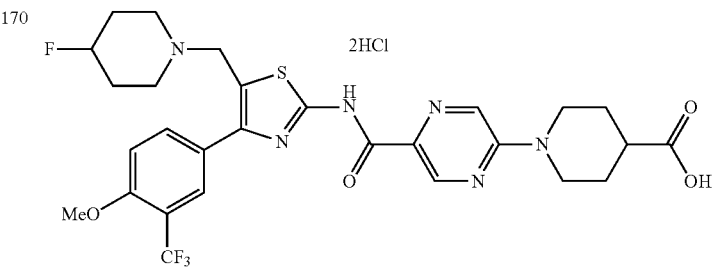 2HCl |
| 171 | 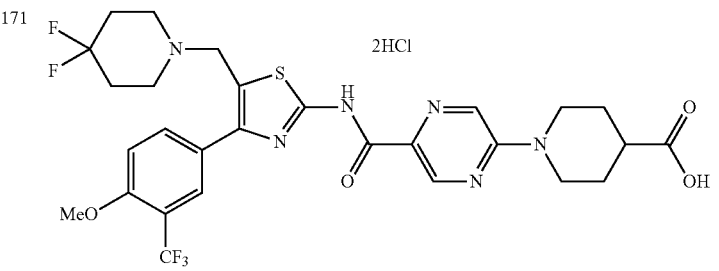 2HCl |
| 172 | 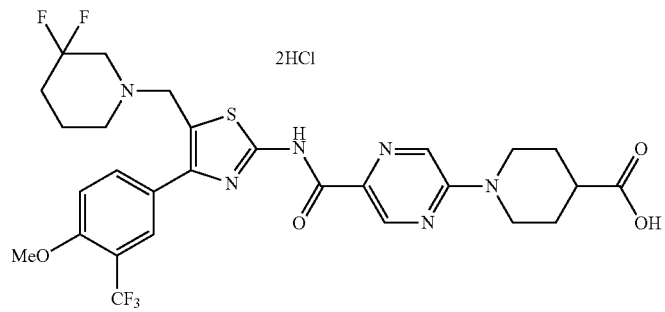 [SMILES: COc1ccc(-c2nc(NC(=O)c3cnc(N4CCC(C(=O)O)CC4)cn3)sc2CN2CCCC(F)(F)C2)cc1C(F)(F)F] 2HCl |
| 173 | 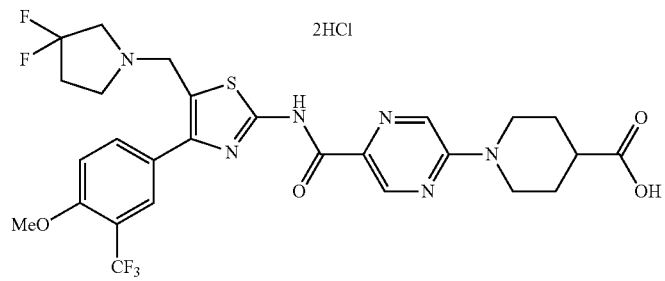 [SMILES: COc1ccc(-c2nc(NC(=O)c3cnc(N4CCC(C(=O)O)CC4)cn3)sc2CN2CCC(F)(F)C2)cc1C(F)(F)F] 2HCl |

TABLE 74

| Ex | Str |
|---|---|
| 174 | (structure: (3S)-3-fluoropyrrolidin-1-ylmethyl-thiazole with 4-(4-methoxy-3-trifluoromethylphenyl) substituent, linked via NH-C(O) to pyrazine-piperidine-4-carboxylic acid; 2HCl) |
| 175 | (structure: (3R)-3-fluoropyrrolidin-1-ylmethyl-thiazole with 4-(4-methoxy-3-trifluoromethylphenyl) substituent, linked via NH-C(O) to pyrazine-piperidine-4-carboxylic acid; 2HCl) |
| 176 | (structure: (3S)-3-methylpyrrolidin-1-ylmethyl-thiazole with 4-(4-methoxy-3-trifluoromethylphenyl) substituent, linked via NH-C(O) to pyrazine-piperidine-4-carboxylic acid; 2HCl) |
| 177 | (structure: (3R)-3-methylpyrrolidin-1-ylmethyl-thiazole with 4-(4-methoxy-3-trifluoromethylphenyl) substituent, linked via NH-C(O) to pyrazine-piperidine-4-carboxylic acid; 2HCl) |
| 178 | (structure: 4-methoxypiperidin-1-ylmethyl-thiazole with 4-(4-methoxy-3-trifluoromethylphenyl) substituent, linked via NH-C(O) to pyrazine-piperidine-4-carboxylic acid; 2HCl) |

TABLE 75
| Ex | Str |
|---|---|
| 179 | 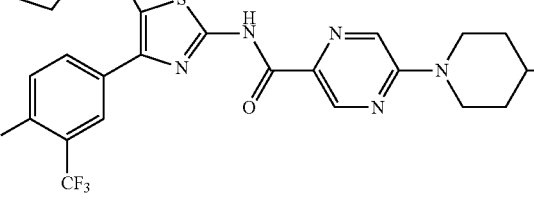 |
| 180 | 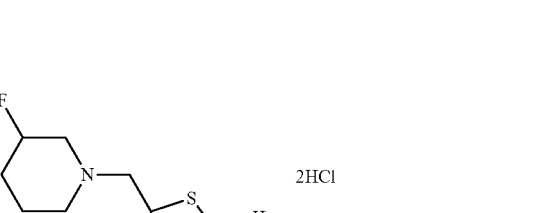 |
| 181 | 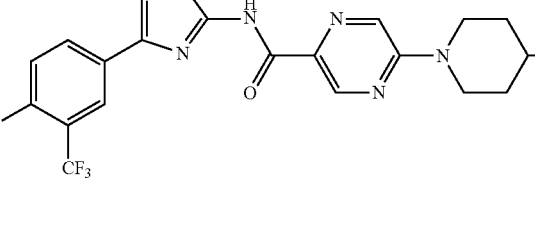 |
| 182 | 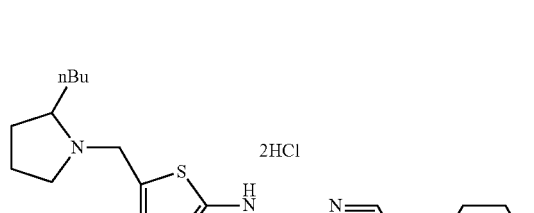 |

TABLE 76
| Ex | Str |
|---|---|
| 183 | 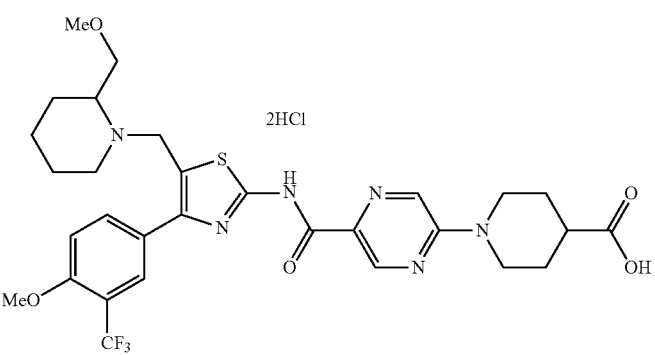 [SMILES: COCC1CCCCN1Cc1sc(NC(=O)c2cnc(N3CCC(C(=O)O)CC3)cn2)nc1-c1ccc(OC)c(C(F)(F)F)c1] |
| 184 | 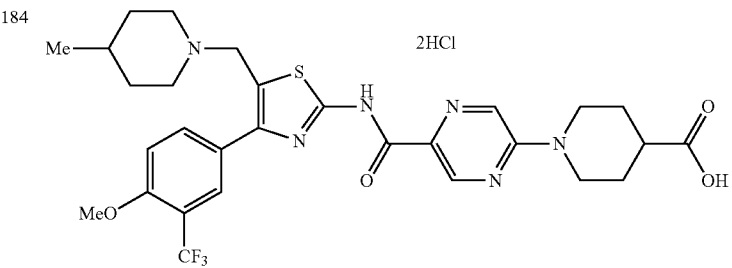 |
| 185 | 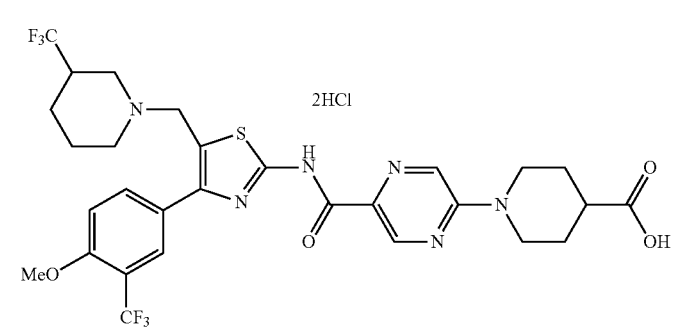 [SMILES: COc1ccc(-c2nc(NC(=O)c3cnc(N4CCC(C(=O)O)CC4)cn3)sc2CN2CCCC(C(F)(F)F)C2)cc1C(F)(F)F] |
| 186 | 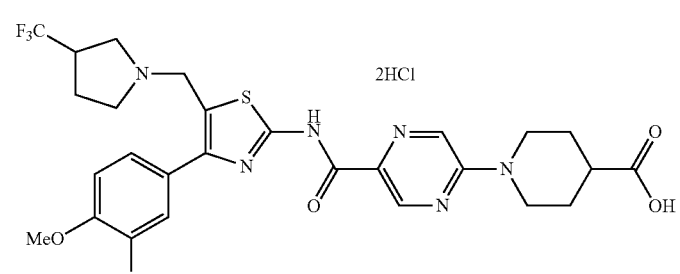 |

TABLE 77
| Ex | Str |
|---|---|
| 187 | 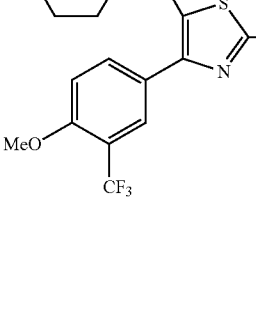 |
| 188 | 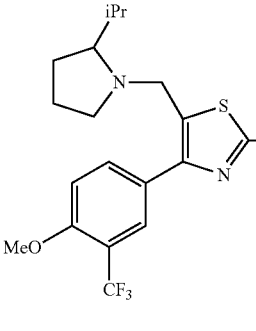 |
| 189 | 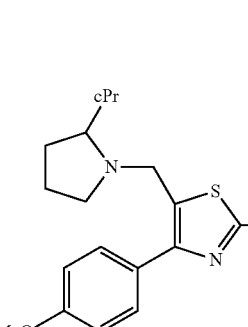 |
| 190 | 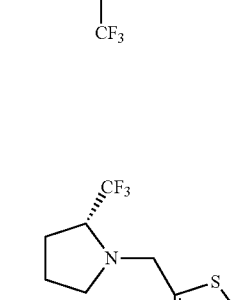 |

TABLE 78
| Ex | Str |
|---|---|
| 191 | 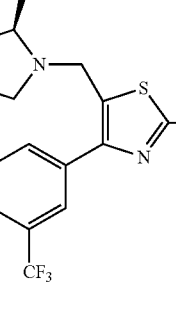 2HCl |
| 192 | 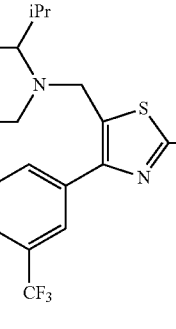 2HCl |
| 193 | 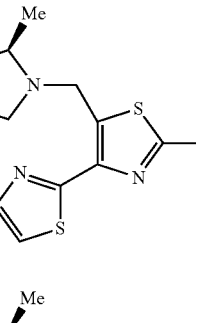 HCl |
| 194 | 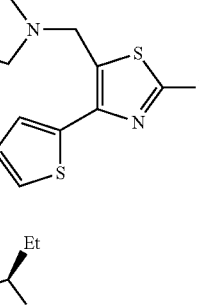 2HCl |
| 195 | 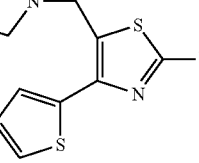 2HCl |

TABLE 79
| Ex | Str |
|---|---|
| 196 | 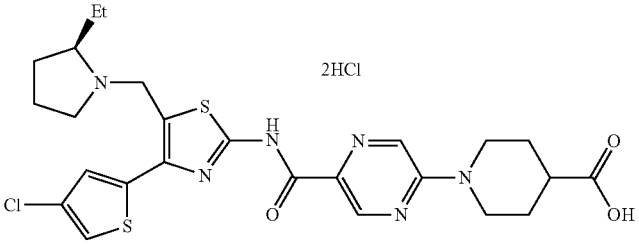 [SMILES: CC[C@@H]1CCCN1Cc1sc(NC(=O)c2cnc(N3CCC(C(=O)O)CC3)cn2)nc1-c1cc(Cl)cs1 ; "2HCl"] 2HCl |
| 197 | 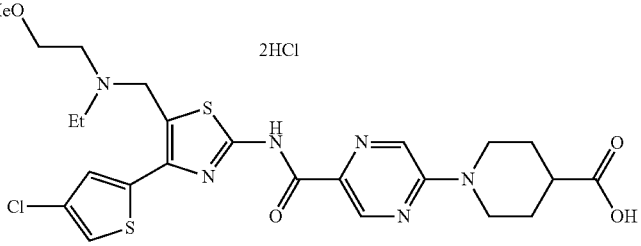 2HCl |
| 198 | 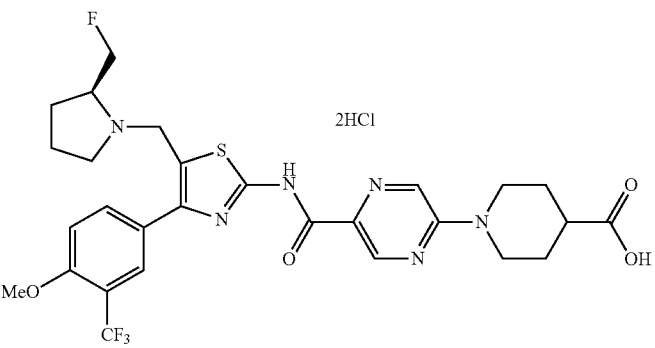 [SMILES: COc1ccc(-c2nc(NC(=O)c3cnc(N4CCC(C(=O)O)CC4)cn3)sc2CN2CCC[C@H]2CF)cc1C(F)(F)F ; "2HCl"] 2HCl |
| 199 | 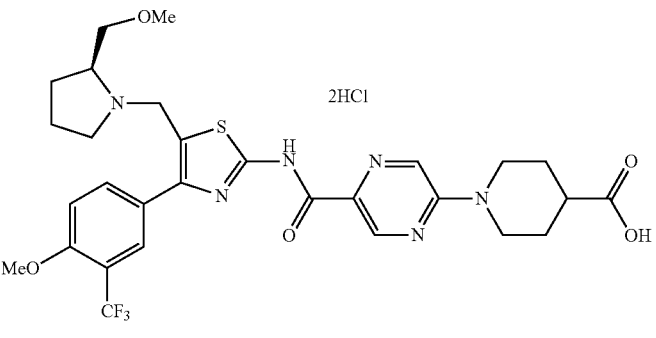 [SMILES: COC[C@@H]1CCCN1Cc1sc(NC(=O)c2cnc(N3CCC(C(=O)O)CC3)cn2)nc1-c1ccc(OC)c(C(F)(F)F)c1 ; "2HCl"] 2HCl |
| 200 | 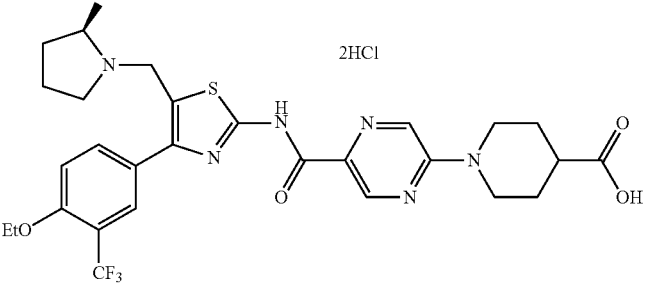 2HCl |

TABLE 80
| Ex | Str |
|---|---|
| 201 | 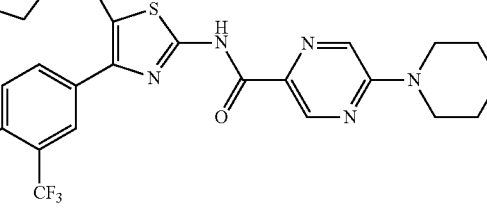 |
| 202 | 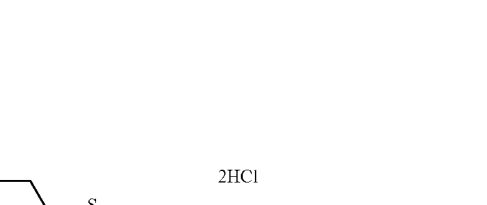 |
| 203 | 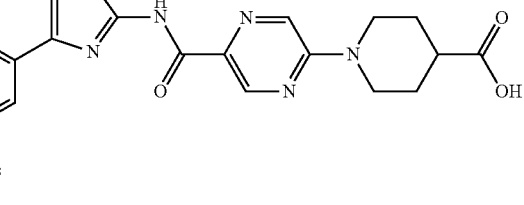 |
| 204 |  |

TABLE 81

| Ex | Str |
|---|---|
| 205 | (structure with 2-methylpyrrolidine-CH2-thiazole core, 4-(2-methoxyethoxy)-3-(trifluoromethyl)phenyl substituent, linked via NHC(O) to pyrazine-piperidine-4-carboxylic acid; 2HCl salt) |
| 206 | (structure with 2-methylpyrrolidine-CH2-thiazole core, 4-chlorothiophen-2-yl substituent, linked via NHC(O) to pyrazine-piperidine-4-carboxylic acid) |
| 207 | (structure with 2-methylpiperidine-CH2-thiazole core, 3-methoxy-5-(trifluoromethyl)phenyl substituent, linked via NHC(O) to pyrazine-piperidine-4-carboxylic acid) |

TABLE 82

| Ex | Syn | DATA |
|---|---|---|
| 1 | 1 | ESI+: 647 |
| 2 | 2 | ESI+: 619<br>NMR-DMSO-d6: 1.06-1.35 (3H, m), 1.49-2.00 (10H, m), 2.58-2.72 (2H, m), 3.09-3.29 (4H, m), 3.89-3.93 (3H, m), 4.35-4.49 (3H, m), 4.64-5.21 (3H, m), 7.34-7.36 (1H, m), 7.47-7.59 (2H, m), 8.40 (1H, d, J = 1.1 Hz), 8.78 (1H, d, J = 1.2 Hz), 10.33-10.51 (1H, m), 12.11-12.19 (1H, m) |
| 3 | 3 | ESI+: 623<br>NMR-DMSO-d6: 1.34 (3H, d, J = 6.4 Hz), 1.58-1.71 (1H, m), 1.83-1.95 (2H, m), 1.97-2.22 (5H, m), 2.44 (3H, s), 3.05-3.18 (1H, m), 3.31-3.45 (3H, m), 3.46-3.56 (1H, m), 3.80-4.30 (2H, m), 4.44-4.54 (3H, m), 4.72-4.80 (1H, m), 7.31 (1H, s), 7.48 (1H, s), 7.61 (1H, s), 8.47 (1H, d, J = 1.3 Hz), 8.80 (1H, d, J = 1.3 Hz), 10.56 (1H, brs), 12.17 (1H, s) |
| 4 | 4 | ESI+: 547, 549<br>NMR-DMSO-d6: 1.47 (3H, d, J = 6.4 Hz), 1.53-1.77 (3H, m), 1.89-2.06 (4H, m), 2.15-2.26 (1H, m), 2.60-2.70 (1H, m), 3.12-3.29 (3H, m), 3.43-3.60 (2H, m), 4.40-4.48 (2H, m), 4.59-4.67 (1H, m), 4.83-4.90 (1H, m), 7.68-7.74 (2H, m), 8.40 (1H, d, J = 1.0 Hz), 8.76 (1H, d, J = 1.1 Hz), 9.45-10.37 (2H, br), 11.22 (1H, brs), 12.09 (1H, s) |
| 5 | 5 | ESI+: 547 |
| 6 | 6 | ESI+: 651 |
| 7 | 7 | ESI+: 647 |
| 8 | 8 | ESI+: 619<br>NMR-DMSO-d6: 0.87 (3H, t, J = 7.4 Hz), 1.25-1.36 (1H, m), 1.39-1.48 (1H, m), 1.53-1.72 (5H, m), 1.86-1.99 (3H, m), 2.14 (1H, q, J = 8.6 Hz), 2.32-2.41 (1H, m), 2.59-2.68 (1H, m), 2.98-3.04 (1H, m), 3.17-3.26 (2H, m), 3.49 (1H, d, J = 14.3 Hz), 3.94 (3H, s), 4.17 (1H, d, J = 14.4 Hz), 4.38-4.45 (2H, m), 7.34 (1H, d, J = 8.8 Hz), 7.98 (1H, dd, J = 2.1, 8.7 Hz), 8.03 (1H, d, J = 2.1 Hz), 8.38 (1H, d, J = 1.3 Hz), 8.74 (1H, d, J = 1.3 Hz), 11.54 (1H, s), 12.32 (1H, brs)<br>m.p.: 194° C. |
| 9 | 1 | ESI+: 641, 643 |

TABLE 83

| Ex | Syn | DATA |
|---|---|---|
| 10 | 1 | ESI+: 609, 611 |
| 11 | 1 | ESI+: 618<br>NMR-DMSO-d6: 1.35 (3H, d, J = 6.4 Hz), 1.51-1.70 (3H, m), 1.84-2.02 (5H, m), 2.12-2.22 (1H, m), 2.58-2.68 (1H, m), 2.76 (6H, s), 3.09-3.29 (3H, m), 3.37-3.58 (2H, m), 3.92-4.90 (6H, m), 7.54 (1H, d, J = 9.0 Hz), 7.92-7.98 (2H, m), 8.40 (1H, s), 8.77 (1H, d, J = 1.0 Hz), 10.54 (1H, brs), 12.11 (1H, s) |
| 12 | 1 | ESI+: 593 |
| 13 | 1 | ESI+: 605 |

TABLE 83-continued

| Ex | Syn | DATA |
|---|---|---|
| 14 | 1 | ESI+: 653 |
| 15 | 1 | ESI+: 649 |
| 16 | 4 | APCI/ESI+: 679 |
| 17 | 1 | ESI+: 647 |
| 18 | 1 | ESI+: 647 |
| 19 | 1 | ESI+: 661 |
| 20 | 1 | ESI+: 661 |
| 21 | 1 | ESI+: 677 |
| 22 | 1 | ESI+: 691 |
| 23 | 1 | ESI+: 691 |
| 24 | 1 | ESI+: 677 |
| 25 | 1 | ESI+: 647 |
| 26 | 1 | ESI+: 661 |
| 27 | 1 | ESI+: 661 |
| 28 | 1 | ESI+: 563 |

TABLE 84

| Ex | Syn | DATA |
|---|---|---|
| 29 | 1 | ESI+: 577 |
| 30 | 1 | ESI+: 619 |
| 31 | 2 | ESI−: 591 |
| 32 | 2 | ESI−: 605 |
| 33 | 2 | ESI−: 637 |
| 34 | 2 | ESI−: 623 |
| 35 | 2 | ESI−: 619 |
| 36 | 2 | ESI−: 581 |
| 37 | 2 | ESI−: 547 |
| 38 | 6 | ESI+: 689<br>NMR-DMSO-d6: 0.77-0.87 (6H, m), 1.51-1.64 (2H, m), 1.76-2.00 (3H, m), 2.57-2.91 (3H, m), 3.11-3.33 (7H, m), 3.56-3.68 (2H, m), 3.96-4.49 (4H, m), 4.63-4.72 (2H, m), 8.23-8.28 (1H, m), 8.34-8.38 (2H, m), 8.39-8.41 (1H, m), 8.77-8.80 (1H, m), 9.90 (1H, brs), 12.26 (1H, s) |
| 39 | 6 | ESI+: 637 |
| 40 | 2 | ESI+: 639 |
| 41 | 2 | ESI+: 653 |
| 42 | 2 | ESI+: 671 |
| 43 | 2 | ESI+: 657 |
| 44 | 2 | ESI+: 609 |
| 45 | 2 | ESI+: 659 |
| 46 | 2 | ESI+: 633 |
| 47 | 2 | ESI+: 651 |

TABLE 85

| Ex | Syn | DATA |
|---|---|---|
| 48 | 2 | ESI+: 659 |
| 49 | 2 | ESI+: 651 |
| 50 | 2 | ESI+: 633 |
| 51 | 2 | ESI+: 625 |
| 52 | 2 | ESI+: 585 |
| 53 | 2 | ESI+: 619 |
| 54 | 2 | ESI+: 619 |
| 55 | 2 | ESI+: 585 |
| 56 | 2 | ESI+: 599 |
| 57 | 2 | APCI/ESI+: 603 |
| 58 | 2 | APCI/ESI+: 603 |
| 59 | 2 | APCI/ESI+: 617 |
| 60 | 2 | APCI/ESI+: 643 |
| 61 | 2 | ESI+: 621 |
| 62 | 2 | ESI+: 635 |
| 63 | 2 | ESI+: 635 |
| 64 | 2 | ESI+: 649 |
| 65 | 2 | ESI+: 649 |
| 66 | 2 | ESI+: 635 |
| 67 | 2 | ESI+: 579 |
| 68 | 2 | ESI+: 579 |

TABLE 86

| Ex | Syn | DATA |
|---|---|---|
| 69 | 2 | ESI+: 633, 635<br>NMR-DMSO-d6: 1.05 (3H, t, J = 7.0 Hz), 1.51-1.71 (3H, m), 1.79-2.02 (4H, m), 2.07-2.18 (1H, m), 2.59-2.69 (1H, m), 3.12-3.28 (3H, m), 3.42-3.81 (8H, m), 3.95-3.98 (3H, m), 4.38-4.47 (2H, m), 4.56-4.64 (1H, m), 4.88-4.95 (1H, m), 7.66-7.71 (2H, m), 8.40 (1H, d, J = 1.2 Hz), 8.77 (1H, d, J = 1.2 Hz), 10.45 (1H, brs), 12.10 (1H, s) |
| 70 | 2 | ESI+: 649 |
| 71 | 2 | ESI+: 665 |
| 72 | 2 | ESI+: 649 |
| 73 | 2 | ESI+: 617 |
| 74 | 2 | ESI+: 655 |
| 75 | 2 | ESI+: 669 |
| 76 | 2 | ESI+: 655 |
| 77 | 2 | ESI+: 587 |
| 78 | 2 | ESI+: 601 |
| 79 | 2 | ESI+: 617 |
| 80 | 2 | ESI+: 623 |
| 81 | 2 | ESI+: 637 |
| 82 | 2 | ESI+: 651 |
| 83 | 2 | ESI+: 637 |
| 84 | 2 | ESI+: 667<br>NMR-DMSO-d6: 1.03 (3H, t, J = 7.0 Hz), 1.52-1.70 (3H, m), 1.80-2.00 (4H, m), 2.07-2.18 (1H, m), 2.60-2.68 (1H, m), 3.14-3.27 (3H, m), 3.39-3.56 (3H, m), 3.59-4.00 (5H, m), 4.02-4.04 (3H, m), 4.39-4.47 (2H, m), 4.57-4.65 (1H, m), 4.89-4.96 (1H, m), 7.78-7.80 (1H, m), 8.07 (1H, dd, J = 12.5, 1.9 Hz), 8.40 (1H, d, J = 1.2 Hz), 8.77 (1H, d, J = 1.2 Hz), 10.44 (1H, brs), 12.15 (1H, s) |

TABLE 87

| Ex | Syn | DATA |
|---|---|---|
| 85 | 2 | ESI+: 649 |
| 86 | 2 | ESI+: 619 |
| 87 | 2 | ESI+: 633 |
| 88 | 2 | ESI+: 619 |
| 89 | 2 | ESI+: 635 |
| 90 | 2 | ESI+: 649 |
| 91 | 2 | ESI+: 635 |
| 92 | 2 | ESI+: 605, 607<br>NMR-DMSO-d6: 1.41 (3H, d, J = 6.4 Hz), 1.52-1.71 (3H, m), 1.86-2.01 (4H, m), 2.14-2.25 (1H, m), 2.59-2.68 (1H, m), 3.08-3.29 (3H, m), 3.39-3.87 (4H, m), 3.90 (3H, s), 4.38-4.51 (3H, m), 4.75-4.82 (1H, m), 7.82-7.85 (2H, m), 8.40 (1H, d, J = 1.2 Hz), 8.77 (1H, d, J = 1.2 Hz), 10.41 (1H, brs), 12.11 (1H, s) |
| 93 | 2 | ESI+: 619 |
| 94 | 2 | ESI+: 619 |
| 95 | 2 | ESI+: 635 |
| 96 | 2 | ESI+: 635 |
| 97 | 2 | ESI+: 619 |
| 98 | 2 | ESI+: 623, 625 |
| 99 | 2 | ESI+: 649 |
| 100 | 2 | ESI+: 633 |
| 101 | 2 | ESI+: 663 |
| 102 | 2 | ESI+: 663 |
| 103 | 103 | ESI+: 649 |

TABLE 88

| Ex | Syn | DATA |
|---|---|---|
| 104 | 2 | ESI+: 589, 591<br>NMR-DMSO-d6: 0.86 (3H, t, J = 7.4 Hz), 1.46-1.74 (4H, m), 1.74-2.01 (4H, m), 2.06-2.24 (1H, m), 2.57-2.70 (1H, m), 3.00-3.30 (4H, m), 3.40-3.60 (4H, m), 4.20-5.50 (7H, m), 7.74 (1H, t, J = 1.9 Hz), 7.76-7.80 (2H, d, J = 1.9 Hz), 8.37-8.43 (1H, m), 8.75-8.79 (1H, m), 10.40-10.70 (1H, m), 12.15 (1H, s) |
| 105 | 2 | ESI+: 674<br>NMR-DMSO-d6: 0.76 (3H, t, J = 7.4 Hz), 1.48-1.76 (5H, |

TABLE 88-continued

| Ex | Syn | DATA |
|---|---|---|
| | | m), 1.80-2.02 (4H, m), 2.06-2.22 (1H, m), 2.56-2.72 (1H, m), 2.83-3.00 (4H, m), 3.08-3.30 (4H, m), 3.45-3.60 (1H, m), 3.66-3.80 (4H, m), 4.00-5.40 (6H, m), 7.67 (1H, d, J = 8.0 Hz), 7.93-8.05 (2H, m), 8.40 (1H, d, J = 1.2 Hz), 8.77 (1H, d, J = 1.2 Hz), 10.39-10.64 (1H, m), 12.14 (1H, s) |
| 106 | 2 | ESI+: 658 |
| 107 | 107 | ESI+: 688<br>NMR-DMSO-d6: 0.88 (3H, t, J = 7.0 Hz), 1.15-1.49 (4H, m), 1.49-1.71 (5H, m), 1.76-1.98 (3H, m), 2.08-2.27 (2H, m), 2.31-2.44 (1H, m), 2.83-2.96 (4H, m), 2.96-3.05 (1H, m), 3.10-3.60 (4H, m), 3.66-3.80 (4H, m), 4.15 (1H, d, J = 14.2 Hz), 4.20-4.32 (2H, m), 7.59 (1H, d, J = 8.4 Hz), 8.02 (1H, dd, J = 1.7, 8.4 Hz), 8.12 (1H, d, J = 1.9 Hz), 8.29 (1H, s), 8.76 (1H, d, J = 1.0 Hz) |
| 108 | 107 | ESI+: 674<br>NMR-DMSO-d6: 1.09 (3H, d, J = 6.2 Hz), 1.21-1.71 (9H, m), 1.77-1.90 (2H, m), 2.00-2.13 (1H, m), 2.13-2.24 (1H, m), 2.38-2.49 (1H, m), 2.72-2.84 (1H, m), 2.85-2.97 (4H, m), 3.10-3.66 (3H, m), 3.66-3.82 (4H, m), 4.08 (1H, d, J = 14.3 Hz), 4.17-4.33 (2H, m), 7.60 (1H, d, J = 8.5 Hz), 7.95-8.07 (1H, m), 8.15-8.25 (1H, m), 8.29 (1H, s), 8.76 (1H, d, J = 1.0 Hz) |
| 109 | 107 | ESI+: 660<br>NMR-DMSO-d6: 1.13 (3H, d, J = 6.0 Hz), 1.30-1.46 (1H, m), 1.48-1.74 (4H, m), 1.77-2.02 (3H, m), 2.10-2.31 (2H, m), 2.41-2.50 (1H, m), 2.84-2.97 (4H, m), 2.97-3.06 (1H, m), 3.10-3.93 (8H, m), 4.16 (1H, d, J = 14.2 Hz), 4.20-4.38 (2H, m), 7.61 (1H, d, J = 8.5 Hz), 8.04 (1H, dd, J = 1.8, 8.4 Hz), 8.15 (1H, d, J = 1.9 Hz), 8.29-8.34 (1H, m), 8.74 (1H, d, J = 1.2 Hz) |

TABLE 89

| Ex | Syn | DATA |
|---|---|---|
| 110 | 107 | ESI+: 689<br>NMR-DMSO-d6: 0.90 (6H, s), 1.15-1.30 (2H, m), 1.47-1.65 (4H, m), 1.75-1.90 (2H, m), 1.96-2.31 (4H, m), 2.31-2.49 (1H, m), 3.00-3.70 (7H, m), 3.75-3.88 (3H, m), 3.97 (1H, dd, J = 4.6, 10.3 Hz), 4.17-4.35 (2H, m), 5.22-5.30 (1H, m), 7.32 (1H, d, J = 8.8 Hz), 7.96-8.02 (1H, m), 8.11-8.18 (1H, m), 8.31 (1H, s), 8.76 (1H, d, J = 1.1 Hz) |
| 111 | 107 | ESI+: 675<br>NMR-DMSO-d6: 0.86 (3H, t, J = 7.4 Hz), 1.19-1.75 (7H, m), 1.76-2.08 (4H, m), 2.08-2.42 (4H, m), 2.90-3.72 (5H, m), 3.75-3.90 (3H, m), 3.97 (1H, dd, J = 4.6, 10.3 Hz), 4.13 (1H, d, J = 14.2 Hz), 4.20-4.35 (2H, m), 5.22-5.30 (1H, m), 7.31 (1H, d, J = 8.8 Hz), 7.98 (1H, dd, J = 1.9, 8.7 Hz), 8.06 (IH, d, J = 2.0 Hz), 8.30 (1H, s), 8.75 (1H, d, J = 1.1 Hz) |
| 112 | 107 | ESI+: 689<br>NMR-DMSO-d6: 0.90 (6H, s), 1.15-1.30 (2H, m), 1.47-1.65 (4H, m), 1.75-1.90 (2H, m), 1.96-2.31 (4H, m), 2.31-2.49 (1H, m), 3.00-3.70 (7H, m), 3.75-3.88 (3H, m), 3.97 (1H, dd, J = 4.6, 10.3 Hz), 4.17-4.35 (2H, m), 5.22-5.30 (1H, m), 7.32 (1H, d, J = 8.9 Hz), 7.96-8.02 (1H, m), 8.11-8.18 (1H, m), 8.31 (1H, s), 8.76 (1H, d, J = 1.1 Hz) |
| 113 | 107 | ESI+: 675<br>NMR-DMSO-d6: 0.86 (3H, t, J = 7.4 Hz), 1.19-1.75 (7H, m), 1.76-2.08 (4H, m), 2.08-2.42 (4H, m), 2.90-3.72 (5H, m), 3.75-3.90 (3H, m), 3.97 (1H, dd, J = 4.6, 10.3 Hz), 4.13 (1H, d, J = 14.3 Hz), 4.20-4.35 (2H, m), 5.22-5.30 (1H, m), 7.31 (1H, d, J = 8.8 Hz), 7.98 (1H, dd, J = 1.9, 8.7 Hz), 8.06 (1H, d, J = 1.9 Hz), 8.30 (1H, s), 8.75 (1H, d, J = 0.9 Hz) |
| 114 | 2 | ESI+: 639<br>NMR-DMSO-d6: 0.76-0.92 (6H, m), 1.51-1.64 (2H, m), 1.77-1.88 (1H, m), 1.91-2.00 (2H, m), 2.59-2.92 (3H, m), 3.17-3.33 (7H, m), 3.53-3.93 (4H, m), 4.38-4.49 (2H, m), 4.70 (2H, brs), 7.80-7.91 (3H, m), 8.40 (1H, d, J = 1.1 Hz), 8.78 (1H, d, J = 1.1 Hz), 9.65 (1H, brs), 12.20 (1H, s) |
| 115 | 2 | ESI+: 607<br>NMR-DMSO-d6: 0.82 (3H, t, J = 7.3 Hz), 1.51-2.01 (9H, m), 2.10-2.21 (1H, m), 2.59-2.68 (1H, m), 3.09-3.28 (4H, m), 3.47-3.59 (1H, m), 3.86-4.65 (5H, m), 4.72-4.85 (1H, m), 7.81 (1H, d, J = 8.5 Hz), 7.93-8.00 (2H, m), 8.40 (1H, s), 8.78 (1H, s), 10.80 (1H, brs), 12.18 (1H, s) |
| 116 | 2 | ESI+: 621<br>NMR-DMSO-d6: 0.83 (3H, t, J = 7.2 Hz), 1.03-1.35 (2H, m), 1.49-1.72 (5H, m), 1.82-2.00 (4H, m), 2.08-2.21 (1H, m), 2.59-2.69 (1H, m), 3.12-3.30 (4H, m), 3.49-3.58 (1H, m), 4.00-4.89 (6H, m), 7.82 (1H, d, J = 8.4 Hz), 7.93-7.99 (2H, m), 8.40 (1H, s), 8.78 (1H, s), 10.82 (1H, brs), 12.18 (1H, s) |

TABLE 90

| Ex | Syn | DATA |
|---|---|---|
| 117 | 2 | ESI+: 625<br>NMR-DMSO-d6: 0.74 (3H, t, J = 7.2 Hz), 1.46-1.66 (4H, m), 1.89-2.01 (2H, m), 2.59-2.69 (1H, m), 2.85-2.96 (2H, m), 3.16-3.29 (7H, m), 3.60-3.69 (2H, m), 4.37-5.26 (6H, m), 7.78-7.95 (3H, m), 8.40 (1H, s), 8.78 (1H, s), 10.71 (1H, brs), 12.17 (1H, s) |
| 118 | 2 | ESI+: 613<br>NMR-DMSO-d6: 1.51-1.65 (2H, m), 1.89-2.01 (2H, m), 2.59-2.69 (1H, m), 3.16-3.28 (2H, m), 3.60-3.73 (1H, m), 3.97 (3H, s), 4.18-4.29 (1H, m), 4.38-4.69 (6H, m), 5.20-7.00 (2H, br), 7.35-7.41 (1H, m), 7.86-8.01 (2H, m), 8.39 (1H, s), 8.75-8.79 (1H, m), 9.80-10.60 (1H, br), 11.98 (1H, s) |
| 119 | 2 | ESI+: 635 |
| 120 | 2 | ESI+: 635 |
| 121 | 2 | ESI+: 621 |
| 122 | 2 | ESI+: 649 |
| 123 | 3 | ESI+: 635 |
| 124 | 3 | ESI+: 649 |
| 125 | 3 | ESI+: 637<br>NMR-DMSO-d6: 0.81 (3H, t, J = 7.3 Hz), 1.52-1.66 (2H, m), 1.69-1.80 (1H, m), 1.82-1.93 (2H, m), 1.98-2.23 (3H, m), 3.08-3.25 (2H, m), 3.30-3.41 (2H, m), 3.45-3.80 (3H, m), 3.97 (3H, s), 4.43-4.57 (3H, m), 4.70-4.80 (1H, m), 7.40 (1H, d, J = 8.7 Hz), 7.92 (1H, d, J = 2.0 Hz), 7.98 (1H, dd, J = 8.6, 2.1 Hz), 8.47 (1H, d, J = 1.2 Hz), 8.80 (1H, d, J = 1.2 Hz), 10.42 (1H, brs), 12.17 (1H, s) |
| 126 | 3 | ESI+: 621 |
| 127 | 3 | ESI+: 635 |
| 128 | 3 | ESI+: 611<br>NMR-DMSO-d6: 1.37 (3H, d, J = 6.4 Hz), 1.60-1.72 (1H, m), 1.86-1.95 (2H, m), 1.98-2.22 (5H, m), 3.09-3.20 (1H, m), 3.30-3.58 (4H, m), 3.82-4.36 (2H, m), 4.43-4.55 (3H, m), 4.75-4.83 (1H, m), 7.78-7.84 (1H, m), 7.92-7.99 (2H, m), 8.47 (1H, d, J = 1.2 Hz), 8.81 (1H, d, J = 1.3 Hz), 10.75 (1H, brs), 12.25 (1H, s) |

TABLE 91

| Ex | Syn | DATA |
|---|---|---|
| 129 | 3 | ESI+: 563, 565<br>NMR-DMSO-d6: 1.43 (3H, d, J = 6.4 Hz), 1.59-1.77 (3H, m), 1.83-2.03 (4H, m), 2.17-2.28 (1H, m), 3.12-3.64 (8H, m), 4.27-4.37 (2H, m), 4.59-4.70 (1H, m), 4.90-4.99 (1H, m), 7.65 (1H, d, J = 1.4 Hz), 7.74 (1H, d, J = 1.4 Hz), 8.42 (1H, d, J = 1.2 Hz), 8.77 (1H, d, J = 1.3 Hz), 10.23 (1H, brs), 12.14 (1H, s) |
| 130 | 3 | ESI+: 621 |

TABLE 91-continued

| Ex | Syn | DATA |
|---|---|---|
| 131 | 3 | ESI+: 623 |
| 132 | 3 | ESI+: 635 |
| 133 | 3 | ESI+: 611 |
|    |   | NMR-DMSO-d6: 1.34 (3H, d, J = 6.4 Hz), 1.58-1.69 (1H, m), 1.84-1.95 (2H, m), 1.98-2.22 (5H, m), 3.06-3.18 (1H, m), 3.30-3.80 (6H, m), 4.42-4.53 (3H, m), 4.73-4.80 (1H, m), 7.64-7.73 (1H, m), 8.06-8.13 (2H, m), 8.47 (1H, d, J = 1.2 Hz), 8.81 (1H, d, J = 1.2 Hz), 10.46 (1H, brs), 12.22 (1H, s) |
| 134 | 3 | ESI+: 609 |
| 135 | 3 | ESI+: 623 |
| 136 | 3 | ESI+: 609, 611 |
| 137 | 4 | ESI+: 575 |
| 138 | 4 | ESI+: 547 |
| 139 | 4 | ESI+: 615 |
| 140 | 4 | ESI+: 561 |
| 141 | 141 | ESI+: 561, 563 |
|    |   | NMR-DMSO-d6: 0.89 (3H, t, J = 7.3 Hz), 1.28-1.78 (7H, m), 1.87-2.00 (3H, m), 2.17-2.27 (1H, m), 2.56-2.69 (1H, m), 3.00-3.09 (1H, m), 3.15-3.36 (2H, m), 3.64 (1H, d, J = 15.1 Hz), 4.19 (1H, d, J = 15.1 Hz), 4.38-4.46 (2H, m), 7.40-7.43 (1H, m), 7.56-7.59 (1H, m), 8.38 (1H, d, J = 1.2 Hz), 8.74 (1H, d, J = 1.2 Hz), 11.55 (1H, s), 12.31 (1H, brs) |
| 142 | 4 | ESI+: 561, 563 |
|    |   | NMR-DMSO-d6: 1.22-2.00 (12H, m), 2.59-2.69 (1H, m), 2.76-2.88 (1H, m), 3.10-3.71 (7H, m), 4.38-4.48 (2H, m), 4.52-4.67 (1H, m), 4.90-5.00 (1H, m), 7.64-7.76 (2H, m), 8.40 (1H, d, J = 1.1 Hz), 8.77 (1H, d, J = 1.2 Hz), 10.08-10.26 (1H, m), 12.12-12.17 (1H, m) |

TABLE 92

| Ex | Syn | DATA |
|---|---|---|
| 143 | 4 | ESI+: 547 |
| 144 | 4 | ESI+: 577 |
| 145 | 4 | ESI+: 577 |
| 146 | 4 | ESI+: 579, 581 |
|    |   | NMR-DMSO-d6: 0.84 (3H, t, J = 7.2 Hz), 1.52-1.74 (4H, m), 1.90-2.00 (2H, m), 2.59-2.69 (1H, m), 3.00-3.10 (2H, m), 3.17-3.27 (2H, m), 3.28-3.40 (4H, m), 3.70-3.75 (2H, m), 4.37-5.11 (7H, m), 7.64 (1H, d, J = 1.4 Hz), 7.75 (1H, d, J = 1.4 Hz), 8.40 (1H, d, J = 1.2 Hz), 8.77 (1H, d, J = 1.2 Hz), 10.53 (1H, brs), 12.14 (1H, s) |
| 147 | 4 | ESI+: 563 |
| 148 | 4 | ESI+: 605 |
| 149 | 141 | ESI+: 619 |
| 150 | 4 | ESI+: 593 |
|    |   | NMR-DMSO-d6: 1.36 (3H, d, J = 6.4 Hz), 1.51-1.70 (3H, m), 1.85-2.00 (4H, m), 2.12-2.23 (1H, m), 2.59-2.68 (1H, m), 3.08-3.27 (3H, m), 3.38-3.80 (4H, m), 4.38-4.54 (3H, m), 4.77-4.85 (1H, m), 7.79-7.85 (1H, m), 7.91-7.97 (2H, m), 8.40 (1H, d, J = 1.3 Hz), 8.78 (1H, d, J = 1.3 Hz), 10.51 (1H, brs), 12.20 (1H, s) |
| 151 | 4 | ESI+: 625 |
| 152 | 4 | ESI+: 593, 595 |
|    |   | NMR-DMSO-d6: 0.82-1.00 (6H, m), 1.51-1.65 (2H, m), 1.89-2.06 (3H, m), 2.59-2.69 (1H, m), 2.79-3.11 (2H, m), 3.16-3.44 (7H, m), 3.56-4.08 (4H, m), 4.38-4.48 (2H, m), 4.73-4.89 (2H, m), 7.57-7.81 (2H, m), 8.38-8.42 (1H, m), 8.74-8.79 (1H, m), 9.84 (1H, brs), 12.15 (1H, s) |
| 153 | 4 | ESI+: 589 |
| 154 | 4 | ESI+: 577 |
| 155 | 4 | ESI+: 561 |
| 156 | 4 | ESI+: 619 |
|    |   | NMR-DMSO-d6: 0.80 (3H, t, J = 7.3 Hz), 1.45-2.01 (9H, m), 2.04-2.20 (1H, m), 2.56-2.70 (1H, m), 3.05-3.28 (4H, m), 3.44-3.56 (1H, m), 3.97 (3H, s), 4.07-4.77 (6H, m), 7.40 (1H, d, J = 8.8 Hz), 7.93 (1H, d, J = 2.0 Hz), 7.99 (1H, dd, J = 8.7, 2.0 Hz), 8.40 (1H, d, J = 1.2 Hz), 8.77 (1H, d, J = 1.2 Hz), 10.62 (1H, brs), 12.10 (1H, s) |

TABLE 93

| Ex | Syn | DATA |
|---|---|---|
| 157 | 4 | ESI+: 603 |
| 158 | 4 | ESI+: 633 |
|    |   | NMR-DMSO-d6: 0.81 (3H, t, J = 7.2 Hz), 0.97-1.11 (1H, m), 1.19-1.32 (1H, m), 1.50-1.66 (5H, m), 1.82-2.00 (4H, m), 2.06-2.20 (1H, m), 2.58-2.69 (1H, m), 3.08-3.28 (4H, m), 3.46-3.57 (1H, m), 3.97 (3H, s), 4.03-4.86 (6H, m), 7.40 (1H, d, J = 8.7 Hz), 7.93 (1H, d, J = 2.0 Hz), 7.98 (1H, dd, J = 8.6, 2.0 Hz), 8.40 (1H, d, J = 1.1 Hz), 8.77 (1H, d, J = 1.2 Hz), 10.55 (1H, brs), 12.11 (1H, s) |
| 159 | 4 | ESI+: 637 |
| 160 | 4 | ESI+: 605 |
| 161 | 4 | ESI+: 633 |
| 162 | 4 | ESI+: 605 |
| 163 | 4 | ESI+: 619 |
| 164 | 4 | ESI+: 619 |
| 165 | 4 | ESI+: 649 |
| 166 | 4 | ESI+: 649 |
| 167 | 4 | ESI+: 630 |
| 168 | 4 | ESI+: 591 |
| 169 | 4 | ESI+: 605 |
| 170 | 4 | ESI+: 623 |
| 171 | 4 | ESI+: 641 |
| 172 | 4 | ESI+: 641 |
| 173 | 4 | ESI+: 627 |
| 174 | 4 | ESI+: 609 |

TABLE 94

| Ex | Syn | DATA |
|---|---|---|
| 175 | 4 | ESI+: 609 |
| 176 | 4 | ESI+: 605 |
| 177 | 4 | ESI+: 605 |
| 178 | 4 | ESI+: 635 |
| 179 | 4 | ESI+: 659 |
|    |   | NMR-DMSO-d6: 1.51-1.65 (2H, m), 1.67-2.16 (7H, m), 2.39-2.48 (1H, m), 2.58-2.69 (1H, m), 3.00-3.08 (1H, m), 3.16-3.27 (2H, m), 3.51-3.66 (1H, m), 3.95 (3H, s), 3.98-4.05 (1H, m), 4.29 (1H, d, J = 14.6 Hz), 4.38-4.46 (2H, m), 4.80-6.12 (2H, m), 7.33 (1H, d, J = 8.5 Hz), 7.90-7.97 (2H, m), 8.39 (1H, d, J = 1.2 Hz), 8.75 (1H, d, J = 1.2 Hz), 11.63 (1H, brs) |
| 180 | 4 | ESI+: 623 |
| 181 | 4 | ESI+: 647 |
| 182 | 4 | ESI+: 633 |
| 183 | 4 | ESI+: 649 |
| 184 | 4 | ESI+: 619 |
| 185 | 4 | ESI+: 673 |
| 186 | 4 | ESI+: 659 |
| 187 | 4 | ESI+: 633 |
| 188 | 4 | ESI+: 633 |
|    |   | NMR-DMSO-d6: 0.79 (3H, d, J = 6.7 Hz), 0.86 (3H, d, J = 6.7 Hz), 1.51-2.00 (9H, m), 2.59-2.70 (1H, m), 3.12-3.28 (4H, m), 3.31-3.86 (3H, m), 3.97 (3H, s), 4.38-4.47 (2H, m), 4.52-4.62 (1H, m), 4.68-4.77 (1H, m), 7.39 (1H, d, J = 8.7 Hz), 7.90 (1H, d, J = 2.0 Hz), 7.95 (1H, dd, J = 8.7, 2.0 Hz), 8.40 (1H, d, J = 1.1 Hz), 8.78 (1H, d, J = 1.2 Hz), 9.80 (1H, brs), 12.12 (1H, s) |
| 189 | 4 | ESI+: 631 |
| 190 | 4 | ESI+: 659 |

TABLE 95

| Ex | Syn | DATA |
|---|---|---|
| 191 | 4 | ESI+: 647 |
| 192 | 4 | ESI+: 647 |
| 193 | 4 | ESI+: 582 |
| 194 | 4 | ESI+: 527 |
| 195 | 4 | ESI+: 541 |
| 196 | 4 | ESI−: 559 |
|    |   | NMR-DMSO-d6: 0.89 (3H, t, J = 7.4 Hz), 1.50-2.27 |

TABLE 95-continued

| Ex | Syn | DATA |
|---|---|---|
| | | (10H, m), 2.60-2.69 (1H, m), 3.12-4.00 (7H, m), 4.39-4.48 (2H, m), 4.66-4.75 (1H, m), 4.92-5.00 (1H, m), 7.66 (1H, d, J = 1.4 Hz), 7.74 (1H, d, J = 1.4 Hz), 8.40 (1H, d, J = 1.1 Hz), 8.77 (1H, d, J = 1.1 Hz), 10.10 (1H, brs), 12.15 (1H, s) |
| 197 | 4 | ESI−: 563<br>NMR-DMSO-d6: 1.24 (3H, t, J = 7.2 Hz), 1.51-1.65 (2H, m), 1.89-2.01 (2H, m), 2.59-2.68 (1H, m), 3.15-3.43 (9H, m), 3.66-4.14 (4H, m), 4.37-4.48 (2H, m), 4.70-4.84 (2H, m), 7.63 (1H, d, J = 1.2 Hz), 7.74 (1H, d, J = 1.3 Hz), 8.39-8.41 (1H, m), 8.77 (1H, d, J = 1.1 Hz), 10.28 (1H, brs), 12.14 (1H, s) |
| 198 | 4 | ESI+: 623<br>NMR-DMSO-d6: 1.51-2.00 (8H, m), 2.58-2.69 (1H, m), 2.92-3.53 (5H, m), 3.82-4.35 (5H, m), 4.39-3.69 (4H, m), 4.94-5.12 (2H, m), 7.39 (1H, d, J = 8.7 Hz), 7.84-7.96 (2H, m), 8.38-8.41 (1H, m), 8.77 (1H, d, J = 1.2 Hz), 10.14 (1H, brs), 12.09 (1H, brs) |
| 199 | 4 | ESI+: 635<br>NMR-DMSO-d6: 1.52-1.69 (3H, m), 1.80-2.01 (4H, m), 2.06-2.16 (1H, m), 2.58-2.68 (1H, m), 3.16-3.28 (5H, m), 3.48-3.78 (4H, m), 3.94-4.01 (4H, m), 4.31-4.99 (6H, m), 7.39 (1H, d, J = 8.8 Hz), 7.92 (1H, d, J = 2.0 Hz), 8.03 (1H, dd, J = 8.6, 2.0 Hz), 8.39-8.40 (1H, m), 8.77 (1H, d, J = 1.2 Hz), 10.62 (1H, brs), 12.09 (1H, s) |
| 200 | 4 | ESI+: 619<br>NMR-DMSO-d6: 1.34 (3H, d, J = 6.4 Hz), 1.38 (3H, t, J = 6.9 Hz), 1.51-1.67 (3H, m), 1.84-1.99 (4H, m), 2.11-2.22 (1H, m), 2.59-2.68 (1H, m), 3.07-3.28 (3H, m), 3.38-3.55 (2H, m), 3.80-4.55 (7H, m), 4.71-4.80 (1H, m), 7.38 (1H, d, J = 8.7 Hz), 7.79-7.97 (2H, m), 8.38-8.42 (1H, m), 8.77 (1H, d, J = 1.1 Hz), 10.33 (1H, brs), 12.09 (1H, s) |

TABLE 96

| Ex | Syn | DATA |
|---|---|---|
| 201 | 4 | ESI+: 651<br>NMR-DMSO-d6: 1.35 (3H, d, J = 6.5 Hz), 1.53-1.68 (3H, m), 1.86-1.99 (5H, m), 2.10-2.23 (3H, m), 2.60-2.67 (1H, m), 3.07-3.25 (3H, m), 3.38-3.55 (2H, m), 4.29 (2H, t, J = 6.0 Hz), 4.37-5.01 (7H, m), 7.42 (1H, d, J = 8.6 Hz), 7.92-8.00 (2H, m), 8.40 (1H, d, J = 1.0 Hz), 8.77 (1H, d, J = 1.0 Hz), 10.52 (1H, brs), 12.10 (1H, brs) |
| 202 | 4 | ESI+: 605<br>NMR-DMSO-d6: 1.34 (3H, d, J = 6.5 Hz), 1.51-1.68 (3H, m), 1.83-1.99 (4H, m), 2.12-2.22 (1H, m), 2.59-2.68 (1H, m), 3.07-3.27 (3H, m), 3.37-3.56 (2H, m), 3.62-3.92 (2H, m), 3.97 (3H, s), 4.38-4.52 (3H, m), 4.72-4.79 (1H, m), 7.40 (1H, d, J = 8.8 Hz), 7.92 (1H, d, J = 2.0 Hz), 7.95-7.99 (1H, m), 8.37-8.42 (1H, m), 8.77 (1H, d, J = 1.2 Hz), 10.25 (1H, brs), 12.10 (1H, s) |
| 203 | 4 | ESI+: 633<br>NMR-DMSO-d6: 0.80 (3H, t, J = 7.5 Hz), 1.38 (3H, t, J = 7.0 Hz), 1.48-1.66 (4H, m), 1.68-1.80 (1H, m), 1.83-1.99 (4H, m), 2.09-2.20 (1H, m), 2.58-2.69 (1H, m), 3.08-3.28 (4H, m), 3.44-3.56 (1H, m), 3.67-4.23 (2H, m), 4.25 (2H, q, J = 7.0 Hz), 4.37-4.80 (4H, m), 7.38 (1H, d, J = 8.7 Hz), 7.88-7.98 (2H, m), 8.37-8.43 (1H, m), 8.77 (1H, d, J = 1.1 Hz), 10.37 (1H, brs), 12.10 (1H, s) |
| 204 | 4 | ESI+: 705<br>NMR-DMSO-d6: 1.49-2.22 (10H, m), 2.38-3.65 (7H, m), 3.98-4.06 (1H, m), 4.23-4.32 (2H, m), 4.37-4.47 (2H, m), 4.54-4.72 (2H, m), 4.93-6.00 (2H, br), 7.35 (1H, d, J = 8.6 Hz), 7.91 (1H, d, J = 8.8 Hz), 7.95 (1H, s), 8.39 (1H, s), 8.75 (1H, s), 9.99-11.00 (1H, m), 11.62 (1H, s) |
| 205 | 4 | ESI+: 649<br>NMR-DMSO-d6: 1.34 (3H, d, J = 6.4 Hz), 1.51-1.67 (3H, m), 1.84-2.00 (4H, m), 2.10-2.22 (1H, m), 2.59-2.69 (1H, m), 3.06-3.27 (3H, m), 3.34 (3H, s), 3.38-3.55 (2H, m), 3.61-3.90 (4H, m), 4.29-4.35 (2H, m), 4.38-4.52 (2H, m), 4.71-4.79 (1H, m), 7.41 (1H, d, J = 8.8 Hz), 7.90-7.98 (2H, |

TABLE 96-continued

| Ex | Syn | DATA |
|---|---|---|
| | | m), 8.38-8.42 (1H, m), 8.77 (1H, d, J = 1.2 Hz), 10.33 (1H, brs), 12.10 (1H, s) |
| 206 | 8 | ESI+: 547, 549<br>NMR-DMSO-d6: 1.16 (3H, d, J = 6.0 Hz), 1.34-1.44 (1H, m), 1.52-1.72 (4H, m), 1.90-2.01 (3H, m), 2.17-2.25 (1H, m), 2.54-2.68 (2H, m), 3.00-3.06 (1H, m), 3.17-3.26 (2H, m), 3.59 (1H, d, J = 14.9 Hz), 4.19 (1H, d, J = 14.9 Hz), 4.37-4.45 (2H, m), 7.45 (1H, d, J = 1.5 Hz), 7.58 (1H, d, J = 1.4 Hz), 8.38 (1H, d, J = 1.2 Hz), 8.74 (1H, d, J = 1.2 Hz), 11.57 (1H, brs), 12.20-12.45 (1H, br)<br>m.p.: 201° C. |

TABLE 97

| Ex | Syn | DATA |
|---|---|---|
| 207 | 8 | ESI+: 619<br>NMR-DMSO-d6: 1.09 (3H, d, J = 6.0 Hz), 1.25-1.67 (8H, m), 1.90-1.99 (2H, m), 2.07-2.14 (1H, m), 2.33-2.68 (2H, m), 2.73-2.79 (1H, m), 3.17-3.40 (2H, m), 3.49 (1H, d, J = 14.4 Hz), 3.90 (3H, s), 4.14 (1H, d, J = 14.5 Hz), 4.38-4.46 (2H, m), 7.23 (1H, s), 7.60 (1H, s), 7.78 (1H, s), 8.39 (1H, s), 8.75 (1H, s), 11.58 (1H, s), 12.22-12.45 (1H, br) m.p.: 136° C. |

TABLE 98

| No. | R1 | R2 |
|---|---|---|
| A1 | 1-methylpyrrolidin-3-yl-SO₂Me | 4-methyl-2-methoxy-3-(trifluoromethyl)phenyl (MeO, CF₃) |
| A2 | 2-oxa-5-azabicyclo (N-methyl) | 4-methyl-2-methoxy-3-(trifluoromethyl)phenyl (MeO, CF₃) |
| A3 | 4-methylmorpholin-2-yl | 4-methyl-2-methoxy-3-(trifluoromethyl)phenyl (MeO, CF₃) |
| A4 | 1-oxa-9-azaspiro[4.5] (N-methyl) | 4-methyl-2-methoxy-3-(trifluoromethyl)phenyl (MeO, CF₃) |

TABLE 98-continued

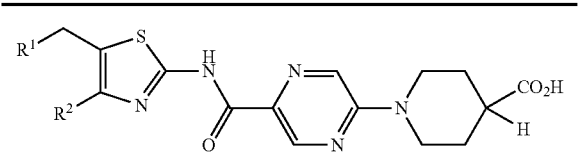

| No. | R1 | R2 |
|---|---|---|
| A5 | 1-methyl-4-piperazinyl (Me on N) | 4-methyl-2-(trifluoromethyl)-methoxyphenyl (MeO, CF3) |
| A6 | 4-(methoxycarbonyl)piperazin-1-yl (CO2Me) | MeO, CF3 phenyl |
| A7 | 4-(dimethylcarbamoyl)piperazin-1-yl (CONMe2) | MeO, CF3 phenyl |
| A8 | 3-(methylsulfonyl)-1-methylpyrrolidinyl (SO2Me) | MeO, CF3 phenyl |
| A9 | 3-methyl-2-oxa-5-azabicyclo group | MeO, CF3 phenyl |
| A10 | morpholinyl | MeO, CF3 phenyl |
| A11 | 1-oxa-9-azaspiro[5.4] with N-Me | MeO, CF3 phenyl |

TABLE 98-continued

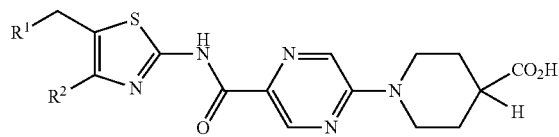

| No. | R1 | R2 |
|---|---|---|
| A12 | 4-methylpiperazin-1-yl (Me) | MeO, CF3 phenyl |
| A13 | 4-(methoxycarbonyl)piperazin-1-yl (CO2Me) | MeO, CF3 phenyl |
| A14 | 4-(dimethylcarbamoyl)piperazin-1-yl (CONMe2) | MeO, CF3 phenyl |

TABLE 99

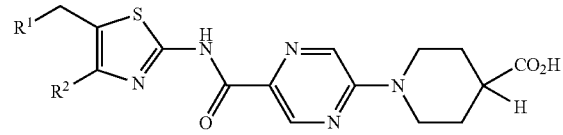

| No. | R1 | R2 |
|---|---|---|
| A15 | 4-(methylsulfonyl)piperazin-1-yl (SO2Me) | MeO, CF3 phenyl |
| A16 | 4-(dimethylsulfamoyl)piperazin-1-yl (SO2NMe2) | MeO, CF3 phenyl |
| A17 | 1,1-dioxothiomorpholinyl | MeO, CF3 phenyl |

TABLE 99-continued

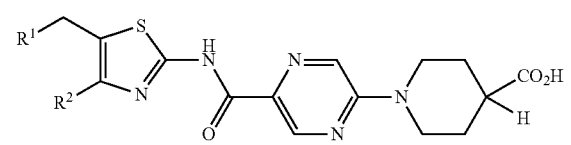

| No. | R1 | R2 |
|---|---|---|
| A18 | N-methylazepane | 4-Me-2-CF3-MeO-phenyl |
| A19 | N-methyl-1,4-oxazepane | 4-Me-2-CF3-MeO-phenyl |
| A20 | 1-methyl-1,4-diazepan-5-one | 4-Me-2-CF3-MeO-phenyl |
| A21 | 1-Ac-4-Me-1,4-diazepane | 4-Me-2-CF3-MeO-phenyl |
| A22 | 1-SO2Me-4-Me-1,4-diazepane | 4-Me-2-CF3-MeO-phenyl |
| A23 | 1-SO2Me-4-Me-piperazine | 3-MeO-5-CF3-phenyl |
| A24 | 1-SO2NMe2-4-Me-piperazine | 3-MeO-5-CF3-phenyl |

TABLE 99-continued

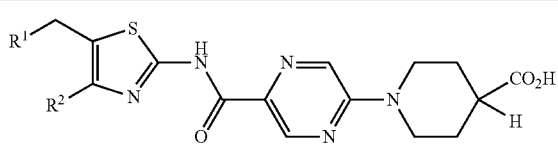

| No. | R1 | R2 |
|---|---|---|
| A25 | 4-methyl-thiomorpholine-1,1-dioxide | 3-MeO-5-CF3-phenyl |
| A26 | N-methylazepane | 3-MeO-5-CF3-phenyl |
| A27 | N-methyl-1,4-oxazepane | 3-MeO-5-CF3-phenyl |
| A28 | 1-methyl-1,4-diazepan-5-one | 3-MeO-5-CF3-phenyl |
| A29 | 1-Ac-4-Me-1,4-diazepane | 3-MeO-5-CF3-phenyl |
| A30 | 1-SO2Me-4-Me-1,4-diazepane | 3-MeO-5-CF3-phenyl |

TABLE 100

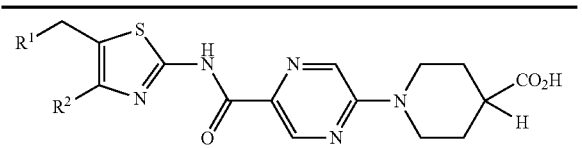

| No. | R1 | R2 |
|---|---|---|
| B1 | 1-methyl-pyrrolidin-3-yl SO2Me | 4-chloro-5-methylthiophen-2-yl |
| B2 | 2-methyl-2-azabicyclo[2.2.1], O-containing | 4-chloro-5-methylthiophen-2-yl |
| B3 | 4-methylmorpholin-2-yl | 4-chloro-5-methylthiophen-2-yl |
| B4 | 9-methyl-1-oxa-9-azaspiro[5.4]decane | 4-chloro-5-methylthiophen-2-yl |
| B5 | 1,4-dimethylpiperazin-2-yl | 4-chloro-5-methylthiophen-2-yl |
| B6 | 4-methyl-1-(methoxycarbonyl)piperazin-2-yl | 4-chloro-5-methylthiophen-2-yl |
| B7 | 4-methyl-1-(dimethylcarbamoyl)piperazin-2-yl | 4-chloro-5-methylthiophen-2-yl |
| B8 | 1-methyl-pyrrolidin-3-yl SO2Me | 3-chloro-5-fluoro-4-methoxyphenyl-methyl |

TABLE 100-continued

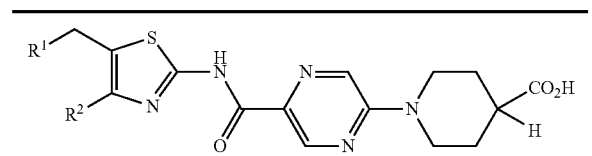

| No. | R1 | R2 |
|---|---|---|
| B9 | 2-methyl-2-azabicyclo O-containing | 3-chloro-5-fluoro-4-methoxyphenyl-methyl |
| B10 | 4-methylmorpholin-2-yl | 3-chloro-5-fluoro-4-methoxyphenyl-methyl |
| B11 | 9-methyl-1-oxa-9-azaspiro[5.4]decane | 3-chloro-5-fluoro-4-methoxyphenyl-methyl |
| B12 | 1,4-dimethylpiperazin-2-yl | 3-chloro-5-fluoro-4-methoxyphenyl-methyl |
| B13 | 4-methyl-1-(methoxycarbonyl)piperazin-2-yl | 3-chloro-5-fluoro-4-methoxyphenyl-methyl |
| B14 | 4-methyl-1-(dimethylcarbamoyl)piperazin-2-yl | 3-chloro-5-fluoro-4-methoxyphenyl-methyl |

TABLE 101

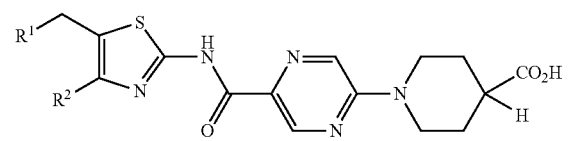

| No. | R1 | R2 |
|---|---|---|
| B15 | N-piperazine-SO2Me, N-Me | 4-Cl-thiophen-2-yl |
| B16 | N-piperazine-SO2NMe2, N-Me | 4-Cl-thiophen-2-yl |
| B17 | 1,1-dioxo-thiomorpholine, N-Me | 4-Cl-thiophen-2-yl |
| B18 | N-methyl azepane | 4-Cl-thiophen-2-yl |
| B19 | 1,4-oxazepane, N-Me | 4-Cl-thiophen-2-yl |
| B20 | 5-oxo-1,4-diazepane, N-Me | 4-Cl-thiophen-2-yl |
| B21 | N-Ac, N'-Me diazepane | 4-Cl-thiophen-2-yl |

TABLE 101-continued

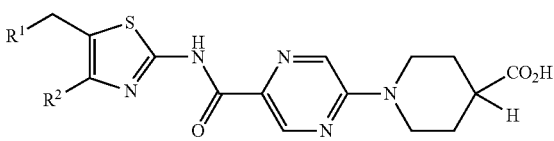

| No. | R1 | R2 |
|---|---|---|
| B22 | N-diazepane-SO2Me, N'-Me | 4-Cl-thiophen-2-yl |
| B23 | N-piperazine-SO2Me, N-Me | 3-F-5-Cl-4-MeO-phenyl |
| B24 | N-piperazine-SO2NMe2, N-Me | 3-F-5-Cl-4-MeO-phenyl |
| B25 | 1,1-dioxo-thiomorpholine, N-Me | 3-F-5-Cl-4-MeO-phenyl |
| B26 | N-methyl azepane | 3-F-5-Cl-4-MeO-phenyl |
| B27 | 1,4-oxazepane, N-Me | 3-F-5-Cl-4-MeO-phenyl |
| B28 | 5-oxo-1,4-diazepane, N-Me | 3-F-5-Cl-4-MeO-phenyl |

TABLE 101-continued

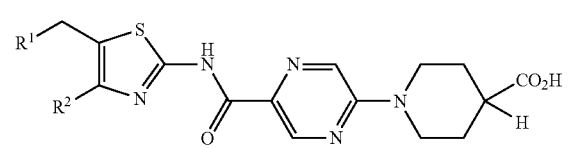

| No. | R1 | R2 |
|---|---|---|
| B29 | N-Ac / N-Me (1,4-diazepane) | 3-F, 4-OMe, 5-Cl phenyl |
| B30 | N-SO2Me / N-Me (1,4-diazepane) | 3-F, 4-OMe, 5-Cl phenyl |

TABLE 102

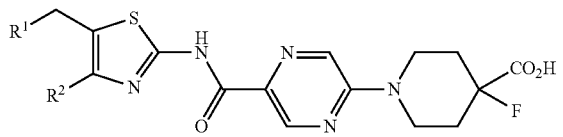

| No. | R1 | R2 |
|---|---|---|
| C1 | 1-Me-pyrrolidin-3-yl-SO2Me | 4-OMe, 3-CF3 phenyl |
| C2 | 3-Me-2-oxa-5-azabicyclo[2.2.1]heptane | 4-OMe, 3-CF3 phenyl |
| C3 | 4-Me-morpholine | 4-OMe, 3-CF3 phenyl |
| C4 | 1-oxa-9-azaspiro[5.4] with N-Me | 4-OMe, 3-CF3 phenyl |

TABLE 102-continued

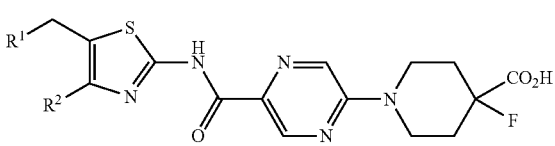

| No. | R1 | R2 |
|---|---|---|
| C5 | 4-Me-piperazine | 4-OMe, 3-CF3 phenyl |
| C6 | 4-Me-piperazine-1-CO2Me | 4-OMe, 3-CF3 phenyl |
| C7 | 4-Me-piperazine-1-CONMe2 | 4-OMe, 3-CF3 phenyl |
| C8 | 1-Me-pyrrolidin-3-yl-SO2Me | 3,5-bis substituted (OMe, CF3) phenyl |
| C9 | 3-Me-2-oxa-5-azabicyclo[2.2.1]heptane | 3,5-bis substituted (OMe, CF3) phenyl |
| C10 | 4-Me-morpholine | 3,5-bis substituted (OMe, CF3) phenyl |
| C11 | 1-oxa-9-azaspiro[5.4] with N-Me | 3,5-bis substituted (OMe, CF3) phenyl |

TABLE 102-continued

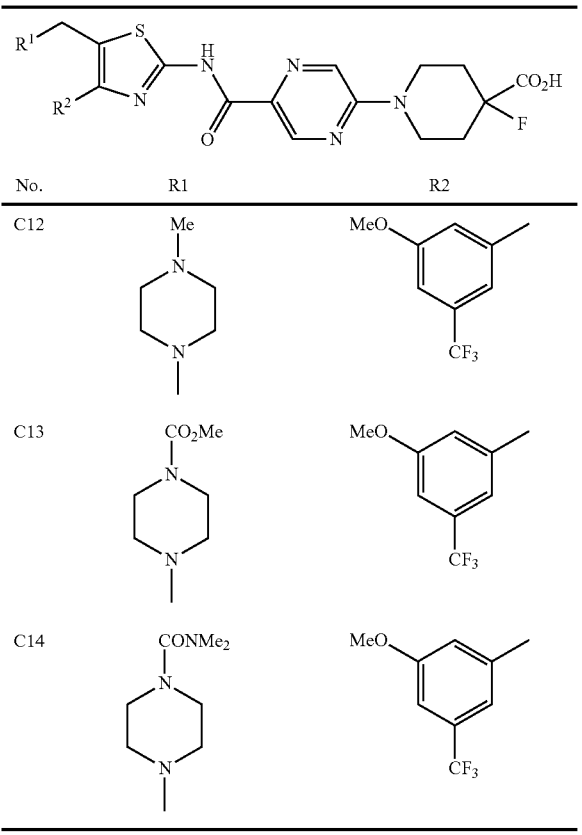

| No. | R1 | R2 |
|---|---|---|
| C12 | 4-methylpiperazin-1-yl-CH2- (Me on top N) | 3-MeO-5-CF3-phenyl |
| C13 | 4-methylpiperazin-1-yl-CH2- (CO2Me on top N) | 3-MeO-5-CF3-phenyl |
| C14 | 4-methylpiperazin-1-yl-CH2- (CONMe2 on top N) | 3-MeO-5-CF3-phenyl |

TABLE 103

| No. | R1 | R2 |
|---|---|---|
| C15 | 4-methylpiperazin-1-yl-CH2- (SO2Me on top N) | 4-MeO-3-CF3-phenyl |
| C16 | 4-methylpiperazin-1-yl-CH2- (SO2NMe2 on top N) | 4-MeO-3-CF3-phenyl |
| C17 | 1,1-dioxo-thiomorpholin-4-yl-CH2- | 4-MeO-3-CF3-phenyl |

TABLE 103-continued

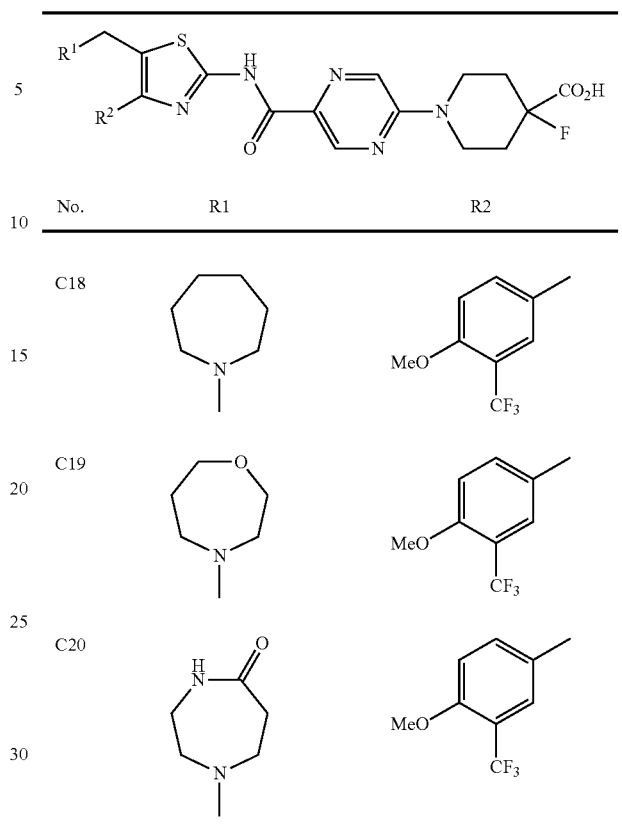

| No. | R1 | R2 |
|---|---|---|
| C18 | 4-methyl-azepan-1-yl-CH2- | 4-MeO-3-CF3-phenyl |
| C19 | 4-methyl-1,4-oxazepan-1-yl-CH2- | 4-MeO-3-CF3-phenyl |
| C20 | 4-methyl-7-oxo-1,4-diazepan-1-yl-CH2- | 4-MeO-3-CF3-phenyl |
| C21 | 4-methyl-1,4-diazepan-1-yl-CH2- (Ac on top N) | 4-MeO-3-CF3-phenyl |
| C22 | 4-methyl-1,4-diazepan-1-yl-CH2- (SO2Me on top N) | 4-MeO-3-CF3-phenyl |
| C23 | 4-methylpiperazin-1-yl-CH2- (SO2Me on top N) | 3-MeO-5-CF3-phenyl |
| C24 | 4-methylpiperazin-1-yl-CH2- (SO2NMe2 on top N) | 3-MeO-5-CF3-phenyl |

TABLE 103-continued

| No. | R1 | R2 |
|-----|----|----|
| C25 | 4-methyl-1,1-dioxo-thiomorpholine | 3-MeO-5-CF3-phenyl |
| C26 | 1-methylazepane | 3-MeO-5-CF3-phenyl |
| C27 | 4-methyl-1,4-oxazepane | 3-MeO-5-CF3-phenyl |
| C28 | 1-methyl-1,4-diazepan-5-one | 3-MeO-5-CF3-phenyl |
| C29 | 1-Ac-4-methyl-1,4-diazepane | 3-MeO-5-CF3-phenyl |
| C30 | 1-SO2Me-4-methyl-1,4-diazepane | 3-MeO-5-CF3-phenyl |

TABLE 104

| No. | R1 | R2 |
|-----|----|----|
| D1 | 3-SO2Me-1-methylpyrrolidine | 4-Cl-5-methylthiophen-2-yl |
| D2 | N-methyl-2-oxa-5-azabicyclo[2.2.1]heptane | 4-Cl-5-methylthiophen-2-yl |
| D3 | 4-methylmorpholine | 4-Cl-5-methylthiophen-2-yl |
| D4 | 9-methyl-1-oxa-9-azaspiro[5.4]decane | 4-Cl-5-methylthiophen-2-yl |
| D5 | 1,4-dimethylpiperazine | 4-Cl-5-methylthiophen-2-yl |
| D6 | 1-CO2Me-4-methylpiperazine | 4-Cl-5-methylthiophen-2-yl |
| D7 | 1-CONMe2-4-methylpiperazine | 4-Cl-5-methylthiophen-2-yl |
| D8 | 3-SO2Me-1-methylpyrrolidine | 3-F-5-methyl-2-MeO-6-Cl-phenyl |

TABLE 104-continued
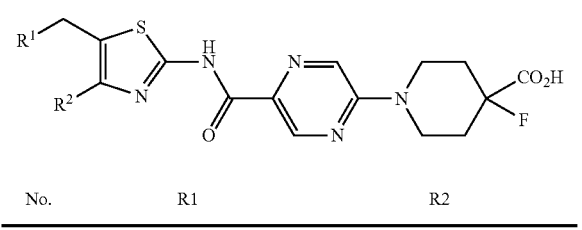
| No. | R1 | R2 |
|---|---|---|
| D9 | 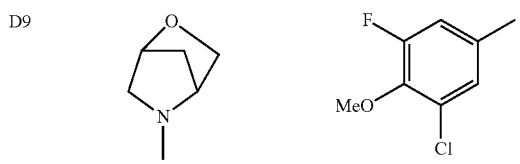 | 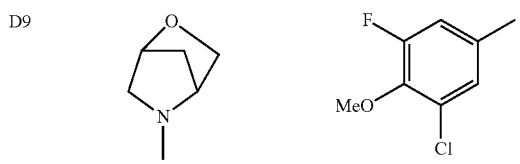 |
| D10 | 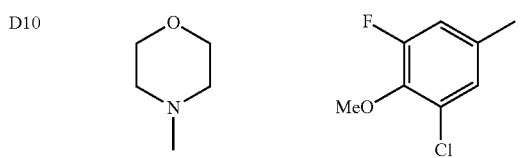 | 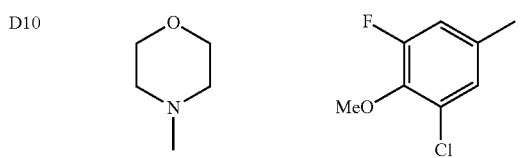 |
| D11 | 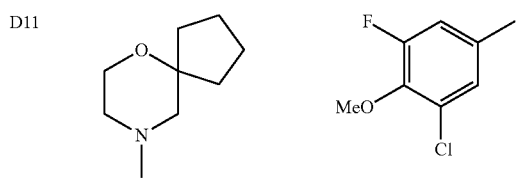 | 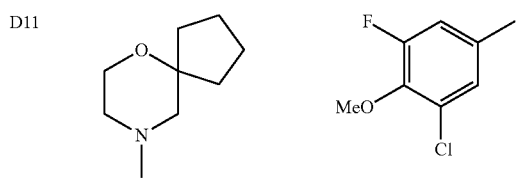 |
| D12 | 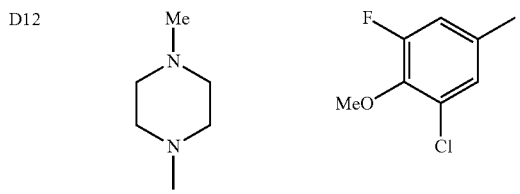 | 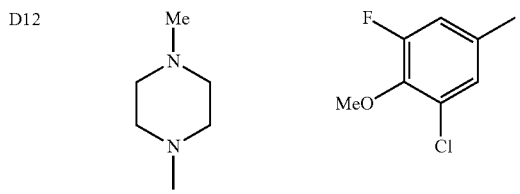 |
| D13 | 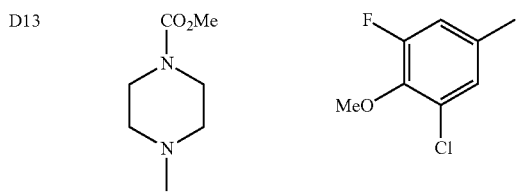 | 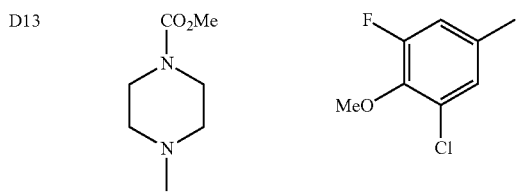 |
| D14 | 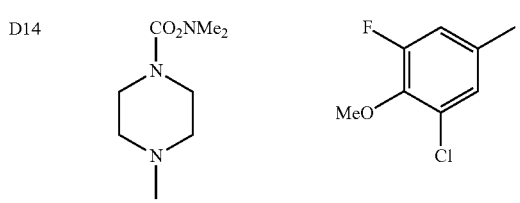 | 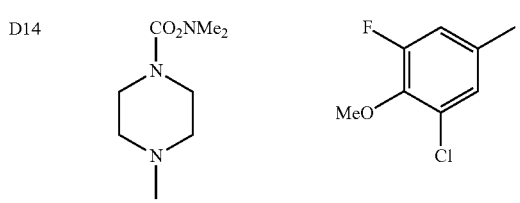 |
TABLE 105
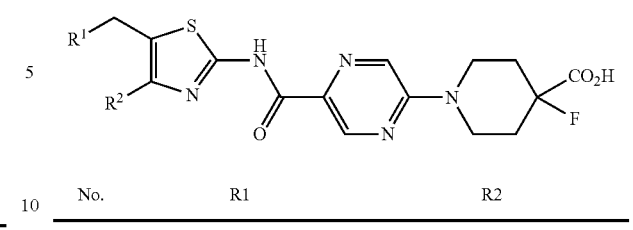
| No. | R1 | R2 |
|---|---|---|
| D15 | 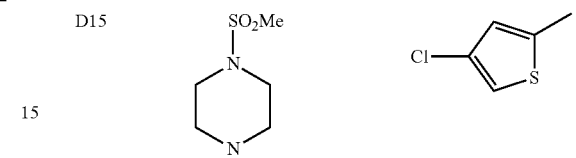 | 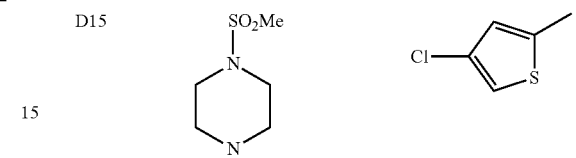 |
| D16 | 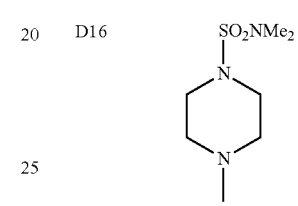 | 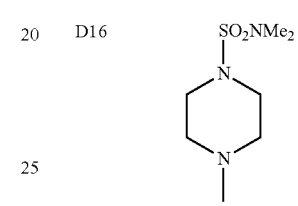 |
| D17 | 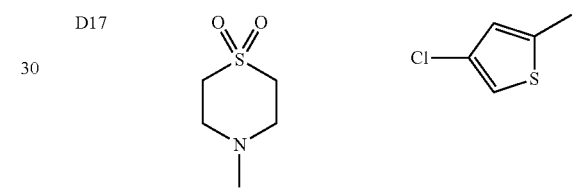 | 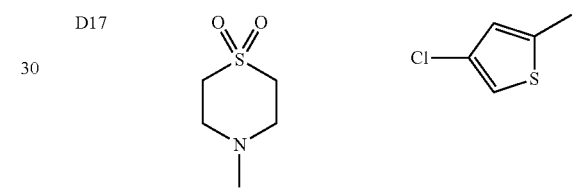 |
| D18 | 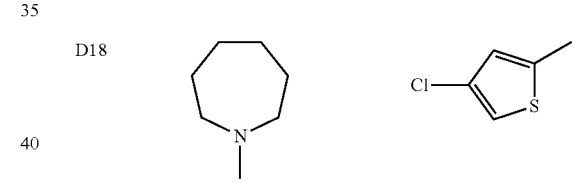 | 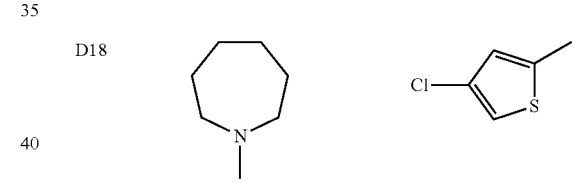 |
| D19 | 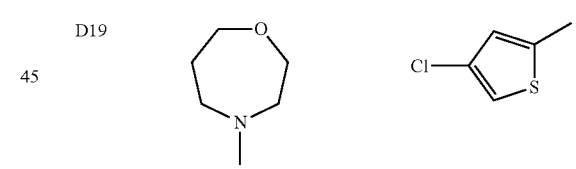 | 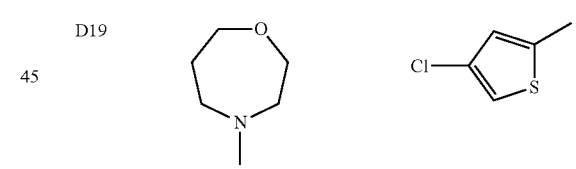 |
| D20 | 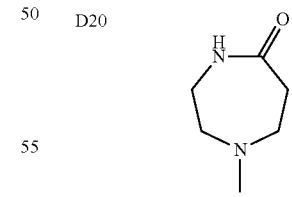 | 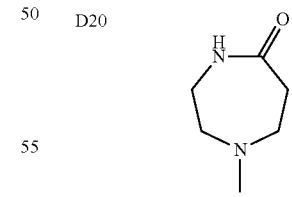 |
| D21 | 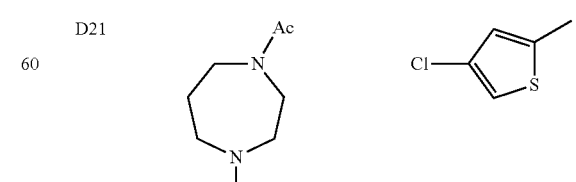 | 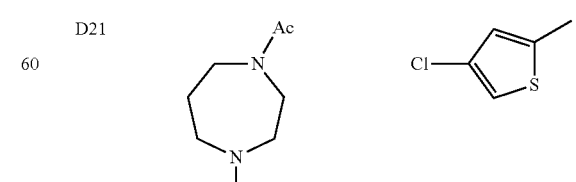 |

TABLE 105-continued

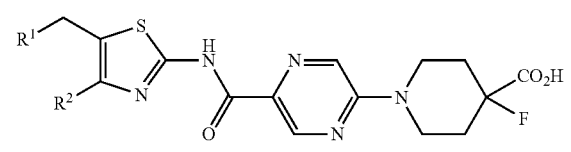

| No. | R1 | R2 |
|---|---|---|
| D22 | N-methyl-4-(methylsulfonyl)-1,4-diazepane | 4-chloro-5-methylthiophene |
| D23 | 1-methyl-4-(methylsulfonyl)piperazine | 3-chloro-5-fluoro-4-methoxyphenyl (F, MeO, Cl) |
| D24 | 1-methyl-4-(N,N-dimethylsulfamoyl)piperazine | 3-chloro-5-fluoro-4-methoxyphenyl |
| D25 | 1-methyl-1,1-dioxothiomorpholine | 3-chloro-5-fluoro-4-methoxyphenyl |
| D26 | 1-methylazepane | 3-chloro-5-fluoro-4-methoxyphenyl |
| D27 | 4-methyl-1,4-oxazepane | 3-chloro-5-fluoro-4-methoxyphenyl |
| D28 | 1-methyl-1,4-diazepan-5-one | 3-chloro-5-fluoro-4-methoxyphenyl |

TABLE 105-continued

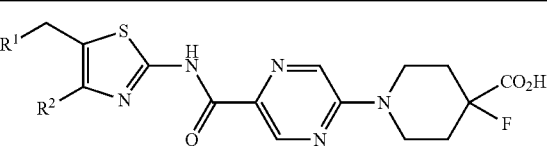

| No. | R1 | R2 |
|---|---|---|
| D29 | 1-acetyl-4-methyl-1,4-diazepane | 3-chloro-5-fluoro-4-methoxyphenyl |
| D30 | 1-methyl-4-(methylsulfonyl)-1,4-diazepane | 3-chloro-5-fluoro-4-methoxyphenyl |

TABLE 106

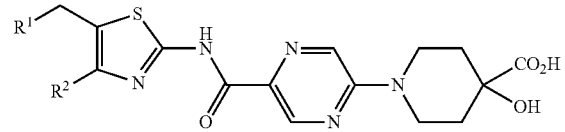

| No. | R1 | R2 |
|---|---|---|
| F1 | 1-methyl-3-(methylsulfonyl)pyrrolidine | 4-methoxy-3-(trifluoromethyl)phenyl (Me, MeO, CF3) |
| F2 | 3-methyl-2-oxa-5-azabicyclo[2.2.1] | 4-methoxy-3-(trifluoromethyl)phenyl |
| F3 | 4-methylmorpholine | 4-methoxy-3-(trifluoromethyl)phenyl |
| F4 | N-methyl-1-oxa-8-azaspiro[4.5] | 4-methoxy-3-(trifluoromethyl)phenyl |

TABLE 106-continued

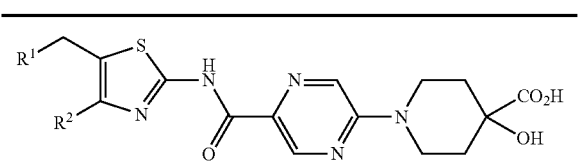

| No. | R1 | R2 |
|---|---|---|
| F5 | 4-methylpiperazin-1-yl (N-Me) | 4-MeO-3-CF3-phenyl |
| F6 | 4-methylpiperazine-1-carboxylate (CO2Me on N) | 4-MeO-3-CF3-phenyl |
| F7 | 4-methylpiperazine-1-CONMe2 | 4-MeO-3-CF3-phenyl |
| F8 | 1-methyl-3-(SO2Me)pyrrolidine | 3-MeO-5-CF3-phenyl |
| F9 | 3-methyl-2-oxa-5-azabicyclo | 3-MeO-5-CF3-phenyl |
| F10 | 4-methylmorpholine | 3-MeO-5-CF3-phenyl |
| F11 | 1-oxa-9-azaspiro, N-Me | 3-MeO-5-CF3-phenyl |

TABLE 106-continued

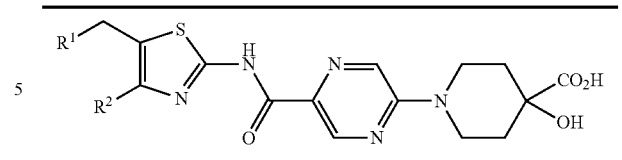

| No. | R1 | R2 |
|---|---|---|
| F12 | Me (on 4-methylpiperazin-1-yl) | 3-MeO-5-CF3-phenyl |
| F13 | CO2Me (on 4-methylpiperazin-1-yl) | 3-MeO-5-CF3-phenyl |
| F14 | CONMe2 (on 4-methylpiperazin-1-yl) | 3-MeO-5-CF3-phenyl |

TABLE 107

| No. | R1 | R2 |
|---|---|---|
| F15 | SO2Me (on 4-methylpiperazin-1-yl) | 4-MeO-3-CF3-phenyl |
| F16 | SO2NMe2 (on 4-methylpiperazin-1-yl) | 4-MeO-3-CF3-phenyl |
| F17 | 1,1-dioxo-4-methylthiomorpholine | 4-MeO-3-CF3-phenyl |

TABLE 107-continued

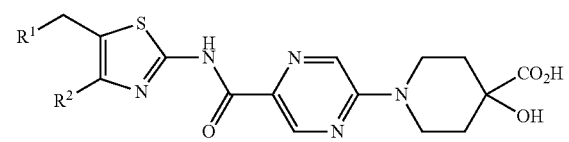
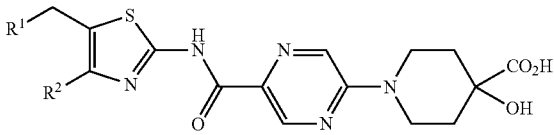

| No. | R1 | R2 |
|---|---|---|
| F18 | N-methylazepane | 4-methyl-2-methoxy-trifluoromethylphenyl |
| F19 | N-methyl-1,4-oxazepane | 4-methyl-2-methoxy-trifluoromethylphenyl |
| F20 | N-methyl-oxo-1,4-diazepane | 4-methyl-2-methoxy-trifluoromethylphenyl |
| F21 | 1-Ac-4-methyl-1,4-diazepane | 4-methyl-2-methoxy-trifluoromethylphenyl |
| F22 | 1-SO₂Me-4-methyl-1,4-diazepane | 4-methyl-2-methoxy-trifluoromethylphenyl |
| F23 | 1-SO₂Me-4-methylpiperazine | 3-methyl-5-methoxy-trifluoromethylphenyl |
| F24 | 1-SO₂NMe₂-4-methylpiperazine | 3-methyl-5-methoxy-trifluoromethylphenyl |
| F25 | 4-methylthiomorpholine-1,1-dioxide | 3-methyl-5-methoxy-trifluoromethylphenyl |
| F26 | N-methylazepane | 3-methyl-5-methoxy-trifluoromethylphenyl |
| F27 | N-methyl-1,4-oxazepane | 3-methyl-5-methoxy-trifluoromethylphenyl |
| F28 | N-methyl-oxo-1,4-diazepane | 3-methyl-5-methoxy-trifluoromethylphenyl |
| F29 | 1-Ac-4-methyl-1,4-diazepane | 3-methyl-5-methoxy-trifluoromethylphenyl |
| F30 | 1-SO₂Me-4-methyl-1,4-diazepane | 3-methyl-5-methoxy-trifluoromethylphenyl |

TABLE 108

| No. | R1 | R2 |
|---|---|---|
| H1 | 3-(methylsulfonyl)-1-methylpyrrolidine (SO₂Me on pyrrolidine, N-Me) | 4-chloro-5-methylthiophen-2-yl |
| H2 | 2-oxa-5-azabicyclo[2.2.1]heptane, N-Me | 4-chloro-5-methylthiophen-2-yl |
| H3 | 4-methylmorpholine | 4-chloro-5-methylthiophen-2-yl |
| H4 | 1-oxa-9-azaspiro[5.4] (oxa-spiro), N-Me | 4-chloro-5-methylthiophen-2-yl |
| H5 | 1,4-dimethylpiperazine | 4-chloro-5-methylthiophen-2-yl |
| H6 | 4-methyl-1-(methoxycarbonyl)piperazine | 4-chloro-5-methylthiophen-2-yl |
| H7 | 4-methyl-1-(N,N-dimethylcarbamoyl)piperazine | 4-chloro-5-methylthiophen-2-yl |
| H8 | 3-(methylsulfonyl)-1-methylpyrrolidine | 3-fluoro-4-methoxy-5-chloro-phenyl (F, MeO, Cl) |
| H9 | 2-oxa-5-azabicyclo[2.2.1]heptane, N-Me | 3-fluoro-4-methoxy-5-chloro-phenyl |
| H10 | 4-methylmorpholine | 3-fluoro-4-methoxy-5-chloro-phenyl |
| H11 | 1-oxa-9-azaspiro oxa-spiro, N-Me | 3-fluoro-4-methoxy-5-chloro-phenyl |
| H12 | 1,4-dimethylpiperazine | 3-fluoro-4-methoxy-5-chloro-phenyl |
| H13 | 4-methyl-1-(methoxycarbonyl)piperazine | 3-fluoro-4-methoxy-5-chloro-phenyl |
| H14 | 4-methyl-1-(N,N-dimethylcarbamoyl)piperazine | 3-fluoro-4-methoxy-5-chloro-phenyl |

TABLE 109

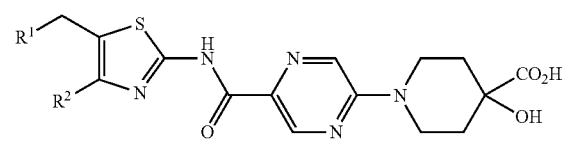

| No. | R1 | R2 |
|---|---|---|
| H15 |  |  |
| H16 |  | 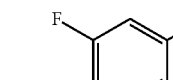 |
| H17 |  | 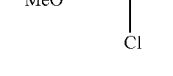 |
| H18 |  | 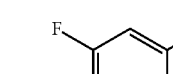 |
| H19 |  | 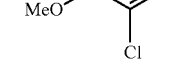 |
| H20 |  | 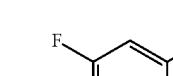 |
| H21 |  | 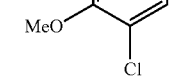 |

TABLE 109-continued

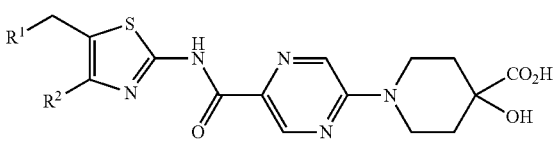

| No. | R1 | R2 |
|---|---|---|
| H22 | piperazine-SO2Me (7-membered, N-Me) | 4-chloro-thiophene |
| H23 | piperazine-SO2Me (N-Me) | 3-fluoro-5-methyl-2-methoxy-chloro phenyl |
| H24 | piperazine-SO2NMe2 (N-Me) | 3-fluoro-5-methyl-2-methoxy-chloro phenyl |
| H25 | thiomorpholine-1,1-dioxide (N-Me) | 3-fluoro-5-methyl-2-methoxy-chloro phenyl |
| H26 | azepane (N-Me) | 3-fluoro-5-methyl-2-methoxy-chloro phenyl |
| H27 | 1,4-oxazepane (N-Me) | 3-fluoro-5-methyl-2-methoxy-chloro phenyl |
| H28 | diazepan-5-one (N-Me) | 3-fluoro-5-methyl-2-methoxy-chloro phenyl |

TABLE 109-continued

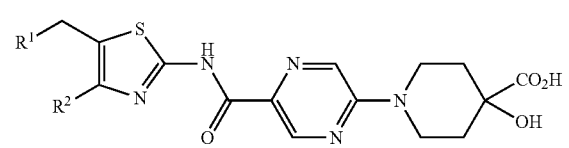

| No. | R1 | R2 |
|---|---|---|
| H29 | N-Ac / N-Me (homopiperazine) | F, MeO, Cl phenyl |
| H30 | N-SO2Me / N-Me (homopiperazine) | F, MeO, Cl phenyl |

TABLE 110

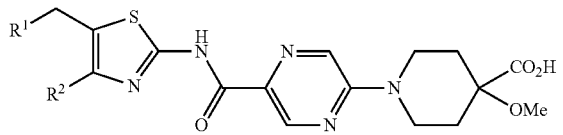

| No. | R1 | R2 |
|---|---|---|
| I1 | 1-methyl-3-(SO2Me)pyrrolidine | MeO, CF3 phenyl |
| I2 | 2-oxa-5-azabicyclo, N-Me | MeO, CF3 phenyl |
| I3 | 4-methylmorpholine | MeO, CF3 phenyl |
| I4 | 1-oxa-spiro[4.5], N-Me | MeO, CF3 phenyl |

TABLE 110-continued

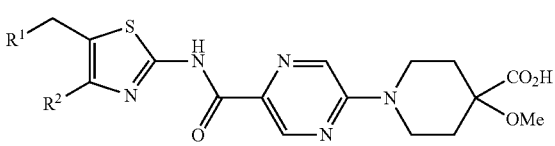

| No. | R1 | R2 |
|---|---|---|
| I5 | 1,4-dimethylpiperazine | MeO, CF3 phenyl |
| I6 | 4-methyl-1-(CO2Me)piperazine | MeO, CF3 phenyl |
| I7 | 4-methyl-1-(CONMe2)piperazine | MeO, CF3 phenyl |
| I8 | 1-methyl-3-(SO2Me)pyrrolidine | MeO, CF3 phenyl (3,5) |
| I9 | 2-oxa-5-azabicyclo, N-Me | MeO, CF3 phenyl (3,5) |
| I10 | 4-methylmorpholine | MeO, CF3 phenyl (3,5) |
| I11 | 1-oxa-spiro[4.5], N-Me | MeO, CF3 phenyl (3,5) |

TABLE 110-continued

Structure: R¹ and R² substituents on thiazole-pyrazine-piperidine core with CO₂H and OMe groups

| No. | R1 | R2 |
|-----|----|----|
| I12 | 4-methylpiperazin-1-yl (N-Me) | 3-MeO-5-CF₃-phenyl |
| I13 | 4-methylpiperazin-1-yl with CO₂Me | 3-MeO-5-CF₃-phenyl |
| I14 | 4-methylpiperazin-1-yl with CONMe₂ | 3-MeO-5-CF₃-phenyl |

TABLE 111

| No. | R1 | R2 |
|-----|----|----|
| I15 | 4-methylpiperazin-1-yl with SO₂Me | 4-MeO-3-CF₃-phenyl |
| I16 | 4-methylpiperazin-1-yl with SO₂NMe₂ | 4-MeO-3-CF₃-phenyl |
| I17 | 1,1-dioxo-thiomorpholin-4-yl (N-Me) | 4-MeO-3-CF₃-phenyl |

TABLE 111-continued

| No. | R1 | R2 |
|-----|----|----|
| I18 | N-methyl-azepan-1-yl | 4-MeO-3-CF₃-phenyl |
| I19 | 1,4-oxazepan-4-yl (N-Me) | 4-MeO-3-CF₃-phenyl |
| I20 | 7-oxo-1,4-diazepan-4-yl (N-Me) | 4-MeO-3-CF₃-phenyl |
| I21 | 1,4-diazepanyl (N-Ac, N-Me) | 4-MeO-3-CF₃-phenyl |
| I22 | 1,4-diazepanyl (N-SO₂Me, N-Me) | 4-MeO-3-CF₃-phenyl |
| I23 | 4-methylpiperazin-1-yl with SO₂Me | 3-MeO-5-CF₃-phenyl |
| I24 | 4-methylpiperazin-1-yl with SO₂NMe₂ | 3-MeO-5-CF₃-phenyl |

TABLE 111-continued

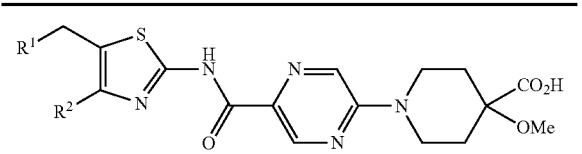

| No. | R1 | R2 |
|---|---|---|
| I25 | 4-methyl-1,1-dioxo-thiomorpholinyl | 3-MeO-5-CF3-phenyl |
| I26 | 1-methyl-azepanyl | 3-MeO-5-CF3-phenyl |
| I27 | 4-methyl-1,4-oxazepanyl | 3-MeO-5-CF3-phenyl |
| I28 | 1-methyl-5-oxo-1,4-diazepanyl | 3-MeO-5-CF3-phenyl |
| I29 | 4-Ac-1-methyl-1,4-diazepanyl | 3-MeO-5-CF3-phenyl |
| I30 | 4-SO2Me-1-methyl-1,4-diazepanyl | 3-MeO-5-CF3-phenyl |

TABLE 112

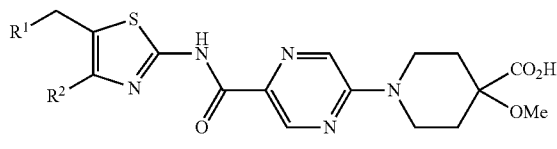

| No. | R1 | R2 |
|---|---|---|
| J1 | 3-SO2Me-1-methyl-pyrrolidinyl | 4-Cl-5-methyl-thien-2-yl |
| J2 | 5-methyl-2-oxa-5-azabicyclo[2.2.1]heptyl | 4-Cl-5-methyl-thien-2-yl |
| J3 | 4-methyl-morpholinyl | 4-Cl-5-methyl-thien-2-yl |
| J4 | N-methyl-1-oxa-spiro[4.5] | 4-Cl-5-methyl-thien-2-yl |
| J5 | 1,4-dimethyl-piperazinyl | 4-Cl-5-methyl-thien-2-yl |
| J6 | 1-CO2Me-4-methyl-piperazinyl | 4-Cl-5-methyl-thien-2-yl |
| J7 | 1-CONMe2-4-methyl-piperazinyl | 4-Cl-5-methyl-thien-2-yl |
| J8 | 3-SO2Me-1-methyl-pyrrolidinyl | 3-F-4-MeO-5-Cl-phenyl |

TABLE 112-continued

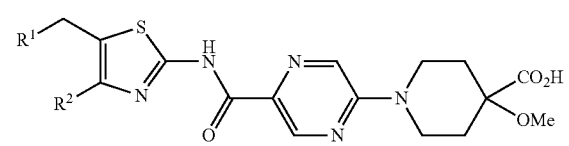

| No. | R1 | R2 |
|---|---|---|
| J9 | 2-methyl-2-azabicyclo[2.2.1] (oxa-pyrrolidine, N-Me) | 3-Cl-4-OMe-5-F-phenyl |
| J10 | 4-methylmorpholine | 3-Cl-4-OMe-5-F-phenyl |
| J11 | N-methyl 1-oxa-spiro morpholine | 3-Cl-4-OMe-5-F-phenyl |
| J12 | 1,4-dimethylpiperazine | 3-Cl-4-OMe-5-F-phenyl |
| J13 | 4-methyl-1-(CO2Me)piperazine | 3-Cl-4-OMe-5-F-phenyl |
| J14 | 4-methyl-1-(CONMe2)piperazine | 3-Cl-4-OMe-5-F-phenyl |

TABLE 113

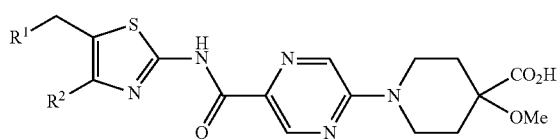

| No. | R1 | R2 |
|---|---|---|
| J15 | 4-methyl-1-(SO2Me)piperazine | 4-Cl-thiophen-2-yl |
| J16 | 4-methyl-1-(SO2NMe2)piperazine | 4-Cl-thiophen-2-yl |
| J17 | 4-methyl-thiomorpholine-1,1-dioxide | 4-Cl-thiophen-2-yl |
| J18 | N-methylazepane | 4-Cl-thiophen-2-yl |
| J19 | N-methyl-1,4-oxazepane | 4-Cl-thiophen-2-yl |
| J20 | N-methyl-5-oxo-1,4-diazepane | 4-Cl-thiophen-2-yl |
| J21 | N-methyl-1-Ac-1,4-diazepane | 4-Cl-thiophen-2-yl |

TABLE 113-continued

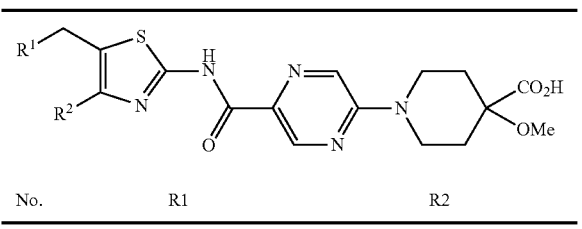

| No. | R1 | R2 |
|---|---|---|
| J22 | 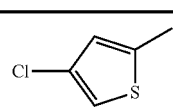 | 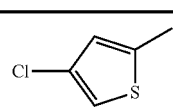 |
| J23 | 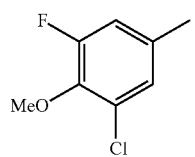 | |
| J24 | 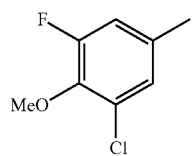 | |
| J25 | 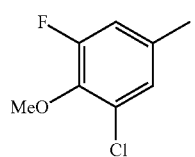 | |
| J26 | 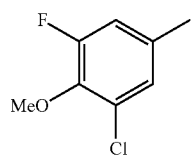 | |
| J27 | 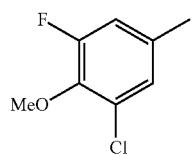 | |
| J28 | 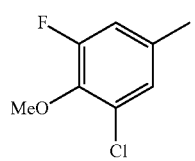 | |

TABLE 113-continued

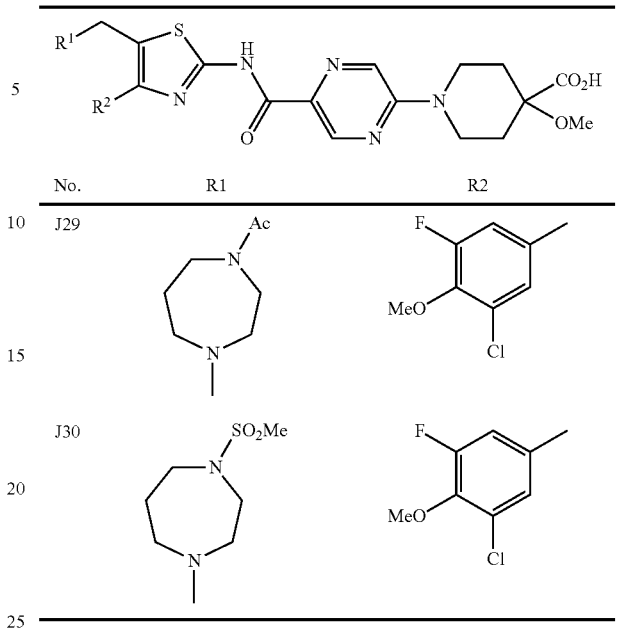

| No. | R1 | R2 |
|---|---|---|
| J29 | | |
| J30 | | |

INDUSTRIAL APPLICABILITY

The compound of the formula (I) or a salt thereof can be used as an agent for preventing and/or treating bladder or urinary tract diseases, related to bladder contraction by a muscarinic $M_3$ receptor, as a muscarinic $M_3$ receptor positive allosteric modulator.

The invention claimed is:

1. A compound of formula (I) or a salt thereof:

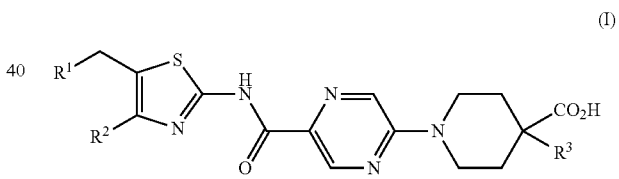

wherein
$R^1$ is —N(—$R^{11}$)(—$R^{12}$), or cyclic amino which may be substituted;
$R^{11}$ is $C_{1-6}$ alkyl;
$R^{12}$ is $C_{1-6}$ alkyl which may be substituted, or $C_{3-8}$ cycloalkyl which may be substituted;
$R^2$ is aryl which may be substituted, a monocyclic aromatic hetero ring which may be substituted, or a bicyclic aromatic hetero ring which may be substituted; and
$R^3$ is —H, —OH, —O—($C_{1-6}$ alkyl), or halogen.

2. The compound or a salt thereof according to claim 1, wherein $R^1$ is cyclic amino selected from the group consisting of pyrrolidin-1-yl, piperidin-1-yl, azetidin-1-yl, and morpholin-4-yl, or —N(—$R^{11}$)(—$R^{12}$), and the cyclic amino may be substituted with the same or different 1 to 3 substituent(s) selected from a Group G1,
in which the Group G1 is a group selected from the group consisting of
$C_{1-6}$ alkyl which may be substituted with the same or different 1 to 3 substituent(s) selected from the group consisting of —OH, —O—($C_{1-6}$ alkyl), and halogen;

—O—($C_{1-6}$ alkyl);
$C_{3-8}$ cycloalkyl;
halogen; and
—CN;
$R^{11}$ is $C_{1-6}$ alkyl;
$R^{12}$ is $C_{1-6}$ alkyl which may be substituted with —O—($C_{1-6}$ alkyl), or $C_{3-8}$ cycloalkyl which may be substituted with $C_{1-6}$ alkyl substituted with —O—($C_{1-6}$ alkyl);
$R^2$ is phenyl which may be substituted with the same or different 1 to 5 substituent(s) selected from a Group G2, thienyl which may be substituted with the same or different 1 to 3 substituent(s) selected from a Group G3, thiazolyl which may be substituted with the same or different 1 to 2 substituent(s) selected from the Group G3, or 2,3-dihydrobenzofuranyl which may be substituted with the same or different 1 to 5 substituent(s) selected from the Group G3,
in which the Group G2 is a group selected from the group consisting of
$C_{1-6}$ alkyl which may be substituted with the same or different 1 to 5 halogen(s);
—O—($C_{1-6}$ alkyl which may be substituted with the same or different 1 to 5 substituent(s) selected from the group consisting of halogen and —O—($C_{1-6}$ alkyl));
an —O-saturated hetero ring;
halogen;
—N($C_{1-6}$ alkyl)$_2$;
—NH($C_{1-6}$ alkyl);
—NH$_2$; and
cyclic amino, and
the Group G3 is a group selected from the group consisting of
$C_{1-6}$ alkyl which may be substituted with the same or different 1 to 5 halogen(s);
—O—($C_{1-6}$ alkyl which may be substituted with the same or different 1 to 5 halogen(s));
halogen;
—N($C_{1-6}$ alkyl)$_2$;
—NH($C_{1-6}$ alkyl);
—NH$_2$; and
cyclic amino; and
$R^3$ is —H, —OH, methoxy, or fluoro.

3. The compound or a salt thereof according to claim wherein $R^2$ is phenyl or thienyl, in which the phenyl may be substituted with the same or different 1 to 5 substituent(s) selected from a group G2 which is a group selected from the group consisting of
$C_{1-6}$ alkyl which may be substituted with the same or different 1 to 5 halogen(s);
—O—($C_{1-6}$ alkyl which may be substituted with the same or different 1 to 5 substituent(s) selected from the group consisting of halogen and —O—($C_{1-6}$ alkyl));
an —O-saturated hetero ring;
halogen;
—N($C_{1-6}$ alkyl)$_2$; and
cyclic amino; and
the thienyl may be substituted with the same or different 1 to 3 substituent(s) selected from a group G3 which is a group selected from the group consisting of
$C_{1-6}$ alkyl which may be substituted with the same or different 1 to 5 halogen(s); and
halogen(s).

4. The compound or a salt thereof according to claim 3, wherein $R^1$ is cyclic amino selected from the group consisting of pyrrolidin-1-yl and piperidin-1-yl, or —N(—$R^{11}$)(—$R^{12}$), and the cyclic amino may be substituted with $C_{1-6}$ alkyl which may be substituted with the same or different 1 to 3 substituent(s) selected from the group consisting of —O—($C_{1-6}$ alkyl) and halogen;
$R^{12}$ is $C_{1-6}$ alkyl which may be substituted with —O—($C_{1-6}$ alkyl);
$R^2$ is phenyl or thienyl, in which the phenyl may be substituted with the same or different 1 to 5 substituent(s) selected from a Group G2 which is a group selected from the group consisting of
$C_{1-6}$ alkyl which may be substituted with the same or different 1 to 5 halogen(s);
—O—($C_{1-6}$ alkyl which may be substituted with the same or different 1 to 5 substituent(s) selected from the group consisting of halogen and —O—($C_{1-6}$ alkyl));
halogen; and
—N($C_{1-6}$ alkyl)$_2$;
and the thienyl may be substituted with the same or different 1 to 3 halogen(s); and
$R^3$ is —H, —OH, or fluoro.

5. The compound or a salt thereof according to claim 4, wherein $R^1$ is cyclic amino selected from the group consisting of pyrrolidin-1-yl and piperidin-1-yl, and the cyclic amino is substituted with $C_{1-6}$ alkyl which may be substituted with the same or different 1 to 3 —O—($C_{1-6}$ alkyl) group(s);
$R^2$ is phenyl or thienyl, in which the phenyl may be substituted with the same or different 1 to 3 substituent(s) selected from a Group G2 which is a group selected from the group consisting of
$C_{1-6}$ alkyl which may be substituted with the same or different 1 to 5 halogen(s);
—O—($C_{1-6}$ alkyl); and
halogen;
and the thienyl may be substituted with the same or different 1 to 3 halogen(s),
and
$R^3$ is —H.

6. The compound or a salt thereof according to claim 5, wherein $R^1$ is cyclic amino selected from the group consisting of pyrrolidin-1-yl and piperidin-1-yl, and the cyclic amino is substituted with $C_{1-6}$ alkyl; and
$R^2$ is phenyl or thienyl, in which the phenyl may be substituted with the same or different 1 to 3 substituent(s) selected from a Group G2 which is a group selected from the group consisting of
$C_{1-6}$ alkyl which may be substituted with the same or different 1 to 5 halogen(s); and
—O—($C_{1-6}$ alkyl)
and the thienyl may be substituted with the same or different 1 to 3 halogen(s).

7. The compound or a salt thereof according to claim 6, wherein $R^1$ is cyclic amino selected from the group consisting of pyrrolidin-1-yl and piperidin-1-yl, and the cyclic amino is substituted with the same or different 1 to 3 substituent(s) selected from the group consisting of methyl and ethyl; and
$R^2$ is phenyl or thienyl, in which the phenyl may be substituted with the same or different 1 to 2 substituent(s) selected from the group consisting of trifluoromethyl and methoxy, and the thienyl may be substituted with one chloro.

8. The compound or a salt thereof according to claim 7, wherein $R^2$ is phenyl which may be substituted with the same or different 1 to 2 substituent(s) selected from the group consisting of trifluoromethyl and methoxy.

9. The compound or a salt thereof according to claim 7, wherein $R^2$ is thienyl which may be substituted with one chloro.

10. The compound or a salt thereof according to claim 1, wherein the compound is a compound selected from the group consisting of:
1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid,
1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylic acid,
1-{5-[(5-{[(2R)-2-ethylpyrrolidin-1-yl]methyl}-4-[3-fluoro-5-(trifluoromethyl)phenyl]-1,3-thiazol-2-yl)carbamoyl]pyrazin-2-yl}piperidine-4-carboxylic acid, and
1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylic acid.

11. A pharmaceutical composition, comprising a compound or a salt thereof according to claim 10, and a pharmaceutically acceptable excipient.

12. A method for treating a bladder or urinary tract disease, related to bladder contraction by a muscarinic $M_3$ receptor, comprising administering to a subject in need thereof an effective amount of a compound or a salt thereof according to claim 10.

13. The compound or a salt thereof according to claim 10, wherein the compound is
1-{5-[(4-[3-methoxy-5-(trifluoromethyl)phenyl]-5-{[(2R)-2-methylpiperidin-1-yl]methyl}-1,3-thiazol-2-yl)carbamoyl]pyrazin-2-yl}piperidine-4-carboxylic acid.

14. The compound or a salt thereof according to claim 10, wherein the compound is
1-(5-{[4-(4-chloro-2-thienyl)-5-{[(2R)-2-methylpyrrolidin-1-yl]methyl}-1,3-thiazol-2-yl]carbamoyl}pyrazin-2-yl)piperidine-4-carboxylic acid.

15. The compound or a salt thereof according to claim 10, wherein the compound is
1-{5-[(5-{[(2R)-2-ethylpyrrolidin-1-yl]methyl}-4-[3-fluoro-5-(trifluoromethyl)phenyl]-1,3-thiazol-2-yl)carbamoyl]pyrazin-2-yl}piperidine-4-carboxylic acid.

16. The compound or a salt thereof according to claim 10, wherein the compound is
1-{5-[(5-{[(2R)-2-ethylpyrrolidin-1-yl]methyl}-4-[4-methoxy-3-(trifluoromethyl)phenyl]-1,3-thiazol-2-yl)carbamoyl]pyrazin-2-yl}piperidine-4-carboxylic acid.

* * * * *

UNITED STATES PATENT AND TRADEMARK OFFICE
CERTIFICATE OF CORRECTION

PATENT NO. : 9,562,044 B2
APPLICATION NO. : 14/770648
DATED : February 7, 2017
INVENTOR(S) : Taisuke Takahashi et al.

Page 1 of 1

It is certified that error appears in the above-identified patent and that said Letters Patent is hereby corrected as shown below:

In the Claims

In Claim 3, Column 235, Lines 45-46:
"The compound or a salt thereof according to claim wherein $R^2$ is phenyl or thienyl, in which the phenyl may be"

Should be:
--The compound or a salt thereof according to claim 2 wherein $R^2$ is phenyl or thienyl, in which the phenyl may be--

Signed and Sealed this
Twenty-seventh Day of February, 2018

Andrei Iancu
*Director of the United States Patent and Trademark Office*